(12) United States Patent
Li et al.

(10) Patent No.: US 6,444,439 B1
(45) Date of Patent: Sep. 3, 2002

(54) CLONING AND CHARACTERIZATION OF A CDC15-LIKE ADAPTOR PROTEIN (CD2BP1)

(75) Inventors: Jing Li, Malden; Kazuhisa Nishizawa, Brookline; Wengian An, Framingham; Ellis L. Reinherz, Lincoln, all of MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 09/006,428

(22) Filed: Jan. 13, 1998

(51) Int. Cl.[7] ............................. C12P 21/06; C12N 1/20; C07K 17/00; C07H 21/04
(52) U.S. Cl. .................. 435/69.1; 435/252.3; 536/23.1; 536/23.5; 530/352
(58) Field of Search ............................. 536/23.1, 23.5; 435/252.3, 69.1; 530/352

(56) References Cited

U.S. PATENT DOCUMENTS 6,040,437 A1 * 3/2001 Lasky et al.

FOREIGN PATENT DOCUMENTS

| WO | WO9013644 | 11/1990 |
| WO | WO9835037 | 8/1998 |

OTHER PUBLICATIONS

EST Accession No. R00032, Mar. 1995.*
GenEMBL Accession No. U87814, Mar. 1997.*
Ausubel et al Current Protocols in Molecular Biology, J. Wiley & Sons, NY, 6.3.1–6.3.6, 16.0.1–16.2.11, 1994.*
GenEMBL Accession No. W85898, Feb. 1997.*
Ngo et al. The Protein Folding Problem and Tertiary Structure Prediction. K. Merz, Jr. and S. LeGrand, eds. Birkhauser Boston, pp. 492–495, 1995.
SPTREMBL_12 Accession No. P97814, May 1997.
Maniatis et al. Molecular Cloning, A Laboratory Manual, Cold Spring Harbor Laboratory, Chapter 7, 1982.
GenEmbl Accession No. U87814, 1997.
Moingeon, P. et al., "CD2–mediated adhesion facilitates T lymphocyte antigen recognition function," *Nature* 339:312–314, 1989.
Sayre, P.H. et al., "Structural and Binding Analysis of a Two Domain Extracellular CD2 Molecule," *J. Exp. Med* 169:995–1009, 1989.
Bierer, B.E. et al., "Synergistic T Cell Activation Via the Physiological Ligands for CD2 and the T Cell Receptor," *J. Exp. Med.* 168:1145–1156, 1988.
Chang, H.C. et al., "Dissection of the Human CD2 Intracellular Domain—Identification of a Segment Required for Signal Transduction and Interleukin 2 Production," *J. Exp. Med.* 169:2073–2083, 1989.
Boussiotis, V.A. et al., "CD2 is Involved in Maintenance and Reversal of Human Alloantigen–specific Clonal Anergy," *J. Exp. Med.* 180:1665–1673, 1994.

Somoza, C. et al., "Mutational Analysis of the CD2/CD58 Interaction: The Binding Site for CD58 Lies on One Face of the First Domain of Human CD2," *J. Exp. Med.* 178:549–558, 1993.
Hahn, W.C. and Bierer, B.E., "Separable Portions of the CD2 Cytoplasmic Domain Involved in Signaling and Ligand Avidity Regulation," *J. Exp. Med.* 178:1831–1836, 1993.
Arulanandam, A.R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.* 177:1439–1450, 1993.
Bell, G.M. et al., "The SH3 Domain of p56[lck] Binds to Proline–rich Sequences in the Cytoplasmic Domain of CD2," *J. Exp. Med.* 183:169–178, 1996.
Arulanandam, A.R.N. et al., "Interaction between Human CD2 and CD58 Involves the Major β Sheet Surface of each of Their Respective Adhesion Domains," *J. Exp. Med.* 180:1861–1871, 1994.
Koyasu, S. et al., "Role of interaction of CD2 molecules with lymphocyte function–associated antigen 3 in T–cell recognition of nominal antigen," *Proc. Natl. Acad. Sci. USA* 87:2603–2607, 1990.
Arulanandam, A.R.N., "The CD58 (LFA–3) binding site is localized and highly charged surface area on the AGFCC'C face of the human CD2 adhesion domain," *Proc. Natl. Acad. Sci. USA* 90:11613–11617, 1993.
Gollob, J.A., "Molecular Interaction Between CD58 and CD2 Counter–Receptors Mediates the Ability of Monocytes to Augment T Cell Activatin by IL–12[1],", *The Jour. of Immunol.* 157:1886–1893, 1996.
Gassman, M. et al., "Identification of a signaling complex involving CD2, ζ chain and p59[fyn] in T lymphocytes," *Eur. J. Immunol.* 24:139–144, 1994.
Moingeon, P. et al., "The Structural Biology of CD2," *Immunol. Review* 111:111–144, 1989.
Meuer, S.C. et al., "An Alternative Pathway of T–Cell Activation: A Functional Role for the 50 kd T11 Sheep Erythrocyte Receptor Protein," *Cell* 36:897–906, 1984.
Recny, M.A. et al., "Structural and Functional Characterization of the CD2 Immunoadhesion Domain," *The Jour. of Biol. Chem.* 265(15): 8542–8549, 1990.
Tavernor, A.S. et al., "Expression cloning of an equine T–lymphocyte glycoprotein CD2 cDNA Structure–based analysis of conserved sequence elements," *Eur. J. Biochem.* 219:969–976, 1994.

(List continued on next page.)

Primary Examiner—Christina Chan
Assistant Examiner—Phuong N. Huynh
(74) Attorney, Agent, or Firm—Hamilton, Brook, Smith & Reynolds, P.C.

(57) ABSTRACT

A human CD2 cytoplasmic tail binding protein, CD2BP1, is described, as well as the nucleic acids encoding the protein. Also described are expression vectors and recombinant host cells comprising nucleic acids encoding the CD2BP1 protein, and methods of use for the CD2BP1 protein and nucleic acids encoding the CD2BP1 protein.

8 Claims, 14 Drawing Sheets-

OTHER PUBLICATIONS

Davidson, D. et al., "Inhibitory Tyrosine Protein Kinase p50$^{csk}$ Is Associated with Protein–tyrosine Phosphatase PTP–PEST in hemopoietic and Non–hemopoietic Cells," *The Jour. of Biol. Chem.* 272 (37):23455–23462, 1997.

Cloutier, J.F. et al., "Requirement of the SH3 and SH2 Domains for the Inhibitory Function of Tyrosine Protein Kinase p50$^{csk}$ in T Lymphocytes," *Mol. and Cell. Biol.* 15(11):5937–5944, 1995.

Li, J. et al., "Ligand–induced Conformational Change Within the CD2 Ectodomain Accompanies Receptor Clustering: Implication for Molecular Lattice Formation," *J. Mol. Biol.* 263:209–226, 1996.

Bierer, B.E. et al., "The Biologic Roles of CD2, CD4 and CD8 in T–Cell Activation," *Ann. Rev. Immunol.* 7:579–599, 1989.

Chang H.C. et al., "Involvement of the PPPGHR Motif in T Cell Activation Via CD2," *J. Exp. Med.* 172:351–355, 1990.

Gollob, J.A. et al., "CD2 Regulates Responsiveness of Activated T Cells to Interluekin 12," *J. Exp. Med.* 182:721–731, 1995.

Spencer S, et al. "PSTPIP: A tyrosine phosphorylated cleavage furrow–associated protein that is a substrate for a pest tyrosine phosphatase". *J. Cell Biol.* 138(4):845–860, 1997.

Wilson, L.A., et al. "Pest phosphatase interacting protein homolog (human): H–PIP". Genbank, Accession No. AAD00762/U94778, Apr. 21, 1997.

Bell, G.M. et al. "The SH3 domain of the p56lck binds to proline–rich sequences in the cytoplasmic domain of CD2". *J. Exp. Med. 183* :169–178 1996.

Li J. et al. "A cdc15–like adaptor protein (CD2BP1) interacts with the CD2 cytoplasmic domain and regulates CD2–triggered adhesion". *Embo J.* 17(24):7320–7336, 1998.

Milanese et al., "Clonal analysis of B cell growth and differentiation activities induced from T lymphocytes upon triggering of T3 and ti and T11 pathways,", *J. Immunol.* 135:1884–1890, 1985.

Rosenberg et al., "Observations on the systemic administration of autologous lymphokine–activated killer cells and recombinant interleukin–2 to patients with metastic cancer", *N.E. J. of Med.* 313:1485–1492, 1985.

Sewell, W.A. et al., "Molecular cloning of the human T–lymphocyte surface CD2(T11) antigen", *Biochem. Soc. Trans.* 14:1009, 1986.

Leca, G. et al., "The Sheep Erythrocyte Receptor and Both α and β Chains of the Human T–Lymphocyte Antigen Receptor Bind the Mitogenic Lectin (Phytohaemagglutinin) from *Phaseolus vulgaris*", *Scand. J. Immunol.* 23:535–544, 1986.

Sewell, W.A. et al., "Molecular cloning of the human T–lymphocyte surface CD2 (T11) antigen", *Proc. Natl. Acad. Sci., USA* 83:8718–8722, Nov. 1986.

Brown, M.H. et al., "Purification and N–terminal amino acid sequence of the human T lymphocyte CD2 (T11) surface antigen", *Eur. J. immunol.* 17:15–20, 1987.

Sayre, P.H. et al., "Molecular cloning and expression of T11 cDNAs reveal a receptor–like structure on human T lymphocytes", *Proc. Natl. Acad. Sci., USA* 84:2941–2945, 1987.

* cited by examiner

```
            1                                                    50
CD2BP1L  MMPQLQFKDA FWCRDFTAHT GYEVLLQRLL DGRKMCKDME ELLRQRAQAE
CD2BP1S  MMPQLQFKDA FWCRDFTAHT GYEVLLQRLL DGRKMCKDME ELLRQRAQAE 51                                                   100
CD2BP1L  ERYGKELVQI ARKAGGQTEI NSLRASFDSL KQQMENVGSS HIQLALTLRE
CD2BP1S  ERYGKELVQI ARKAGGQTEI NSLRASFDSL KQQMENVGSS HIQLALTLRE 101                                                  150
CD2BP1L  ELRSLEEFRE RQKEQRKKYE AVMDRVQKSK LSLYKKAMES KKTYEQKCRD
CD2BP1S  ELRSLEEFRE RQKEQRKKYE AVMDRVQKSK LSLYKKAMES KKTYEQKCRD 151                                                  200
CD2BP1L  ADDAEQAFER ISANGHQKQV EKSQNKARQC KDSATEAERV YRQSIAQLEK    cdc15
CD2BP1S  ADDAEQAFER ISANGHQKQV EKSQNKARQC KDSATEAERV YRQSIAQLEK 201                                                  250
CD2BP1L  VRAEWEQEHR TTCEAFQLQE FDRLTILRNA LWVHSNQLSM QCVKDDELYE
CD2BP1S  VRAEWEQEHR TTCEAFQLQE FDRLTILRNA LWVHSNQLSM QCVKDDELYE 251                                                  300
CD2BP1L  EVRLTLEGCS IDADIDSFIQ AKSTGTEPPA PVPYQNYYDR EVTPLTSSPG
CD2BP1S  EVRLTLEGCS IDADIDSFIQ AKSTGTEPPG EVRLAD.... ..........

301                                                  350
CD2BP1L  IQPSCGMIKR FSGLLHGSPK TTSLAASAAS TETLTPTPER NEGVYTAIAV
CD2BP1S  .....SAASR FSGLLHGSPK TTSLAASAAS TETLTPTPER NEGVYTAIAV 351                                                  400
CD2BP1L  QEIQGNPASP AQEYRALYDY TAQNPDELDL SAGDILEVIL EGEDGWWTVE
CD2BP1S  QEIQGNPASP AQEYRALYDY TAQNPDELDL SAGDILEVIL EGEDGWWTVE    SH3

401        416
CD2BP1L  RNGQRGFVPG SYLEKL
CD2BP1S  RNGQRGFVPG SYLEKL
```

FIG. 3

```
CD2BP1L  123
         MDRVQKSKLS LYKKAMESKK TYEQKCRDAD DAEQAFERIS ANGHQKQVEK  172
cdc15    ieelyqkkta leidlsekkd ayeysnkln ....symrqt kkmtgreldk CD2BP1L  173
         SQNKARQCKD SATEAERVYR QSIAQLEKVR AEWEQEHRTT CEAFQLQEFD  222
cdc15    ynlkirqaal avkkmdaeyr etnellltvt rewidrwtev cdafchieey CD2BP1L  223
         RLTILRNALW VHSNQISMQC VKDDELYEEV RLTLEGCSID ADIDSFIQAK  272
cdc15    rleflktnmw ayaniistac vkddesceki rltlentnid editqmicne CD2BP1L  273
         STGTEPPAPV PYQNYY  288
cdc15    gtgttipplp efndyf
```

FIG. 4

```
            1                                                                    50
CD2BP1SH3   ......PAQ EYRALYDYTA QNPDELDLSA GDILEVILEG ..........
spct        ..mdetgke lvlalydyqe ksprevtmkk gdiltlinst ..........
afod        .ptddetgke lvlalydyqe ksprevtmkk gdiltlinst ..........
myosinHC    ......pgpe qaralydfaa enpdeltfne gavvtvinks ..........
ab1int      ..........  .aiydyek dkedelsfqe galiyvlkkn ..........
cytoFa      ......iilg tyraiadyek tsgsemalst gdvvevveks ..........
grb2        gsrrasvgsm eaiakydfka taddelsfkr gdilkvlnee c.........
cdc15       ......pilg yvialydyqa qipeeisfqk gdtlmvl.rt q.........
cytoFb      ......yage pyvaikayta vegdevslle geavevlhkl l.........
PI3K        ....msaegy qvralydykk ereedidlhl gdiltvnkgs lvalgfsdgq 51                                                                   92
CD2BP1SH3   ..EDGMW TVER...... QRGFVPGSYL EKL....... ..
spct        ...nkdww kvev...... rqgfvpaayv kkld...... ..
afod        ...nkdww kvev...... rqgfvpaayv kkl....... ..
myosinHC    ...npdww egel...... qrgfvfpasyv elipr..... ..
ab1int      ...dgywy egvm...... vtglfpgnyv esim...... ..
cytoFa      ...esgww fcqm...... krgwipasfl eplds..... ..
grb2        ...dqnwy kael...... kdgfipkmyi emkphpefiv td
cdc15       ...edgww dgeiinvpns krglfpsnfv qtv....... ..
cytoFb      ...d.gww vir...kdd vtgyfpsmyl qksgq..... ..
PI3K        earpeeigwl ng..ynettg ergdfpgtyv eyigr..... ..
```

FIG. 5

Segment from CD2BP1L (1 to 1858) to be translated:

```
          10         20         30         40         50         60         70
   CTGCGCAGGC CTCGGGCTGC CTGCCTGCCT GCCTGCCTGG CCCGGCCCGA GCTCCAGCCT GCCTCTTCCA 80         90        100        110        120        130        140
   CTGGCCACTG CCTCCCACCC AGGGCTGGCA TCCTGCTCCC TGCCCTGGGT CCCAGACTGT GTCCTCCATC 150        160        170        180        190        200        210
   ACCGCAGGGT CGGTGAGGGG CTGGGCTGGA CACCAGGGCC CGCCCTCCCA TCACTGAGCT CCACTCCTTC 220        230        240        250        260        270        280
   CTCATTTTGC TGCTGATTCT AGCCCCAAAC AAAACAGGTT GAGCTTTTTC CTCCCCTCAG AAGCTCCTCT 290        300        310        320        330        340_       350
   CTGGCTCGTG GCTGCCTTCT GAGTGTTGCA GACGGCGCCG GCCGGGAAGG GGGGCCTGGG CCAGCCCTGC 360        370        380        390        400        410        420
   CAGGACTGGG ACGCTGCTGC TGGCGCCTGG CCCTCCATCA GGCCAGCCTG TGGCAGGAGA GTGAGCTTTG 430        439        448        457        466        475
             >
   CCGCGGCAGA CGCCTGAGG ATG ATG CCC CAG CTG CAG TTC AAA GAT GCC TTT TGG
                        MET MET Pro Gln Leu Gln Phe Lys Asp Ala Phe Trp 484        493        502        511        520        529
   TGC AGG GAC TTC ACA GCC CAC ACG GGC TAC GAG GTG CTG CTG CAG CGG CTT CTG
   Cys Arg Asp Phe Thr Ala His Thr Gly Tyr Glu Val Leu Leu Gln Arg Leu Leu 538        547        556        565        574        583
   GAT GGC AGG AAG ATG TGC AAA GAC ATG GAG GAG CTA CTG AGG CAG AGG GCC CAG
   Asp Gly Arg Lys MET Cys Lys Asp MET Glu Glu Leu Leu Arg Gln Arg Ala Gln 592        601        610        619        628        637
   GCG GAG GAG CGG TAC GGG AAG GAG CTG GTG CAG ATC GCA CGG AAG GCA GGT GGC
   Ala Glu Glu Arg Tyr Gly Lys Glu Leu Val Gln Ile Ala Arg Lys Ala Gly Gly 646        655        664        673        682        691
   CAG ACG GAG ATC AAC TCC CTG AGG GCC TCC TTT GAC TCC TTG AAG CAG CAA ATG
   Gln Thr Glu Ile Asn Ser Leu Arg Ala Ser Phe Asp Ser Leu Lys Gln Gln MET 700        709        718        727        736        745
   GAG AAT GTG GGC AGC TCA CAC ATC CAG CTG GCC CTG ACC CTG CGT GAG GAG CTG
   Glu Asn Val Gly Ser Ser His Ile Gln Leu Ala Leu Thr Leu Arg Glu Glu Leu
```

FIG.9A

```
      754              763            772            781            790            799
CGG  AGT  CTC  GAG  GAG  TTT  CGT  GAG  AGG  CAG  AAG  GAG  CAG  AGG  AAG  AAG  TAT  GAG
Arg  Ser  Leu  Glu  Glu  Phe  Arg  Glu  Arg  Gln  Lys  Glu  Gln  Arg  Lys  Lys  Tyr  Glu 808              817            826            835            844            853
GCC  GTC  ATG  GAC  CGG  GTC  CAG  AAG  AGC  AAG  CTG  TCG  CTC  TAC  AAG  AAG  GCC  ATG
Ala  Val  MET  Asp  Arg  Val  Gln  Lys  Ser  Lys  Leu  Ser  Leu  Tyr  Lys  Lys  Ala  MET 862              871            880            889            898            907
GAG  TCC  AAG  AAG  ACA  TAC  GAG  CAG  AAG  TGC  CGG  GAC  GCG  GAC  GAC  GCG  GAG  CAG
Glu  Ser  Lys  Lys  Thr  Tyr  Glu  Gln  Lys  Cys  Arg  Asp  Ala  Asp  Asp  Ala  Glu  Gln 916              925            934            943            952            961
GCC  TTC  GAG  CGC  ATT  AGC  GCC  AAC  GGC  CAC  CAG  AAG  CAG  GTG  GAG  AAG  AGT  CAG
Ala  Phe  Glu  Arg  Ile  Ser  Ala  Asn  Gly  His  Gln  Lys  Gln  Val  Glu  Lys  Ser  Gln 970              979            988            997           1006           1015
AAC  AAA  GCC  AGG  CAG  TGC  AAG  GAC  TCG  GCC  ACC  GAG  GCA  GAG  CGG  GTA  TAC  AGG
Asn  Lys  Ala  Arg  Gln  Cys  Lys  Asp  Ser  Ala  Thr  Glu  Ala  Glu  Arg  Val  Tyr  Arg 1024             1033           1042           1051           1060           1069
CAG  AGC  ATT  GCG  CAG  CTG  GAG  AAG  GTC  CGG  GCT  GAG  TGG  GAG  CAG  GAG  CAC  CGG
Gln  Ser  Ile  Ala  Gln  Leu  Glu  Lys  Val  Arg  Ala  Glu  Trp  Glu  Gln  Glu  His  Arg 1078             1087           1096           1105           1114           1123
ACC  ACC  TGT  GAG  GCC  TTT  CAG  CTG  CAA  GAG  TTT  GAC  CGG  CTG  ACC  ATT  CTC  CGC
Thr  Thr  Cys  Glu  Ala  Phe  Gln  Leu  Gln  Glu  Phe  Asp  Arg  Leu  Thr  Ile  Leu  Arg 1132             1141           1150           1159           1168           1177
AAC  GCC  CTG  TGG  GTG  CAC  AGC  AAC  CAG  CTC  TCC  ATG  CAG  TGT  GTC  AAG  GAT  GAT
Asn  Ala  Leu  Trp  Val  His  Ser  Asn  Gln  Leu  Ser  MET  Gln  Cys  Val  Lys  Asp  Asp 1186             1195           1204           1213           1222           1231
GAG  CTC  TAC  GAG  GAA  GTG  CGG  CTG  ACG  CTG  GAA  GGC  TGC  AGC  ATA  GAC  GCC  GAC
Glu  Leu  Tyr  Glu  Glu  Val  Arg  Leu  Thr  Leu  Glu  Gly  Cys  Ser  Ile  Asp  Ala  Asp 1240             1249           1258           1267           1276           1285
ATC  GAC  AGT  TTC  ATC  CAG  GCC  AAG  AGC  ACG  GGC  ACA  GAG  CCC  CCC  GCT  CCG  GTG
Ile  Asp  Ser  Phe  Ile  Gln  Ala  Lys  Ser  Thr  Gly  Thr  Glu  Pro  Pro  Ala  Pro  Val 1294             1303           1312           1321           1330           1339
CCC  TAC  CAG  AAC  TAT  TAC  GAT  CGG  GAG  GTC  ACC  CCG  CTG  ACC  AGC  AGC  CCT  GGC
Pro  Tyr  Gln  Asn  Tyr  Tyr  Asp  Arg  Glu  Val  Thr  Pro  Leu  Thr  Ser  Ser  Pro  Gly 1348             1357           1366           1375           1384           1393
ATA  CAG  CCG  TCC  TGC  GGC  ATG  ATA  AAG  AGG  TTC  TCT  GGA  CTG  CTG  CAC  GGA  AGT
Ile  Gln  Pro  Ser  Cys  Gly  MET  Ile  Lys  Arg  Phe  Ser  Gly  Leu  Leu  His  Gly  Ser 1402             1411           1420           1429           1438           1447
CCC  AAG  ACC  ACT  TCG  TTG  GCA  GCT  TCT  GCT  GCG  TCC  ACA  GAG  ACC  CTG  ACC  CCC
Pro  Lys  Thr  Thr  Ser  Leu  Ala  Ala  Ser  Ala  Ala  Ser  Thr  Glu  Thr  Leu  Thr  Pro
```

FIG.9B

|      | 1456 |      |      | 1465 |      |      | 1474 |      |      | 1483 |      |      | 1492 |      |      | 1501 |      |
|------|------|------|------|------|------|------|------|------|------|------|------|------|------|------|------|------|------|
| ACC  | CCC  | GAG  | CGG  | AAT  | GAG  | GGT  | GTC  | TAC  | ACA  | GCC  | ATC  | GCA  | GTG  | CAG  | GAG  | ATA  | CAG  |
| Thr  | Pro  | Glu  | Arg  | Asn  | Glu  | Gly  | Val  | Tyr  | Thr  | Ala  | Ile  | Ala  | Val  | Gln  | Glu  | Ile  | Gln  |

|      | 1510 |      |      | 1519 |      |      | 1528 |      |      | 1537 |      |      | 1546 |      |      | 1555 |      |
|------|------|------|------|------|------|------|------|------|------|------|------|------|------|------|------|------|------|
| GGA  | AAC  | CCG  | GCC  | TCA  | CCA  | GCC  | CAG  | GAG  | TAC  | CGG  | GCG  | CTC  | TAC  | GAT  | TAT  | ACA  | GCG  |
| Gly  | Asn  | Pro  | Ala  | Ser  | Pro  | Ala  | Gln  | Glu  | Tyr  | Arg  | Ala  | Leu  | Tyr  | Asp  | Tyr  | Thr  | Ala  |

|      | 1564 |      |      | 1573 |      |      | 1582 |      |      | 1591 |      |      | 1600 |      |      | 1609 |      |
|------|------|------|------|------|------|------|------|------|------|------|------|------|------|------|------|------|------|
| CAG  | AAC  | CCA  | GAT  | GAG  | CTG  | GAC  | CTG  | TCC  | GCG  | GGA  | GAC  | ATC  | CTG  | GAG  | GTG  | ATC  | CTG  |
| Gln  | Asn  | Pro  | Asp  | Glu  | Leu  | Asp  | Leu  | Ser  | Ala  | Gly  | Asp  | Ile  | Leu  | Glu  | Val  | Ile  | Leu  |

|      | 1618 |      |      | 1627 |      |      | 1636 |      |      | 1645 |      |      | 1654 |      |      | 1663 |      |
|------|------|------|------|------|------|------|------|------|------|------|------|------|------|------|------|------|------|
| GAA  | GGG  | GAG  | GAT  | GGC  | TGG  | TGG  | ACT  | GTG  | GAG  | AGG  | AAC  | GGG  | CAG  | CGT  | GGC  | TTC  | GTC  |
| Glu  | Gly  | Glu  | Asp  | Gly  | Trp  | Trp  | Thr  | Val  | Glu  | Arg  | Asn  | Gly  | Gln  | Arg  | Gly  | Phe  | Val  |

|      | 1672 |      |      | 1681 |      |      | 1690 |      |      | 1699 |      |      | 1708 |      |      | 1717 |      |
|------|------|------|------|------|------|------|------|------|------|------|------|------|------|------|------|------|------|
| CCT  | GGT  | TCC  | TAC  | CTG  | GAG  | AAG  | CTT  | TGA  | GGA  | AGG  | GCC  | AGG  | AGC  | CCC  | TTC  | GGA  | CCT  |
| Pro  | Gly  | Ser  | Tyr  | Leu  | Glu  | Lys  | Leu  | .    | Gly  | Arg  | Ala  | Arg  | Ser  | Pro  | Phe  | Gly  | Pro  |

|      | 1726 |      |      | 1735 |      |      | 1744 |      |      | 1753 |      |      | 1762 |      |      | 1771 |      |
|------|------|------|------|------|------|------|------|------|------|------|------|------|------|------|------|------|------|
| GCC  | CTG  | CCA  | GTG  | GAG  | CCA  | GCA  | GTG  | CCC  | CCA  | GCA  | CTG  | TCC  | CCA  | CCT  | TGC  | TAG  | GGC  |
| Ala  | Leu  | Pro  | Val  | Glu  | Pro  | Ala  | Val  | Pro  | Pro  | Ala  | Leu  | Ser  | Pro  | Pro  | Cys  |      | Gly  |

|      | 1780 |      |      | 1789 |      |      | 1798 |      |      | 1807 |      |      | 1816 |      |      | 1825 |      |
|------|------|------|------|------|------|------|------|------|------|------|------|------|------|------|------|------|------|
| CCA  | GAA  | CCA  | AGC  | GTC  | CCC  | CAG  | CCC  | CGA  | GAG  | GGA  | GCC  | TGT  | CGT  | CTC  | CCA  | GGG  | AAT  |
| Pro  | Glu  | Pro  | Ser  | Val  | Pro  | Gln  | Pro  | Arg  | Glu  | Gly  | Ala  | Cys  | Arg  | Leu  | Pro  | Gly  | Asn  |

|      | 1834 |      |      | 1843 |      |      | 1852 |      |      |      |      |
|------|------|------|------|------|------|------|------|------|------|------|------|
| AAA  | GGA  | GTG  | CGT  | TCT  | GTT  | CTA  | AAA  | AAA  | AAA  | AAA  |      |
| Lys  | Gly  | Val  | Arg  | Ser  | Val  | Leu  | Lys  | Lys  | Lys  | Lys  |      |

FIG.9C

Segment from CD2BP1S (1 to 1803) to be translated:

```
         10         20         30         40         50         60         70
CTGCGCAGGC CTCGGGCTGC CTGCCTGCCT GCCTGCCTGG CCCGGCCCGA GCTCCAGCCT GCCTCTTCCA 80         90        100        110        120        130        140
CTGGCCACTG CCTCCCACCC AGGGCTGGCA TCCTGCTCCC TGCCCTGGGT CCCAGACTGT GTCCTCCATC 150        160        170        180        190        200        210
ACCGCAGGGT CGGTGAGGGG CTGGGCTGGA CACCAGGGCC CGCCCTCCCA TCACTGAGCT CCACTCCTTC 220        230        240        250        260        270        280
CTCATTTTGC TGCTGATTCT AGCCCCAAAC AAAACAGGTT GAGCTTTTTC CTCCCCTCAG AAGCTCCTCT 290        300        310        320        330        340        350
CTGGCTCGTG GCTGCCTTCT GAGTGTTGCA GACGGCGCCG GCCGGGAAGG GGGGCCTGGG CCAGCCCTGC 360        370        380        390        400        410        420
CAGGACTGGG ACGCTGCTGC TGGCGCCTGG CCCTCCATCA GGCCAGCCTG TGGCAGGAGA GTGAGCTTTG
```

```
        430        439        448        457        466        475
                    >
CCGCGGCAGA CGCCTGAGG ATG ATG CCC CAG CTG CAG TTC AAA GAT GCC TTT TGG
                    M   M   P   Q   L   Q   F   K   D   A   F   W 484        493        502        511        520        529
TGC AGG GAC TTC ACA GCC CAC ACG GGC TAC GAG GTG CTG CTG CAG CGG CTT CTG
 C   R   D   F   T   A   H   T   G   Y   E   V   L   L   Q   R   L   L 538        547        556        565        574        583
GAT GGC AGG AAG ATG TGC AAA GAC ATG GAG GAG CTA CTG AGG CAG AGG GCC CAG
 D   G   R   K   M   C   K   D   M   E   E   L   L   R   Q   R   A   Q 592        601        610        619        628        637
GCG GAG GAG CGG TAC GGG AAG GAG CTG GTG CAG ATC GCA CGG AAG GCA GGT GGC
 A   E   E   R   Y   G   K   E   L   V   Q   I   A   R   K   A   G   G 646        655        664        673        682        691
CAG ACG GAG ATC AAC TCC CTG AGG GCC TCC TTT GAC TCC TTG AAG CAG CAA ATG
 Q   T   E   I   N   S   L   R   A   S   F   D   S   L   K   Q   Q   M 700        709        718        727        736        745
GAG AAT GTG GGC AGC TCA CAC ATC CAG CTG GCC CTG ACC CTG CGT GAG GAG CTG
 E   N   V   G   S   S   H   I   Q   L   A   L   T   L   R   E   E   L
```

FIG.10A

|     | 754 |     |     | 763 |     |     | 772 |     |     | 781 |     |     | 790 |     |     | 799 |     |
| --- | --- | --- | --- | --- | --- | --- | --- | --- | --- | --- | --- | --- | --- | --- | --- | --- | --- |
| CGG | AGT | CTC | GAG | GAG | TTT | CGT | GAG | AGG | CAG | AAG | GAG | CAG | AGG | AAG | AAG | TAT | GAG |
| R   | S   | L   | E   | E   | F   | R   | E   | R   | Q   | K   | E   | Q   | R   | K   | K   | Y   | E   |

|     | 808 |     |     | 817 |     |     | 826 |     |     | 835 |     |     | 844 |     |     | 853 |     |
| --- | --- | --- | --- | --- | --- | --- | --- | --- | --- | --- | --- | --- | --- | --- | --- | --- | --- |
| GCC | GTC | ATG | GAC | CGG | GTC | CAG | AAG | AGC | AAG | CTG | TCG | CTC | TAC | AAG | AAG | GCC | ATG |
| A   | V   | M   | D   | R   | V   | Q   | K   | S   | K   | L   | S   | L   | Y   | K   | K   | A   | M   |

|     | 862 |     |     | 871 |     |     | 880 |     |     | 889 |     |     | 898 |     |     | 907 |     |
| --- | --- | --- | --- | --- | --- | --- | --- | --- | --- | --- | --- | --- | --- | --- | --- | --- | --- |
| GAG | TCC | AAG | AAG | ACA | TAC | GAG | CAG | AAG | TGC | CGG | GAC | GCG | GAC | GAC | GCG | GAG | CAG |
| E   | S   | K   | K   | T   | Y   | E   | Q   | K   | C   | R   | D   | A   | D   | D   | A   | E   | Q   |

|     | 916 |     |     | 925 |     |     | 934 |     |     | 943 |     |     | 952 |     |     | 961 |     |
| --- | --- | --- | --- | --- | --- | --- | --- | --- | --- | --- | --- | --- | --- | --- | --- | --- | --- |
| GCC | TTC | GAG | CGC | ATT | AGC | GCC | AAC | GGC | CAC | CAG | AAG | CAG | GTG | GAG | AAG | AGT | CAG |
| A   | F   | E   | R   | I   | S   | A   | N   | G   | H   | Q   | K   | Q   | V   | E   | K   | S   | Q   |

|     | 970 |     |     | 979 |     |     | 988 |     |     | 997 |     |     | 1006 |     |     | 1015 |     |
| --- | --- | --- | --- | --- | --- | --- | --- | --- | --- | --- | --- | --- | --- | --- | --- | --- | --- |
| AAC | AAA | GCC | AGG | CAG | TGC | AAG | GAC | TCG | GCC | ACC | GAG | GCA | GAG | CGG | GTA | TAC | AGG |
| N   | K   | A   | R   | Q   | C   | K   | D   | S   | A   | T   | E   | A   | E   | R   | V   | Y   | R   |

|     | 1024 |     |     | 1033 |     |     | 1042 |     |     | 1051 |     |     | 1060 |     |     | 1069 |     |
| --- | --- | --- | --- | --- | --- | --- | --- | --- | --- | --- | --- | --- | --- | --- | --- | --- | --- |
| CAG | AGC | ATT | GCG | CAG | CTG | GAG | AAG | GTC | CGG | GCT | GAG | TGG | GAG | CAG | GAG | CAC | CGG |
| Q   | S   | I   | A   | Q   | L   | E   | K   | V   | R   | A   | E   | W   | E   | Q   | E   | H   | R   |

|     | 1078 |     |     | 1087 |     |     | 1096 |     |     | 1105 |     |     | 1114 |     |     | 1123 |     |
| --- | --- | --- | --- | --- | --- | --- | --- | --- | --- | --- | --- | --- | --- | --- | --- | --- | --- |
| ACC | ACC | TGT | GAG | GCC | TTT | CAG | CTG | CAA | GAG | TTT | GAC | CGG | CTG | ACC | ATT | CTC | CGC |
| T   | T   | C   | E   | A   | F   | Q   | L   | Q   | E   | F   | D   | R   | L   | T   | I   | L   | R   |

|     | 1132 |     |     | 1141 |     |     | 1150 |     |     | 1159 |     |     | 1168 |     |     | 1177 |     |
| --- | --- | --- | --- | --- | --- | --- | --- | --- | --- | --- | --- | --- | --- | --- | --- | --- | --- |
| AAC | GCC | CTG | TGG | GTG | CAC | AGC | AAC | CAG | CTC | TCC | ATG | CAG | TGT | GTC | AAG | GAT | GAT |
| N   | A   | L   | W   | V   | H   | S   | N   | Q   | L   | S   | M   | Q   | C   | V   | K   | D   | D   |

|     | 1186 |     |     | 1195 |     |     | 1204 |     |     | 1213 |     |     | 1222 |     |     | 1231 |     |
| --- | --- | --- | --- | --- | --- | --- | --- | --- | --- | --- | --- | --- | --- | --- | --- | --- | --- |
| GAG | CTC | TAC | GAG | GAA | GTG | CGG | CTG | ACG | CTG | GAA | GGC | TGC | AGC | ATA | GAC | GCC | GAC |
| E   | L   | Y   | E   | E   | V   | R   | L   | T   | L   | E   | G   | C   | S   | I   | D   | A   | D   |

|     | 1240 |     |     | 1249 |     |     | 1258 |     |     | 1267 |     |     | 1276 |     |     | 1285 |     |
| --- | --- | --- | --- | --- | --- | --- | --- | --- | --- | --- | --- | --- | --- | --- | --- | --- | --- |
| ATC | GAC | AGT | TTC | ATC | CAG | GCC | AAG | AGC | ACG | GGC | ACA | GAG | CCC | CCC | GGT | GAG | GTC |
| I   | D   | S   | F   | I   | Q   | A   | K   | S   | T   | G   | T   | E   | P   | P   | G   | E   | V   |

|     | 1294 |     |     | 1303 |     |     | 1312 |     |     | 1321 |     |     | 1330 |     |     | 1339 |     |
| --- | --- | --- | --- | --- | --- | --- | --- | --- | --- | --- | --- | --- | --- | --- | --- | --- | --- |
| CGG | CTT | GCG | GAC | AGC | GCA | GCC | TCT | AGG | TTC | TCT | GGA | CTG | CTG | CAC | GGA | AGT | CCC |
| R   | L   | A   | D   | S   | A   | A   | S   | R   | F   | S   | G   | L   | L   | H   | G   | S   | P   |

|     | 1348 |     |     | 1357 |     |     | 1366 |     |     | 1375 |     |     | 1384 |     |     | 1393 |     |
| --- | --- | --- | --- | --- | --- | --- | --- | --- | --- | --- | --- | --- | --- | --- | --- | --- | --- |
| AAG | ACC | ACT | TCG | TTG | GCA | GCT | TCT | GCT | GCG | TCC | ACA | GAG | ACC | CTG | ACC | CCC | ACC |
| K   | T   | T   | S   | L   | A   | A   | S   | A   | A   | S   | T   | E   | T   | L   | T   | P   | T   |

|     | 1402 |     |     | 1411 |     |     | 1420 |     |     | 1429 |     |     | 1438 |     |     | 1447 |     |
| --- | --- | --- | --- | --- | --- | --- | --- | --- | --- | --- | --- | --- | --- | --- | --- | --- | --- |
| CCC | GAG | CGG | AAT | GAG | GGT | GTC | TAC | ACA | GCC | ATC | GCA | GTG | CAG | GAG | ATA | CAG | GGA |
| P   | E   | R   | N   | E   | G   | V   | Y   | T   | A   | I   | A   | V   | Q   | E   | I   | Q   | G   |

FIG. 10B

|     | 1456 |     |     | 1465 |     |     | 1474 |     |     | 1483 |     |     | 1492 |     |     | 1501 |     |
|-----|------|-----|-----|------|-----|-----|------|-----|-----|------|-----|-----|------|-----|-----|------|-----|
| AAC | CCG  | GCC | TCA | CCA  | GCC | CAG | GAG  | TAC | CGG | GCG  | CTC | TAC | GAT  | TAT | ACA | GCG  | CAG |
| N   | P    | A   | S   | P    | A   | Q   | E    | Y   | R   | A    | L   | Y   | D    | Y   | T   | A    | Q   |

|     | 1510 |     |     | 1519 |     |     | 1528 |     |     | 1537 |     |     | 1546 |     |     | 1555 |     |
|-----|------|-----|-----|------|-----|-----|------|-----|-----|------|-----|-----|------|-----|-----|------|-----|
| AAC | CCA  | GAT | GAG | CTG  | GAC | CTG | TCC  | GCG | GGA | GAC  | ATC | CTG | GAG  | GTG | ATC | CTG  | GAA |
| N   | P    | D   | E   | L    | D   | L   | S    | A   | G   | D    | I   | L   | E    | V   | I   | L    | E   |

|     | 1564 |     |     | 1573 |     |     | 1582 |     |     | 1591 |     |     | 1600 |     |     | 1609 |     |
|-----|------|-----|-----|------|-----|-----|------|-----|-----|------|-----|-----|------|-----|-----|------|-----|
| GGG | GAG  | GAT | GGC | TGG  | TGG | ACT | GTG  | GAG | AGG | AAC  | GGG | CAG | CGT  | GGC | TTC | GTC  | CCT |
| G   | E    | D   | G   | W    | W   | T   | V    | E   | R   | N    | G   | Q   | R    | G   | F   | V    | P   |

|     | 1618 |     |     | 1627 |     |     | 1636 |     |     | 1645 |     |     | 1654 |     |     | 1663 |     |
|-----|------|-----|-----|------|-----|-----|------|-----|-----|------|-----|-----|------|-----|-----|------|-----|
| GGT | TCC  | TAC | CTG | GAG  | AAG | CTT | TGA  | GGA | AGG | GCC  | AGG | AGC | CCC  | TTC | GGA | CCT  | GCC |
| G   | S    | Y   | L   | E    | K   | L   | .    | G   | R   | A    | R   | S   | P    | F   | G   | P    | A   |

|     | 1672 |     |     | 1681 |     |     | 1690 |     |     | 1699 |     |     | 1708 |     |     | 1717 |     |
|-----|------|-----|-----|------|-----|-----|------|-----|-----|------|-----|-----|------|-----|-----|------|-----|
| CTG | CCA  | GTG | GAG | CCA  | GCA | GTG | CCC  | CCA | GCA | CTG  | TCC | CCA | CCT  | TGC | TAG | GGC  | CCA |
| L   | P    | V   | E   | P    | A   | V   | P    | P   | A   | L    | S   | P   | P    | C   | .   | G    | P   |

|     | 1726 |     |     | 1735 |     |     | 1744 |     |     | 1753 |     |     | 1762 |     |     | 1771 |     |
|-----|------|-----|-----|------|-----|-----|------|-----|-----|------|-----|-----|------|-----|-----|------|-----|
| GAA | CCA  | AGC | GTC | CCC  | CAG | CCC | CGA  | GAG | GGA | GCC  | TGT | CGT | CTC  | CCA | GGG | AAT  | AAA |
| E   | P    | S   | V   | P    | Q   | P   | R    | E   | G   | A    | C   | R   | L    | P   | G   | N    | K   |

|     | 1780 |     |     | 1789 |     |     | 1798 |     |
|-----|------|-----|-----|------|-----|-----|------|-----|
| GGA | GTG  | CGT | TCT | GTT  | CTT | GGA | AAA  | AAA | AAA | AA |
| G   | V    | R   | S   | V    | L   | G   | K    | K   | K   |    |

SEQUENCE LISTING

```
<160> NUMBER OF SEQ ID NOS: 28

<210> SEQ ID NO 1
<211> LENGTH: 416
<212> TYPE: PRT
<213> ORGANISM: Homo sapiens

<400> SEQUENCE: 1

Met Met Pro Gln Leu Gln Phe Lys Asp Ala Phe Trp Cys Arg Asp Phe
1               5                   10                  15

Thr Ala His Thr Gly Tyr Glu Val Leu Leu Gln Arg Leu Leu Asp Gly
            20                  25                  30

Arg Lys Met Cys Lys Asp Met Glu Glu Leu Leu Arg Gln Arg Ala Gln
        35                  40                  45

Ala Glu Glu Arg Tyr Gly Lys Glu Leu Val Gln Ile Ala Arg Lys Ala
    50                  55                  60

Gly Gly Gln Thr Glu Ile Asn Ser Leu Arg Ala Ser Phe Asp Ser Leu
65                  70                  75                  80

Lys Gln Gln Met Glu Asn Val Gly Ser Ser His Ile Gln Leu Ala Leu
                85                  90                  95

Thr Leu Arg Glu Glu Leu Arg Ser Leu Glu Glu Phe Arg Glu Arg Gln
            100                 105                 110

Lys Glu Gln Arg Lys Lys Tyr Glu Ala Val Met Asp Arg Val Gln Lys
        115                 120                 125

Ser Lys Leu Ser Leu Tyr Lys Lys Ala Met Glu Ser Lys Lys Thr Tyr
    130                 135                 140

Glu Gln Lys Cys Arg Asp Ala Asp Asp Ala Glu Gln Ala Phe Glu Arg
145                 150                 155                 160
```

-continued

Ile Ser Ala Asn Gly His Gln Lys Gln Val Glu Lys Ser Gln Asn Lys
            165                 170                 175

Ala Arg Gln Cys Lys Asp Ser Ala Thr Glu Ala Glu Arg Val Tyr Arg
        180                 185                 190

Gln Ser Ile Ala Gln Leu Glu Lys Val Arg Ala Glu Trp Glu Gln Glu
    195                 200                 205

His Arg Thr Thr Cys Glu Ala Phe Gln Leu Gln Glu Phe Asp Arg Leu
210                 215                 220

Thr Ile Leu Arg Asn Ala Leu Trp Val His Ser Asn Gln Leu Ser Met
225                 230                 235                 240

Gln Cys Val Lys Asp Asp Glu Leu Tyr Glu Glu Val Arg Leu Thr Leu
            245                 250                 255

Glu Gly Cys Ser Ile Asp Ala Asp Ile Asp Ser Phe Ile Gln Ala Lys
        260                 265                 270

Ser Thr Gly Thr Glu Pro Pro Ala Pro Val Pro Tyr Gln Asn Tyr Tyr
    275                 280                 285

Asp Arg Glu Val Thr Pro Leu Thr Ser Ser Pro Gly Ile Gln Pro Ser
290                 295                 300

Cys Gly Met Ile Lys Arg Phe Ser Gly Leu Leu His Gly Ser Pro Lys
305                 310                 315                 320

Thr Thr Ser Leu Ala Ala Ser Ala Ala Ser Thr Glu Thr Leu Thr Pro
            325                 330                 335

Thr Pro Glu Arg Asn Glu Gly Val Tyr Thr Ala Ile Ala Val Gln Glu
        340                 345                 350

Ile Gln Gly Asn Pro Ala Ser Pro Ala Gln Glu Tyr Arg Ala Leu Tyr
    355                 360                 365

Asp Tyr Thr Ala Gln Asn Pro Asp Glu Leu Asp Leu Ser Ala Gly Asp
370                 375                 380

Ile Leu Glu Val Ile Leu Glu Gly Glu Asp Gly Trp Trp Thr Val Glu
385                 390                 395                 400

Arg Asn Gly Gln Arg Gly Phe Val Pro Gly Ser Tyr Leu Glu Lys Leu
            405                 410                 415

<210> SEQ ID NO 2
<211> LENGTH: 397
<212> TYPE: PRT
<213> ORGANISM: Homo sapiens

<400> SEQUENCE: 2

Met Met Pro Gln Leu Gln Phe Lys Asp Ala Phe Trp Cys Arg Asp Phe
1               5                   10                  15

Thr Ala His Thr Gly Tyr Glu Val Leu Leu Gln Arg Leu Leu Asp Gly
            20                  25                  30

Arg Lys Met Cys Lys Asp Met Glu Glu Leu Leu Arg Gln Arg Ala Gln
        35                  40                  45

Ala Glu Glu Arg Tyr Gly Lys Glu Leu Val Gln Ile Ala Arg Lys Ala
    50                  55                  60

Gly Gly Gln Thr Glu Ile Asn Ser Leu Arg Ala Ser Phe Asp Ser Leu
65                  70                  75                  80

Lys Gln Gln Met Glu Asn Val Gly Ser Ser His Ile Gln Leu Ala Leu
            85                  90                  95

Thr Leu Arg Glu Glu Leu Arg Ser Leu Glu Glu Phe Arg Glu Arg Gln
        100                 105                 110

Lys Glu Gln Arg Lys Lys Tyr Glu Ala Val Met Asp Arg Val Gln Lys
    115                 120                 125

-continued

```
Ser Lys Leu Ser Leu Tyr Lys Lys Ala Met Glu Ser Lys Lys Thr Tyr
    130                 135                 140

Glu Gln Lys Cys Arg Asp Ala Asp Asp Ala Glu Gln Ala Phe Glu Arg
145                 150                 155                 160

Ile Ser Ala Asn Gly His Gln Lys Gln Val Glu Lys Ser Gln Asn Lys
                165                 170                 175

Ala Arg Gln Cys Lys Asp Ser Ala Thr Glu Ala Glu Arg Val Tyr Arg
            180                 185                 190

Gln Ser Ile Ala Gln Leu Glu Lys Val Arg Ala Glu Trp Glu Gln Glu
        195                 200                 205

His Arg Thr Thr Cys Glu Ala Phe Gln Leu Gln Glu Phe Asp Arg Leu
    210                 215                 220

Thr Ile Leu Arg Asn Ala Leu Trp Val His Ser Asn Gln Leu Ser Met
225                 230                 235                 240

Gln Cys Val Lys Asp Asp Glu Leu Tyr Glu Val Arg Leu Thr Leu
                245                 250                 255

Glu Gly Cys Ser Ile Asp Ala Asp Ile Asp Ser Phe Ile Gln Ala Lys
                260                 265                 270

Ser Thr Gly Thr Glu Pro Pro Gly Glu Val Arg Leu Ala Asp Ser Ala
        275                 280                 285

Ala Ser Arg Phe Ser Gly Leu Leu His Gly Ser Pro Lys Thr Thr Ser
    290                 295                 300

Leu Ala Ala Ser Ala Ala Ser Thr Glu Thr Leu Thr Pro Thr Pro Glu
305                 310                 315                 320

Arg Asn Glu Gly Val Tyr Thr Ala Ile Ala Val Gln Glu Ile Gln Gly
                325                 330                 335

Asn Pro Ala Ser Pro Ala Gln Glu Tyr Arg Ala Leu Tyr Asp Tyr Thr
            340                 345                 350

Ala Gln Asn Pro Asp Glu Leu Asp Leu Ser Ala Gly Asp Ile Leu Glu
        355                 360                 365

Val Ile Leu Glu Gly Glu Asp Gly Trp Trp Thr Val Glu Arg Asn Gly
    370                 375                 380

Gln Arg Gly Phe Val Pro Gly Ser Tyr Leu Glu Lys Leu
385                 390                 395
```

<210> SEQ ID NO 3
<211> LENGTH: 166
<212> TYPE: PRT
<213> ORGANISM: Homo sapiens

<400> SEQUENCE: 3

```
Met Asp Arg Val Gln Lys Ser Lys Leu Ser Leu Tyr Lys Lys Ala Met
1               5                   10                  15

Glu Ser Lys Lys Thr Tyr Glu Gln Lys Cys Arg Asp Ala Asp Asp Ala
                20                  25                  30

Glu Gln Ala Phe Glu Arg Ile Ser Ala Asn Gly His Gln Lys Gln Val
            35                  40                  45

Glu Lys Ser Gln Asn Lys Ala Arg Gln Cys Lys Asp Ser Ala Thr Glu
        50                  55                  60

Ala Glu Arg Val Tyr Arg Gln Ser Ile Ala Gln Leu Glu Lys Val Arg
65                  70                  75                  80

Ala Glu Trp Glu Gln Glu His Arg Thr Thr Cys Glu Ala Phe Gln Leu
                85                  90                  95

Gln Glu Phe Asp Arg Leu Thr Ile Leu Arg Asn Ala Leu Trp Val His
```

```
                100              105             110
Ser Asn Gln Leu Ser Met Gln Cys Val Lys Asp Asp Glu Leu Tyr Glu
            115             120             125

Glu Val Arg Leu Thr Leu Glu Gly Cys Ser Ile Asp Ala Asp Ile Asp
    130             135             140

Ser Phe Ile Gln Ala Lys Ser Thr Gly Thr Glu Pro Pro Ala Pro Val
145             150             155             160

Pro Tyr Gln Asn Tyr Tyr
                165

<210> SEQ ID NO 4
<211> LENGTH: 162
<212> TYPE: PRT
<213> ORGANISM: Homo sapiens

<400> SEQUENCE: 4

Ile Glu Glu Leu Tyr Gln Lys Lys Thr Ala Leu Glu Ile Asp Leu Ser
1               5               10              15

Glu Lys Lys Asp Ala Tyr Glu Tyr Ser Cys Asn Lys Leu Asn Ser Tyr
            20              25              30

Met Arg Gln Thr Lys Lys Met Thr Gly Arg Glu Leu Asp Lys Tyr Asn
        35              40              45

Leu Lys Ile Arg Gln Ala Ala Leu Ala Val Lys Lys Met Asp Ala Glu
    50              55              60

Tyr Arg Glu Thr Asn Glu Leu Leu Leu Thr Val Thr Arg Glu Trp Ile
65              70              75              80

Asp Arg Trp Thr Glu Val Cys Asp Ala Phe Gln His Ile Glu Glu Tyr
                85              90              95

Arg Leu Glu Phe Leu Lys Thr Asn Met Trp Ala Tyr Ala Asn Ile Ile
            100             105             110

Ser Thr Ala Cys Val Lys Asp Asp Glu Ser Cys Glu Lys Ile Arg Leu
        115             120             125

Thr Leu Glu Asn Thr Asn Ile Asp Glu Asp Ile Thr Gln Met Ile Gln
    130             135             140

Asn Glu Gly Thr Gly Thr Thr Ile Pro Pro Leu Pro Glu Phe Asn Asp
145             150             155             160

Tyr Phe

<210> SEQ ID NO 5
<211> LENGTH: 57
<212> TYPE: PRT
<213> ORGANISM: Homo sapiens

<400> SEQUENCE: 5

Pro Ala Gln Glu Tyr Arg Ala Leu Tyr Asp Tyr Thr Ala Gln Asn Pro
1               5               10              15

Asp Glu Leu Asp Leu Ser Ala Gly Asp Ile Leu Glu Val Ile Leu Glu
            20              25              30

Gly Glu Asp Gly Trp Trp Thr Val Glu Arg Asn Gly Gln Arg Gly Phe
        35              40              45

Val Pro Gly Ser Tyr Leu Glu Lys Leu
    50              55

<210> SEQ ID NO 6
<211> LENGTH: 62
<212> TYPE: PRT
<213> ORGANISM: Homo sapiens
```

-continued

<400> SEQUENCE: 6

Met Asp Glu Thr Gly Lys Glu Leu Val Leu Ala Leu Tyr Asp Tyr Gln
1               5                   10                  15

Glu Lys Ser Pro Arg Glu Val Thr Met Lys Lys Gly Asp Ile Leu Thr
            20                  25                  30

Leu Leu Asn Ser Thr Asn Lys Asp Trp Trp Lys Val Glu Val Asn Asp
        35                  40                  45

Arg Gln Gly Phe Val Pro Ala Ala Tyr Val Lys Lys Leu Asp
    50                  55                  60

<210> SEQ ID NO 7
<211> LENGTH: 63
<212> TYPE: PRT
<213> ORGANISM: Homo sapiens

<400> SEQUENCE: 7

Pro Thr Asp Asp Glu Thr Gly Lys Glu Leu Val Leu Ala Leu Tyr Asp
1               5                   10                  15

Tyr Gln Glu Lys Ser Pro Arg Glu Val Thr Met Lys Lys Gly Asp Ile
            20                  25                  30

Leu Thr Leu Leu Asn Ser Thr Asn Lys Asp Trp Trp Lys Val Glu Val
        35                  40                  45

Asn Asp Arg Gln Gly Phe Val Pro Ala Ala Tyr Val Lys Lys Leu
    50                  55                  60

<210> SEQ ID NO 8
<211> LENGTH: 60
<212> TYPE: PRT
<213> ORGANISM: Homo sapiens

<400> SEQUENCE: 8

Pro Gly Pro Glu Gln Ala Arg Ala Leu Tyr Asp Phe Ala Ala Glu Asn
1               5                   10                  15

Pro Asp Glu Leu Thr Phe Asn Glu Gly Ala Val Val Thr Val Ile Asn
            20                  25                  30

Lys Ser Asn Pro Asp Trp Trp Glu Gly Glu Leu Asn Gly Gln Arg Gly
        35                  40                  45

Val Phe Pro Ala Ser Tyr Val Glu Leu Ile Pro Arg
    50                  55                  60

<210> SEQ ID NO 9
<211> LENGTH: 52
<212> TYPE: PRT
<213> ORGANISM: Homo sapiens

<400> SEQUENCE: 9

Ala Ile Tyr Asp Tyr Thr Lys Asp Lys Glu Asp Glu Leu Ser Phe Gln
1               5                   10                  15

Glu Gly Ala Ile Ile Tyr Val Ile Lys Lys Asn Asp Asp Gly Trp Tyr
            20                  25                  30

Glu Gly Val Met Asn Gly Val Thr Gly Leu Phe Pro Gly Asn Tyr Val
        35                  40                  45

Glu Ser Ile Met
    50

<210> SEQ ID NO 10
<211> LENGTH: 60
<212> TYPE: PRT

<213> ORGANISM: Homo sapiens

<400> SEQUENCE: 10

```
Ile Ile Leu Gln Thr Tyr Arg Ala Ile Ala Asp Tyr Glu Lys Thr Ser
 1               5                  10                  15
Gly Ser Glu Met Ala Leu Ser Thr Gly Asp Val Val Glu Val Val Glu
            20                  25                  30
Lys Ser Glu Ser Gly Trp Trp Phe Cys Gln Met Lys Ala Lys Arg Gly
        35                  40                  45
Trp Ile Pro Ala Ser Phe Leu Glu Pro Leu Asp Ser
    50                  55                  60
```

<210> SEQ ID NO 11
<211> LENGTH: 74
<212> TYPE: PRT
<213> ORGANISM: Homo sapiens

<400> SEQUENCE: 11

```
Gly Ser Arg Arg Ala Ser Val Gly Ser Met Glu Ala Ile Ala Lys Tyr
 1               5                  10                  15
Asp Phe Lys Ala Thr Ala Asp Asp Glu Leu Ser Phe Lys Arg Gly Asp
            20                  25                  30
Ile Leu Lys Val Leu Asn Glu Glu Cys Asp Gln Asn Trp Tyr Lys Ala
        35                  40                  45
Glu Leu Asn Gly Lys Asp Gly Phe Ile Pro Lys Asn Tyr Ile Glu Met
    50                  55                  60
Lys Pro His Pro Glu Phe Ile Val Thr Asp
65                  70
```

<210> SEQ ID NO 12
<211> LENGTH: 62
<212> TYPE: PRT
<213> ORGANISM: Homo sapiens

<400> SEQUENCE: 12

```
Pro Ile Leu Gly Tyr Val Ile Ala Leu Tyr Asp Tyr Gln Ala Gln Ile
 1               5                  10                  15
Pro Glu Glu Ile Ser Phe Gln Lys Gly Asp Thr Leu Met Val Leu Arg
            20                  25                  30
Thr Gln Glu Asp Gly Trp Trp Asp Gly Glu Ile Ile Asn Val Pro Asn
        35                  40                  45
Ser Lys Arg Gly Leu Phe Pro Ser Asn Phe Val Gln Thr Val
    50                  55                  60
```

<210> SEQ ID NO 13
<211> LENGTH: 60
<212> TYPE: PRT
<213> ORGANISM: Homo sapiens

<400> SEQUENCE: 13

```
Tyr Ala Gly Glu Pro Tyr Val Ala Ile Lys Ala Tyr Thr Ala Val Glu
 1               5                  10                  15
Gly Asp Glu Val Ser Leu Leu Glu Gly Glu Ala Val Glu Val Ile His
            20                  25                  30
Lys Leu Leu Asp Gly Trp Trp Val Ile Arg Lys Asp Asp Val Thr Gly
        35                  40                  45
Tyr Phe Pro Ser Met Tyr Leu Gln Lys Ser Gly Gln
    50                  55                  60
```

-continued

```
<210> SEQ ID NO 14
<211> LENGTH: 79
<212> TYPE: PRT
<213> ORGANISM: Homo sapiens

<400> SEQUENCE: 14

Met Ser Ala Glu Gly Tyr Gln Tyr Arg Ala Leu Tyr Asp Tyr Lys Lys
 1               5                  10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Glu Ile Gly Trp Leu Asn Gly Tyr Asn Glu Thr Thr Gly
    50                  55                  60

Glu Arg Gly Asp Phe Pro Gly Thr Tyr Val Glu Tyr Ile Gly Arg
65                  70                  75

<210> SEQ ID NO 15
<211> LENGTH: 70
<212> TYPE: PRT
<213> ORGANISM: Homo sapiens

<400> SEQUENCE: 15

Pro Pro Pro Pro Pro Gly His Arg Ser Gln Ala Pro Ser His Arg Pro
 1               5                  10                  15

Pro Pro Pro Gly His Arg Val Gln His Gln Pro Gln Lys Arg Pro Pro
            20                  25                  30

Ala Pro Ser Gly Thr Gln Val His Gln Gln Lys Gly Pro Pro Leu Pro
        35                  40                  45

Arg Pro Arg Val Gln Pro Lys Pro Pro His Gly Ala Ala Glu Asn Ser
    50                  55                  60

Leu Ser Pro Ser Ser Asn
65                  70

<210> SEQ ID NO 16
<211> LENGTH: 1858
<212> TYPE: DNA
<213> ORGANISM: Homo sapiens
<220> FEATURE:
<221> NAME/KEY: CDS
<222> LOCATION: (440)...(1687)

<400> SEQUENCE: 16
ctgcgcaggc tcgggctgc  ctgcctgcct gcctgcctgg cccggcccga gctccagcct      60
gcctcttcca ctggccactg cctcccaccc agggctggca tcctgctccc tgccctgggt     120
cccagactgt gtcctccatc accgcagggt cggtgagggg ctgggctgga caccagggcc     180
cgccctccca tcactgagct ccactccttc ctcattttgc tgctgattct agccccaaac     240
aaaacaggtt gagctttttc ctcccctcag aagctcctct ctggctcgtg gctgccttct     300
gagtgttgca gacggcgccg gccgggaagg ggggcctggg ccagccctgc caggactggg     360
acgctgctgc tggcgcctgg ccctccatca ggccagcctg tggcaggaga gtgagctttg     420
ccgcggcaga cgcctgagg atg atg ccc cag ctg cag ttc aaa gat gcc ttt     472
                     Met Met Pro Gln Leu Gln Phe Lys Asp Ala Phe
                      1               5                  10 tgg tgc agg gac ttc aca gcc cac acg ggc tac gag gtg ctg ctg cag     520
Trp Cys Arg Asp Phe Thr Ala His Thr Gly Tyr Glu Val Leu Leu Gln
        15                  20                  25
```

-continued

| | | |
|---|---|---|
| cgg ctt ctg gat ggc agg aag atg tgc aaa gac atg gag gag cta ctg<br>Arg Leu Leu Asp Gly Arg Lys Met Cys Lys Asp Met Glu Glu Leu Leu<br>30                 35                  40 | 568 |
| agg cag agg gcc cag gcg gag gag cgg tac ggg aag gag ctg gtg cag<br>Arg Gln Arg Ala Gln Ala Glu Glu Arg Tyr Gly Lys Glu Leu Val Gln<br>    45                  50                  55 | 616 |
| atc gca cgg aag gca ggt ggc cag acg gag atc aac tcc ctg agg gcc<br>Ile Ala Arg Lys Ala Gly Gly Gln Thr Glu Ile Asn Ser Leu Arg Ala<br>60                  65                  70                  75 | 664 |
| tcc ttt gac tcc ttg aag cag caa atg gag aat gtg ggc agc tca cac<br>Ser Phe Asp Ser Leu Lys Gln Gln Met Glu Asn Val Gly Ser Ser His<br>                80                  85                  90 | 712 |
| atc cag ctg gcc ctg acc ctg cgt gag gag ctg cgg agt ctc gag gag<br>Ile Gln Leu Ala Leu Thr Leu Arg Glu Glu Leu Arg Ser Leu Glu Glu<br>        95                 100                 105 | 760 |
| ttt cgt gag agg cag aag gag cag agg aag aag tat gag gcc gtc atg<br>Phe Arg Glu Arg Gln Lys Glu Gln Arg Lys Lys Tyr Glu Ala Val Met<br>            110                 115                 120 | 808 |
| gac cgg gtc cag aag agc aag ctg tcg ctc tac aag aag gcc atg gag<br>Asp Arg Val Gln Lys Ser Lys Leu Ser Leu Tyr Lys Lys Ala Met Glu<br>125                 130                 135 | 856 |
| tcc aag aag aca tac gag cag aag tgc cgg gac gcg gac gac gcg gag<br>Ser Lys Lys Thr Tyr Glu Gln Lys Cys Arg Asp Ala Asp Asp Ala Glu<br>140                 145                 150                 155 | 904 |
| cag gcc ttc gag cgc att agc gcc aac ggc cac cag aag cag gtg gag<br>Gln Ala Phe Glu Arg Ile Ser Ala Asn Gly His Gln Lys Gln Val Glu<br>                160                 165                 170 | 952 |
| aag agt cag aac aaa gcc agg cag tgc aag gac tcg gcc acc gag gca<br>Lys Ser Gln Asn Lys Ala Arg Gln Cys Lys Asp Ser Ala Thr Glu Ala<br>        175                 180                 185 | 1000 |
| gag cgg gta tac agg cag agc att gcg cag ctg gag aag gtc cgg gct<br>Glu Arg Val Tyr Arg Gln Ser Ile Ala Gln Leu Glu Lys Val Arg Ala<br>            190                 195                 200 | 1048 |
| gag tgg gag cag gag cac cgg acc acc tgt gag gcc ttt cag ctg caa<br>Glu Trp Glu Gln Glu His Arg Thr Thr Cys Glu Ala Phe Gln Leu Gln<br>205                 210                 215 | 1096 |
| gag ttt gac cgg ctg acc att ctc cgc aac gcc ctg tgg gtg cac agc<br>Glu Phe Asp Arg Leu Thr Ile Leu Arg Asn Ala Leu Trp Val His Ser<br>220                 225                 230                 235 | 1144 |
| aac cag ctc tcc atg cag tgt gtc aag gat gat gag ctc tac gag gaa<br>Asn Gln Leu Ser Met Gln Cys Val Lys Asp Asp Glu Leu Tyr Glu Glu<br>                240                 245                 250 | 1192 |
| gtg cgg ctg acg ctg gaa ggc tgc agc ata gac gcc gac atc gac agt<br>Val Arg Leu Thr Leu Glu Gly Cys Ser Ile Asp Ala Asp Ile Asp Ser<br>        255                 260                 265 | 1240 |
| ttc atc cag gcc aag agc acg ggc aca gag ccc ccg gct ccg gtg ccc<br>Phe Ile Gln Ala Lys Ser Thr Gly Thr Glu Pro Pro Ala Pro Val Pro<br>            270                 275                 280 | 1288 |
| tac cag aac tat tac gat cgg gag gtc acc ccg ctg acc agc agc cct<br>Tyr Gln Asn Tyr Tyr Asp Arg Glu Val Thr Pro Leu Thr Ser Ser Pro<br>285                 290                 295 | 1336 |
| ggc ata cag ccg tcc tgc ggc atg ata aag agg ttc tct gga ctg ctg<br>Gly Ile Gln Pro Ser Cys Gly Met Ile Lys Arg Phe Ser Gly Leu Leu<br>300                 305                 310                 315 | 1384 |
| cac gga agt ccc aag acc act tcg ttg gca gct tct gct gcg tcc aca<br>His Gly Ser Pro Lys Thr Thr Ser Leu Ala Ala Ser Ala Ala Ser Thr<br>                320                 325                 330 | 1432 |
| gag acc ctg acc ccc acc ccc gag cgg aat gag ggt gtc tac aca gcc<br>Glu Thr Leu Thr Pro Thr Pro Glu Arg Asn Glu Gly Val Tyr Thr Ala<br>        335                 340                 345 | 1480 |

```
atc gca gtg cag gag ata cag gga aac ccg gcc tca cca gcc cag gag      1528
Ile Ala Val Gln Glu Ile Gln Gly Asn Pro Ala Ser Pro Ala Gln Glu
            350                 355                 360 tac cgg gcg ctc tac gat tat aca gcg cag aac cca gat gag ctg gac      1576
Tyr Arg Ala Leu Tyr Asp Tyr Thr Ala Gln Asn Pro Asp Glu Leu Asp
365                 370                 375 ctg tcc gcg gga gac atc ctg gag gtg atc ctg gaa ggg gag gat ggc      1624
Leu Ser Ala Gly Asp Ile Leu Glu Val Ile Leu Glu Gly Glu Asp Gly
380                 385                 390                 395 tgg tgg act gtg gag agg aac ggg cag cgt ggc ttc gtc cct ggt tcc      1672
Trp Trp Thr Val Glu Arg Asn Gly Gln Arg Gly Phe Val Pro Gly Ser
                400                 405                 410 tac ctg gag aag ctt tgaggaaggg ccaggagccc cttcggacct gccctgccag      1727
Tyr Leu Glu Lys Leu
            415 tggagccagc agtgccccca gcactgtccc caccttgcta gggcccagaa ccaagcgtcc    1787 cccagccccg agagggagcc tgtcgtctcc cagggaataa aggagtgcgt tctgttctaa    1847 aaaaaaaaaa a                                                          1858

<210> SEQ ID NO 17
<211> LENGTH: 416
<212> TYPE: PRT
<213> ORGANISM: Homo sapiens

<400> SEQUENCE: 17

Met Met Pro Gln Leu Gln Phe Lys Asp Ala Phe Trp Cys Arg Asp Phe
1               5                   10                  15

Thr Ala His Thr Gly Tyr Glu Val Leu Leu Gln Arg Leu Leu Asp Gly
            20                  25                  30

Arg Lys Met Cys Lys Asp Met Glu Glu Leu Leu Arg Gln Arg Ala Gln
        35                  40                  45

Ala Glu Glu Arg Tyr Gly Lys Glu Leu Val Gln Ile Ala Arg Lys Ala
    50                  55                  60

Gly Gly Gln Thr Glu Ile Asn Ser Leu Arg Ala Ser Phe Asp Ser Leu
65                  70                  75                  80

Lys Gln Gln Met Glu Asn Val Gly Ser Ser His Ile Gln Leu Ala Leu
                85                  90                  95

Thr Leu Arg Glu Glu Leu Arg Ser Leu Glu Glu Phe Arg Glu Arg Gln
            100                 105                 110

Lys Glu Gln Arg Lys Lys Tyr Glu Ala Val Met Asp Arg Val Gln Lys
        115                 120                 125

Ser Lys Leu Ser Leu Tyr Lys Lys Ala Met Glu Ser Lys Lys Thr Tyr
    130                 135                 140

Glu Gln Lys Cys Arg Asp Ala Asp Ala Glu Gln Ala Phe Glu Arg
145                 150                 155                 160

Ile Ser Ala Asn Gly His Gln Lys Gln Val Glu Lys Ser Gln Asn Lys
                165                 170                 175

Ala Arg Gln Cys Lys Asp Ser Ala Thr Glu Ala Glu Arg Val Tyr Arg
            180                 185                 190

Gln Ser Ile Ala Gln Leu Glu Lys Val Arg Ala Glu Trp Glu Gln Glu
        195                 200                 205

His Arg Thr Thr Cys Glu Ala Phe Gln Leu Gln Glu Phe Asp Arg Leu
    210                 215                 220

Thr Ile Leu Arg Asn Ala Leu Trp Val His Ser Asn Gln Leu Ser Met
225                 230                 235                 240
```

```
Gln Cys Val Lys Asp Asp Glu Leu Tyr Glu Val Arg Leu Thr Leu
                245                 250                 255
Glu Gly Cys Ser Ile Asp Ala Asp Ile Asp Ser Phe Ile Gln Ala Lys
            260                 265                 270
Ser Thr Gly Thr Glu Pro Pro Ala Pro Val Pro Tyr Gln Asn Tyr Tyr
        275                 280                 285
Asp Arg Glu Val Thr Pro Leu Thr Ser Ser Pro Gly Ile Gln Pro Ser
    290                 295                 300
Cys Gly Met Ile Lys Arg Phe Ser Gly Leu Leu His Gly Ser Pro Lys
305                 310                 315                 320
Thr Thr Ser Leu Ala Ala Ser Ala Ala Ser Thr Glu Thr Leu Thr Pro
                325                 330                 335
Thr Pro Glu Arg Asn Glu Gly Val Tyr Thr Ala Ile Ala Val Gln Glu
            340                 345                 350
Ile Gln Gly Asn Pro Ala Ser Pro Ala Gln Glu Tyr Arg Ala Leu Tyr
        355                 360                 365
Asp Tyr Thr Ala Gln Asn Pro Asp Glu Leu Asp Leu Ser Ala Gly Asp
    370                 375                 380
Ile Leu Glu Val Ile Leu Glu Gly Glu Asp Gly Trp Trp Thr Val Glu
385                 390                 395                 400
Arg Asn Gly Gln Arg Gly Phe Val Pro Gly Ser Tyr Leu Glu Lys Leu
                405                 410                 415

<210> SEQ ID NO 18
<211> LENGTH: 1803
<212> TYPE: DNA
<213> ORGANISM: Homo sapiens
<220> FEATURE:
<221> NAME/KEY: CDS
<222> LOCATION: (440)...(1630)

<400> SEQUENCE: 18
ctgcgcaggc ctcgggctgc ctgcctgcct gcctgcctgg cccggcccga gctccagcct      60
gcctcttcca ctggccactg cctcccaccc agggctggca tcctgctccc tgccctgggt     120
cccagactgt gtcctccatc accgcagggt cggtgagggg ctgggctgga caccagggcc     180
cgccctccca tcactgagct ccactccttc ctcattttgc tgctgattct agccccaaac     240
aaaacaggtt gagcttttc ctcccctcag aagctcctct ctggctcgtg gctgccttct     300
gagtgttgca gacggcgccg gccgggaagg gggcctgggg ccagccctgc caggactggg     360
acgctgctgc tggcgcctgg ccctccatca ggccagcctg tggcaggaga gtgagctttg     420
ccgcggcaga cgcctgagg atg atg ccc cag ctg cag ttc aaa gat gcc ttt      472
                      Met Met Pro Gln Leu Gln Phe Lys Asp Ala Phe
                        1               5                  10 tgg tgc agg gac ttc aca gcc cac acg ggc tac gag gtg ctg ctg cag      520
Trp Cys Arg Asp Phe Thr Ala His Thr Gly Tyr Glu Val Leu Leu Gln
            15                  20                  25 cgg ctt ctg gat ggc agg aag atg tgc aaa gac atg gag gag cta ctg      568
Arg Leu Leu Asp Gly Arg Lys Met Cys Lys Asp Met Glu Glu Leu Leu
        30                  35                  40 agg cag agg gcc cag gcg gag gag cgg tac ggg aag gag ctg gtg cag      616
Arg Gln Arg Ala Gln Ala Glu Glu Arg Tyr Gly Lys Glu Leu Val Gln
    45                  50                  55 atc gca cgg aag gca ggt ggc cag acg gag atc aac tcc ctg agg gcc      664
Ile Ala Arg Lys Ala Gly Gly Gln Thr Glu Ile Asn Ser Leu Arg Ala
60                  65                  70                  75
```

-continued

| | |
|---|---|
| tcc ttt gac tcc ttg aag cag caa atg gag aat gtg ggc agc tca cac<br>Ser Phe Asp Ser Leu Lys Gln Gln Met Glu Asn Val Gly Ser Ser His<br>80                         85                        90 | 712 |
| atc cag ctg gcc ctg acc ctg cgt gag gag ctg cgg agt ctc gag gag<br>Ile Gln Leu Ala Leu Thr Leu Arg Glu Glu Leu Arg Ser Leu Glu Glu<br>95                        100                      105 | 760 |
| ttt cgt gag agg cag aag gag cag agg aag aag tat gag gcc gtc atg<br>Phe Arg Glu Arg Gln Lys Glu Gln Arg Lys Lys Tyr Glu Ala Val Met<br>110                     115                   120 | 808 |
| gac cgg gtc cag aag agc aag ctg tcg ctc tac aag aag gcc atg gag<br>Asp Arg Val Gln Lys Ser Lys Leu Ser Leu Tyr Lys Lys Ala Met Glu<br>125                     130                   135 | 856 |
| tcc aag aag aca tac gag cag aag tgc cgg gac gcg gac gac gcg gag<br>Ser Lys Lys Thr Tyr Glu Gln Lys Cys Arg Asp Ala Asp Asp Ala Glu<br>140                     145                   150                   155 | 904 |
| cag gcc ttc gag cgc att agc gcc aac ggc cac cag aag cag gtg gag<br>Gln Ala Phe Glu Arg Ile Ser Ala Asn Gly His Gln Lys Gln Val Glu<br>160                     165                   170 | 952 |
| aag agt cag aac aaa gcc agg cag tgc aag gac tcg gcc acc gag gca<br>Lys Ser Gln Asn Lys Ala Arg Gln Cys Lys Asp Ser Ala Thr Glu Ala<br>175                     180                   185 | 1000 |
| gag cgg gta tac agg cag agc att gcg cag ctg gag aag gtc cgg gct<br>Glu Arg Val Tyr Arg Gln Ser Ile Ala Gln Leu Glu Lys Val Arg Ala<br>190                     195                   200 | 1048 |
| gag tgg gag cag gag cac cgg acc acc tgt gag gcc ttt cag ctg caa<br>Glu Trp Glu Gln Glu His Arg Thr Thr Cys Glu Ala Phe Gln Leu Gln<br>205                     210                   215 | 1096 |
| gag ttt gac cgg ctg acc att ctc cgc aac gcc ctg tgg gtg cac agc<br>Glu Phe Asp Arg Leu Thr Ile Leu Arg Asn Ala Leu Trp Val His Ser<br>220                     225                   230                   235 | 1144 |
| aac cag ctc tcc atg cag tgt gtc aag gat gat gag ctc tac gag gaa<br>Asn Gln Leu Ser Met Gln Cys Val Lys Asp Asp Glu Leu Tyr Glu Glu<br>240                     245                   250 | 1192 |
| gtg cgg ctg acg ctg gaa ggc tgc agc ata gac gcc gac atc gac agt<br>Val Arg Leu Thr Leu Glu Gly Cys Ser Ile Asp Ala Asp Ile Asp Ser<br>255                     260                   265 | 1240 |
| ttc atc cag gcc aag agc acg ggc aca gag ccc ccc ggt gag gtc cgg<br>Phe Ile Gln Ala Lys Ser Thr Gly Thr Glu Pro Pro Gly Glu Val Arg<br>270                     275                   280 | 1288 |
| ctt gcg gac agc gca gcc tct agg ttc tct gga ctg ctg cac gga agt<br>Leu Ala Asp Ser Ala Ala Ser Arg Phe Ser Gly Leu Leu His Gly Ser<br>285                     290                   295 | 1336 |
| ccc aag acc act tcg ttg gca gct tct gct gcg tcc aca gag acc ctg<br>Pro Lys Thr Thr Ser Leu Ala Ala Ser Ala Ala Ser Thr Glu Thr Leu<br>300                     305                   310                   315 | 1384 |
| acc ccc acc ccc gag cgg aat gag ggt gtc tac aca gcc atc gca gtg<br>Thr Pro Thr Pro Glu Arg Asn Glu Gly Val Tyr Thr Ala Ile Ala Val<br>320                     325                   330 | 1432 |
| cag gag ata cag gga aac ccg gcc tca cca gcc cag gag tac cgg gcg<br>Gln Glu Ile Gln Gly Asn Pro Ala Ser Pro Ala Gln Glu Tyr Arg Ala<br>335                     340                   345 | 1480 |
| ctc tac gat tat aca gcg cag aac cca gat gag ctg gac ctg tcc gcg<br>Leu Tyr Asp Tyr Thr Ala Gln Asn Pro Asp Glu Leu Asp Leu Ser Ala<br>350                     355                   360 | 1528 |
| gga gac atc ctg gag gtg atc ctg gaa ggg gag gat ggc tgg tgg act<br>Gly Asp Ile Leu Glu Val Ile Leu Glu Gly Glu Asp Gly Trp Trp Thr<br>365                     370                   375 | 1576 |
| gtg gag agg aac ggg cag cgt ggc ttc gtc cct ggt tcc tac ctg gag<br>Val Glu Arg Asn Gly Gln Arg Gly Phe Val Pro Gly Ser Tyr Leu Glu<br>380                     385                   390                   395 | 1624 |

-continued

```
aag ctt tgaggaaggg ccaggagccc cttcggacct gccctgccag tggagccagc    1680
Lys Leu agtgccccca gcactgtccc caccttgcta gggcccagaa ccaagcgtcc cccagccccg    1740
agagggagcc tgtcgtctcc cagggaataa aggagtgcgt tctgttcttg gaaaaaaaaa    1800
aaa                                                                 1803
```

<210> SEQ ID NO 19
<211> LENGTH: 397
<212> TYPE: PRT
<213> ORGANISM: Homo sapiens

<400> SEQUENCE: 19

```
Met Met Pro Gln Leu Gln Phe Lys Asp Ala Phe Trp Cys Arg Asp Phe
  1               5                  10                  15

Thr Ala His Thr Gly Tyr Glu Val Leu Leu Gln Arg Leu Leu Asp Gly
             20                  25                  30

Arg Lys Met Cys Lys Asp Met Glu Glu Leu Leu Arg Gln Arg Ala Gln
         35                  40                  45

Ala Glu Glu Arg Tyr Gly Lys Glu Leu Val Gln Ile Ala Arg Lys Ala
     50                  55                  60

Gly Gly Gln Thr Glu Ile Asn Ser Leu Arg Ala Ser Phe Asp Ser Leu
 65                  70                  75                  80

Lys Gln Gln Met Glu Asn Val Gly Ser Ser His Ile Gln Leu Ala Leu
                 85                  90                  95

Thr Leu Arg Glu Glu Leu Arg Ser Leu Glu Glu Phe Arg Glu Arg Gln
            100                 105                 110

Lys Glu Gln Arg Lys Lys Tyr Glu Ala Val Met Asp Arg Val Gln Lys
        115                 120                 125

Ser Lys Leu Ser Leu Tyr Lys Lys Ala Met Glu Ser Lys Lys Thr Tyr
    130                 135                 140

Glu Gln Lys Cys Arg Asp Ala Asp Asp Ala Glu Gln Ala Phe Glu Arg
145                 150                 155                 160

Ile Ser Ala Asn Gly His Gln Lys Gln Val Glu Lys Ser Gln Asn Lys
                165                 170                 175

Ala Arg Gln Cys Lys Asp Ser Ala Thr Glu Ala Glu Arg Val Tyr Arg
            180                 185                 190

Gln Ser Ile Ala Gln Leu Glu Lys Val Arg Ala Glu Trp Glu Gln Glu
        195                 200                 205

His Arg Thr Thr Cys Glu Ala Phe Gln Leu Gln Glu Phe Asp Arg Leu
    210                 215                 220

Thr Ile Leu Arg Asn Ala Leu Trp Val His Ser Asn Gln Leu Ser Met
225                 230                 235                 240

Gln Cys Val Lys Asp Asp Glu Leu Tyr Glu Glu Val Arg Leu Thr Leu
                245                 250                 255

Glu Gly Cys Ser Ile Asp Ala Asp Ile Asp Ser Phe Ile Gln Ala Lys
            260                 265                 270

Ser Thr Gly Thr Glu Pro Pro Gly Glu Val Arg Leu Ala Asp Ser Ala
        275                 280                 285

Ala Ser Arg Phe Ser Gly Leu Leu His Gly Ser Pro Lys Thr Thr Ser
    290                 295                 300

Leu Ala Ala Ser Ala Ala Ser Thr Glu Thr Leu Thr Pro Thr Pro Glu
305                 310                 315                 320

Arg Asn Glu Gly Val Tyr Thr Ala Ile Ala Val Gln Glu Ile Gln Gly
```

```
                  325                 330                 335
Asn Pro Ala Ser Pro Ala Gln Glu Tyr Arg Ala Leu Tyr Asp Tyr Thr
                340                 345                 350

Ala Gln Asn Pro Asp Glu Leu Asp Leu Ser Ala Gly Asp Ile Leu Glu
            355                 360                 365

Val Ile Leu Glu Gly Gly Asp Gly Trp Trp Thr Val Glu Arg Asn Gly
        370                 375                 380

Gln Arg Gly Phe Val Pro Gly Ser Tyr Leu Glu Lys Leu
385                 390                 395
```

<210> SEQ ID NO 20
<211> LENGTH: 4
<212> TYPE: PRT
<213> ORGANISM: Homo sapiens
<220> FEATURE:
<223> OTHER INFORMATION: polypeptide

<400> SEQUENCE: 20

```
Pro Pro Ala Pro
 1
```

<210> SEQ ID NO 21
<211> LENGTH: 6
<212> TYPE: PRT
<213> ORGANISM: Homo sapiens
<220> FEATURE:
<223> OTHER INFORMATION: polypeptide

<400> SEQUENCE: 21

```
Pro Pro Pro Gly His Arg
 1               5
```

<210> SEQ ID NO 22
<211> LENGTH: 5
<212> TYPE: PRT
<213> ORGANISM: Homo sapiens
<220> FEATURE:
<223> OTHER INFORMATION: polypeptide

<400> SEQUENCE: 22

```
Pro Pro Gly His Arg
 1               5
```

<210> SEQ ID NO 23
<211> LENGTH: 5
<212> TYPE: PRT
<213> ORGANISM: Homo sapiens
<220> FEATURE:
<223> OTHER INFORMATION: polypeptide

<400> SEQUENCE: 23

```
Gly Gly Gly Gly Ser
 1               5
```

<210> SEQ ID NO 24
<211> LENGTH: 5
<212> TYPE: PRT
<213> ORGANISM: Homo sapiens
<220> FEATURE:
<223> OTHER INFORMATION: polypeptide

<400> SEQUENCE: 24

```
Gly Phe Cys Cys Cys
 1               5
```

```
<210> SEQ ID NO 25
<211> LENGTH: 4
<212> TYPE: PRT
<213> ORGANISM: Homo sapiens
<220> FEATURE:
<223> OTHER INFORMATION: polypeptide

<400> SEQUENCE: 25

Pro Pro Leu Pro
 1

<210> SEQ ID NO 26
<211> LENGTH: 4
<212> TYPE: PRT
<213> ORGANISM: Homo sapiens
<220> FEATURE:
<223> OTHER INFORMATION: polypeptide
<221> NAME/KEY: VARIANT
<222> LOCATION: 2, 3
<223> OTHER INFORMATION: Xaa = Any Amino Acid

<400> SEQUENCE: 26

Pro Xaa Xaa Pro
 1

<210> SEQ ID NO 27
<211> LENGTH: 7
<212> TYPE: PRT
<213> ORGANISM: Homo sapiens
<220> FEATURE:
<223> OTHER INFORMATION: polypeptide
<221> NAME/KEY: VARIANT
<222> LOCATION: 2, 3, 5, 6
<223> OTHER INFORMATION: Xaa = Any Amino Acid

<400> SEQUENCE: 27

Arg Xaa Xaa Pro Xaa Xaa Pro
 1               5

<210> SEQ ID NO 28
<211> LENGTH: 6
<212> TYPE: PRT
<213> ORGANISM: Homo sapiens
<220> FEATURE:
<223> OTHER INFORMATION: polypeptide
<221> NAME/KEY: VARIANT
<222> LOCATION: 2, 3, 5
<223> OTHER INFORMATION: Xaa = Any Amino Acid

<400> SEQUENCE: 28

Pro Xaa Xaa Pro Xaa Arg
 1               5
```

CLONING AND CHARACTERIZATION OF A CDC15-LIKE ADAPTOR PROTEIN (CD2BP1)

GOVERNMENT SUPPORT

The invention was supported, in whole or in part, by grant AI21226 from the National Institutes of Health. The Government has certain rights in the invention.

BACKGROUND OF THE INVENTION

The human CD2 molecule is found on virtually all T cells and thymocytes as well as NK cells and binds to the surface glycoprotein CD58 which is present on many cell types including antigen presenting cells (APCs) (Bierer et al., 1989; Krensky et al., 1983; Moingeon et al., 1989a; Sanchez-Madrid et al., 1982; Selvaraj et al., 1987; Springer, 1990). CD2 promotes the initial stageslof T cell contact with a cognate partner such as an APC even prior to T cell receptor (TCR) recognition of a peptide antigen bound to a major histocompatibility complex (MHC) molecule (Koyasu et al., 1990; Moingeon et al., 1989a; Moingeon et al., 1989b). This makes the antigen recognition process much more efficient, by increasing the dwell time when opposing cellular plasma membranes are in contact and thus, offering a greater opportunity for an individual TCR to locate an MHC molecule complexed with a specific antigenic peptide. While it is known that the monomeric affinity of the CD2-CD58 interaction is low (Kd=$\mu$M), coligation of CD2 and CD58 molecules on opposing cells within a conjugate pair induces CD2 redistribution to the region of cell-cell contact, resulting in a substantial avidity boost (Arulanandam et al., 1993a; Koyasu et al., 1990; Li et al., 1996; Recny et al., 1990; Sayre et al., 1989).

CD2 functions as a signaling molecule in a number of important settings. First, CD58 interaction with CD2 augments IL-12 responsiveness of activated T cells with regard to proliferation and IFN-$\gamma$ production (Gollob et al., 1996; Gollob et al., 1995; Wingren et al., 1993). Second, the CD2-CD58 interaction has been reported to reverse T cell anergy (Boussiotis et al., 1994). Third, the CD2 cytoplasmic tail is required for optimal CD2 augmentation of antigen-triggered T cell responses (Hahn and Bierer, 1993; Moingeon et al., 1989b). Hence, in addition to augmenting antigen recognition via its role in adhesion, CD2 facilitates antigen recognition via signal transduction. Consistent with this notion is the fact that T cell proliferation to suboptimal concentrations of anti-CD3 mAb is augmented by CD2 crosslinking through addition of specific pairs of anti-CD2 mAbs (Bierer et al., 1988; Yang et al., 1986). Furthermore, certain pairs of anti-CD2 mAbs can stimulate calcium flux, IL-2 production and cytolytic activity in and of themselves (Meuer et al., 1984; Siliciano et al., 1985).

The molecular basis of CD2-mediated signal transduction is essentially unknown. Truncation and mutation of the CD2 cytoplasmic tail indicate that it is involved in the T cell activation process (Bierer et al., 1988; Chang et al., 1989; Hahn and Bierer, 1993). However, there is no requirement for the CD2 cytoplasmic tail in CD2-mediated cell adhesion and ligand (CD58)-induced CD2 reorganization which occurs subsequent to T cell-APC conjugate formation (Koyasu et al., 1990; Li et al., 1996). A cytoplasmic tail deletion mutant of CD2 lacking the carboxy terminal 92 aa is still capable of relocalizing to the area of cell-cell interaction (Li et al., 1996). These studies do not rule out the possibility that the CD2 cytoplasmic tail is involved in the subsequent regulation of the adhesion complex. CD2-CD58 driven conjugate formation between T lymphocytes and APCs facilitates TCR-mediated antigen recognition of peptide/MHC ligands and subsequently, the attendant downstream cellular activation events. For effective T lymphocyte function, the nature and duration of these cellular events require tight regulation; however, the mechanisms regulating those processes are yet to be elucidated. Moreover, the lack of protein kinase or phosphatase domains or defined signaling motifs within the cytoplasmic tail has complicated the effort to understand the basis for CD2 signaling.

SUMMARY OF THE INVENTION

This invention pertains to an isolated CD2BP1 protein, or an active derivative or fragment thereof having CD2BP1 protein activity. In particular embodiments, the CD2BP1 protein is a derivative possessing substantial sequence identity with the endogenous CD2BP1 protein; in other embodiments, the CD2BP1 protein is the long isoform, CD2BP1L protein (SEQ ID NO:1) or the short isoform, CD2BP1S protein (SEQ ID NO:2). The CD2BP1 protein is isolated, that is, purified to homogeneity or is substantially free of other proteins.

The invention also pertains to an isolated nucleic acid molecule which encodes CD2BP1 protein, or an active derivative or fragment thereof having CD2BP1 protein activity. In another embodiment, the isolated nucleic acid molecule encodes a derivative of CD2BP1 protein possessing substantial sequence identity with the endogenous CD2BP1 protein. In particular embodiments, the isolated nucleic acid molecule encodes a CD2BP1 protein with the same amino acid sequence as endogenous CD2BP1 protein (e.g., CD2BP1L protein or CD2BP1S protein). In another embodiment, the isolated nucleic acid molecule has the same nucleotide sequence as the endogenous gene encoding CD2BP1 protein.

The invention also relates to DNA constructs comprising the nucleic acid molecules described herein operatively linked to a regulatory sequence; to recombinant host cells, such as bacterial cells, fungal cells, plant cells, insect cells and mammalian cells, comprising the nucleic acid molecules described herein operatively linked to a regulatory sequence; and to methods for preparing CD2BP1 protein, by culturing such recombinant host cells. The invention also pertains to an antibody, or an antigen-binding fragment thereof, which selectively binds to CD2BP1 protein or an active derivative or fragment thereof; in a particular embodiment, the antibody is a monoclonal antibody. The invention also relates to a method for assaying for the presence of a CD2BP1 protein in a cell, e.g., in a tissue sample, by contacting the cell with an antibody which specifically binds to CD2BP1 protein.

The present invention also relates to an assay for identifying agents which modulate (inhibit or enhance) the activity of CD2BP1 protein. For example, a cell or fraction thereof containing CD2BP1 protein, or an active fragment or derivative thereof, can be contacted with an agent to be tested, and the level of CD2BP1 protein activity can be assessed. Agents identified by this assay are also included in the invention, as are methods of modulating (inhibiting or enhancing) the activity of CD2BP1 protein by contacting the protein with agents that inhibit or enhance the activity of the protein.

The invention further relates to methods of identifying agents which modulate signal transduction or cell adhesion, by identifying modulation of CD2BP1 protein activity; modulation of CD2BP1 protein activity is indicative of an agent that modulates signal transduction or cell adhesion. Methods of modulating signal transduction or cell adhesion, by contacting CD2BP1 protein with agents that modulate CD2BP1 protein activity, are also included in the invention. The invention additionally relates to methods of targeting proteins such as kinases or phosphatases to a CD2 molecule in a cell, by linking the protein to be targeted with CD2BP1 protein.

BRIEF DESCRIPTION OF THE DRAWINGS

FIG. 3 depicts the amino acid sequence deduced from cDNA for CD2BP1L (SEQ ID NO:1) and CD2BP1S (SEQ ID NO:2). A portion (amino acids 123–288 of CD2BP1L, 123–286 of CD2BP1S) of the amino acid sequence that is homologous to cdc15 is boxed, as is a portion (amino acids 360–416 of CD2BP1L, amino acids 341–397 of CD2BP1S) that contains an SH3 domain. PEST rich regions (proline, glutamic acid, serine and threonine) are underlined (in CD2BP1L, amino acids 320–340; in CD2BP1S, two PEST sequences, amino acids 272–283 and 301–321).

FIG. 4 depicts amino acid homology between amino acids 123–288 of CD2BP1L (SEQ ID NO:3) and *S. pombe* cdc15 (SEQ ID NO:4).

FIG. 5 depicts amino acid homology among SH3 domains of CD2BP1 (SEQ ID NO:5), chicken spectrin α-chain (spct) (SEQ ID NO:6); human α-fodrin (afod) (SEQ ID NO:7); *Acanthamoeba castellanii* myosin IC heavy chain (myosinHC) (SEQ ID NO:8); human abl interactor 2 protein (ablint) (SEQ ID NO:9); human neutrophil cytosol factor 2, SH3 domain A (cytoFa) (SEQ ID NO:10) and SH3 domain B (cytoFb) (SEQ ID NO:13); mouse Grb2 protein (grb2) (SEQ ID NO:11); fission yeast cell division control protein (cdc15) (SEQ ID NO:12); and human phosphatidylinositol 3-kinase (PI3K) (SEQ ID NO:14).

FIGS. 9A–9C depict a nucleotide sequence (SEQ ID NO:16) encoding CD2BP1L (SEQ ID NO:17).

FIGS. 10A–C depict a nucleotide sequence (SEQ ID NO:18) encoding CD2BP1S (SEQ ID NO:19).

Figure 1:
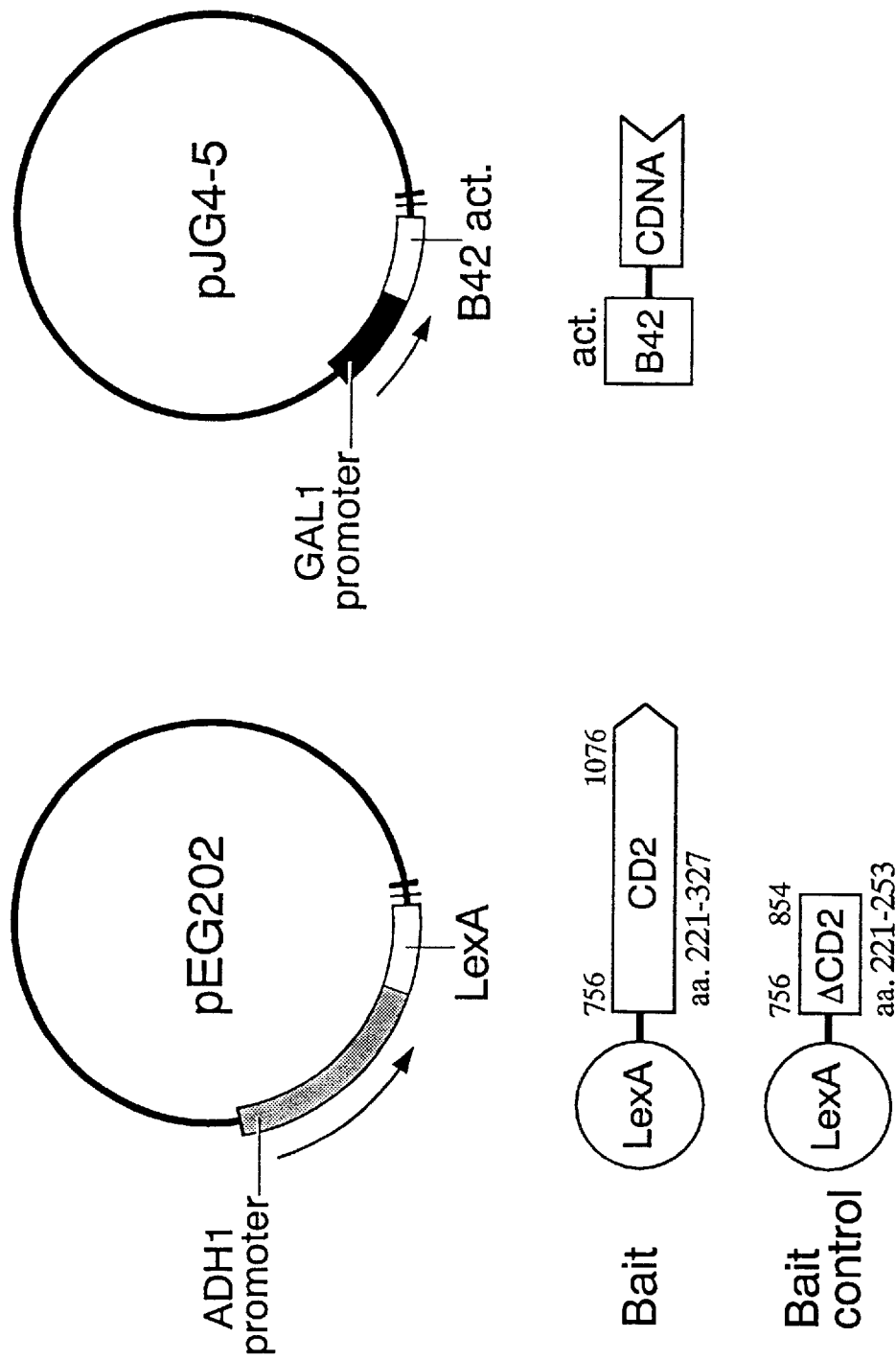
FIG. 1 is a schematic representation of the plasmids, bait and bait control constructs used in a yeast two-hybrid screening system to identify proteins interacting with the CD2 cytoplasmic tail.

The foregoing and other objects, features and advantages of the invention will be apparent from the following more particular description of preferred embodiments of the invention, as illustrated in the accompanying drawings.

DETAILED DESCRIPTION OF THE INVENTION

As described herein, a yeast two-hybrid system was used to clone a novel protein, CD2BP1, which specifically associates with the CD2 cytoplasmic tail in T lymphocytes. The yeast two-hybrid interaction trap system (Finley and Brent, 1995) employed a cDNA encoding the human CD2 cytoplasmic tail fused to a LexA promoter binding domain as bait; a cDNA library derived from activated human T cells was screened. For the cDNA library, inserts were fused to the 3' end of the cDNA encoding the B42 transcriptional activator domain. Subsequently, positive interactors were screened against a CD2 tail minus bait, and cDNA clones were obtained which interact with the full length CD2 tail but not the signal transduction incompetent tail minus variant. One of these was termed CD2BP1. CD2BP1 was found in long (CD2BP1L) and short (CD2BP1S) variants arising by alternative RNA splicing.

Biochemical studies mapped the interaction with CD2 to a SH3 domain in CD2BP1, a finding independently confirmed by genetic complementation analysis in yeast. Further mutational analyses localized the CD2BP1 binding site to the area centered about a PPLP sequence (aa 302–305) in the carboxy terminal region of the CD2 tail. This CD2 segment (aa 297–314) contains the sequence most highly conserved among CD2 homologues in all species (Clayton et al., 1987; Tavernor et al., 1994). In addition, CD2BP1 functions as an adaptor to recruit the protein tyrosine phosphatase PTP-PEST (Garton and Tonks, 1994) to the CD2 tail. While CD2BP1 only transiently interacts with CD2, it nevertheless shows a stable association with PTP-PEST. The inducible binding of CD2BP1 to CD2 during CD2 cluster formation is essential for its normal adaptor function in recruiting PTP-PEST to the vicinity of the adhesion complex at the cell-cell junction, thereby regulating adhesion and/or signaling events following CD2-CD58 co-ligation.

Accordingly, this invention pertains to an isolated CD2BP1 protein, and to gene products encoded by nucleotide sequences described herein. The term, "CD2BP1 protein," as used herein, refers to both the CD2BP1L (SEQ ID NO:1) and the CD2BP1S (SEQ ID NO:2) variants of the CD2BP1 protein. The CD2BP1 protein of the invention can be partially or substantially purified (e.g., purified to homogeneity), and/or is substantially free of other proteins. According to the invention, the amino acid sequence of the protein can be that of the naturally-occurring protein or can comprise alterations therein. Such alterations include conservative or non-conservative amino acid substitutions, additions and deletions of one or more amino acids; however, such alterations should preserve at least one activity of the CD2BP1 protein, i.e., the altered or mutant protein should be an active derivative of the naturally-occurring protein. For example, the mutation(s) can preferably preserve the three dimensional configuration of the binding site of the native protein, and/or preserve the SH3 domain of CD2BP1 that interacts with the CD2 tail, so that the altered CD2BP1 protein is capable of interacting with CD2. In another example, the mutation(s) can preferably preserve the ability of the altered CD2BP1 protein to associate with PTP-PEST. The presence or absence of CD2BP1 protein activity or activities can be determined by various standard functional assays including, but not limited to, assays for CD2 binding activity; assays for association with CD2 and/or with PTP-PEST; and assays for cellular effects of CD2BP1 protein on cell adhesion or signal transduction.

Additionally included in the invention are active fragments of the CD2BP1 protein, as well as fragments of the CD2BP1 active derivatives described above. An "active fragment," as referred to herein, is a portion of CD2BP1 protein (or a portion of a CD2BP1 active derivative) that retains CD2BP1 activity, as described above. In a preferred embodiment, the active fragment of CD2BP1 comprises at least the terminal SH3 domain.

Active CD2BP1 derivatives or fragments should comprise amino acids which are essential for the activity of the CD2BP1 protein have been identified as described in the Examples. Appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

The CD2BP1 protein can also be a fusion protein comprising all or a portion (e.g., an active fragment) of the CD2BP1 protein amino acid sequence fused to an additional component, such as a glutathione-S-transferase (GST) polypeptide. Additional components, such as radioisotopes and antigenic tags, can be selected to assist in the isolation or purification of the polypeptide or to extend the half life of the polypeptide; for example, a hexahistidine tag would permit ready purification by nickel chromatography. Furthermore, polypeptides of the present invention can be progenitors of the CD2BP1 protein; progenitors are molecules which are cleaved to form an active CD2BP1 protein.

Also included in the invention are polypeptides which are at least about 90% identical (i.e., polypeptides which have substantial sequence identity) to the CD2BP1 protein described herein. However, polypeptides exhibiting lower levels of identity are also useful, particular if they exhibit high, e.g., at least about 90%, identity over one or more particular domains of the protein. For example, polypeptides sharing high degrees of identity over domains necessary for particular activities, such as the SH3 domain that is necessary for the binding of CD2BP1 protein to CD2, are included herein.

Polypeptides described herein can be isolated from naturally-occurring sources, chemically synthesized or recombinantly produced. Polypeptides or proteins of the present invention can be used as a molecular weight marker on SDS-PAGE gels or on molecular sieve gel filtration columns using art-recognized methods.

The invention also pertains to an isolated nucleotide sequence encoding a mammalian, e.g., primate or human, CD2BP1 protein as described above. As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 25 nucleotides, more preferably at least about 50 nucleotides, and even more preferably at least about 200 nucleotides. The nucleotide sequence can be only that which encodes at least a fragment of the amino acid sequence of the CD2BP1 protein; alternatively, the nucleotide sequence can include at least a fragment of the CD2BP1 protein amino acid coding sequence along with additional non-coding sequences such as introns and non-coding 3' and 5' sequences (including regulatory sequences, for example). Additionally, the nucleotide sequence can be fused to a marker sequence, for example, a sequence which encodes a polypeptide to assist in isolation or purification of the polypeptide. Representative sequences include, but are not limited to, those which encode a glutathione-S-transferase (GST) fusion protein. In a preferred embodiment, the nucleotide sequence encodes CD2BP1L protein (SEQ ID NO:1) or CD2BP1S protein (SEQ ID NO:2); encodes an active derivative or active fragment of CD2BP1L or CD2BP1S; or encodes a polypeptide which is at least about 90% identical (i.e., a polypeptide which has substantial sequence identity) to the CD2BP1 protein described herein. In a particularly preferred embodiment, the nucleotide sequence encoding CD2BP1L is that of SEQ ID NO:16, and the nucleotide sequence encoding CD2BP1S is that of SEQ ID NO:18.

As used herein, an "isolated" gene or nucleotide sequence is intended to mean a gene or nucleotide sequence which is not flanked by nucleotide sequences which normally (in nature) flank the gene or nucleotide sequence (as in genomic sequences) and/or has been completely or partially purified from other transcribed sequences (as in a cDNA or RNA library). Thus, an isolated gene or nucleotide sequence can include a gene or nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the CD2BP1 gene in tissue (e.g., human tissue), such as by Northern blot analysis.

The present invention also pertains to nucleotide sequences which are not necessarily found in nature but which encode the CD2BP1 protein. Thus, DNA molecules which comprise a sequence which is different from the naturally-occurring nucleotide sequence but which, due to the degeneracy of the genetic code, encode the CD2BP1 protein of the present invention are the subject of this invention. The invention also encompasses variations of the nucleotide sequences of the invention, such as those encoding active fragments or active derivatives of the CD2BP1 protein as described above. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the CD2BP1 protein.

The invention described herein also relates to fragments of the isolated nucleic acid molecules described herein. The term "fragment" is intended to encompass a portion of a nucleotide sequence described herein which is from at least about 25 contiguous nucleotides to at least about 50 contiguous nucleotides or longer in length; such fragments are useful as probes, e.g., for diagnostic methods, and also as primers. Particularly preferred primers and probes selectively hybridize to the nucleic acid molecule encoding the CD2BP1 protein described herein. For example, fragments which encode antigenic regions of the CD2BP1 protein described herein are useful. Additionally, fragments which retain CD2BP1 protein activity, as described above, are particularly useful.

The invention also pertains to nucleotide sequences which hybridize under medium, and, more preferably, high, stringency hybridization conditions (e.g., for selective hybridization) to a portion of a nucleotide sequence described herein. Appropriate stringency conditions are known to those skilled in the art or can be found in standard texts such as *Current Protocols in Molecular Biology*, John Wiley & Sons, N.Y. , 6.3.1–6.3.6 (including supplements through 1997). Such hybridizable nucleotide sequences are useful as probes and primers for diagnostic applications. Also included herein are nucleotide sequences which specifically hybridize to a nucleotide sequence encoding CD2BP1 protein, and, optionally, have an activity of a CD2BP1 protein.

Thus, the invention pertains to nucleotide sequences which have a substantial identity with the nucleotide sequences described herein; particularly preferred are nucleotide sequences which have at least about 70%, and more preferably at least about 80% identity, and even more preferably at least about 90% identity, with nucleotide sequences described herein. Particularly preferred in this instance are nucleotide sequences encoding polypeptides having an activity of the CD2BP1 protein described herein. For example, preferred nucleotide sequences encoding a polypeptide having the same or similar biological activity as the CD2BP1 protein and nucleotide sequences encoding a polypeptide with the same or similar immunogenic or antigenic properties as the CD2BP1 protein are within the scope of the invention. As used herein and described above, activities of the CD2BP1 protein include, but are not limited to, interaction with CD2, and association with PTP-PEST.

The invention also provides expression vectors containing a nucleic acid sequence encoding a CD2BP1 protein or active derivative or fragment thereof, operably linked to at least one regulatory sequence. Many expression vectors are commercially available, and other suitable vectors can be readily prepared by the skilled artisan. "Operably linked" is intended to meant that the nucleotide sequence is linked to a regulatory sequence in a manner which allows expression of the nucleic acid sequence. Regulatory sequences are art-recognized and are selected to produce a CD2BP1 protein or active derivative or fragment thereof. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the proteins of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989 Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains), Streptomyces, Pseudomonas, *Serratia amarcescens* and *Salmonella typhimurium*; insect cells (baculovirus), including Drosophila; fungal cells, such as yeast cells; plant cells; and mammalian cells, such as thymocytes, Chinese hamster ovary cells (CHO), and COS cells.

Thus, a nucleotide sequence as described herein can be used to produce a recombinant form of the CD2BP1 protein via microbial or eukaryotic cellular processes. Ligating a polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of CD2BP1 proteins, or active derivatives or fragments thereof, by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind a CD2BP1 protein. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)) which bind to the described gene product are within the scope of the invention. A mammal, such as a mouse, rat, hamster or rabbit, can be immunized with an immunogenic form of the CD2BP1 protein (e.g., the protein or a peptide comprising an antigenic fragment of the protein which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and F(ab)$_2$. Antibodies described herein can be used to inhibit the activity of the CD2BP1 protein described herein, particularly in vitro and in cell extracts, using methods known in the art. Additionally, such antibodies, in conjunction with a label, such as a radioactive label, can be used to assay for the presence of the expressed CD2BP1 protein in a cell, e.g., in cells of a tissue sample, and can be used in an immunoabsorption process, such as an ELISA, to isolate the CD2BP1 protein. Tissue samples which can be assayed include primate, particularly human, tissues, e.g., differentiated and non-differentiated cells. In a preferred embodiment, the tissues comprise hematopoietic tissues.

The present invention also pertains to pharmaceutical compositions comprising CD2BP1 proteins, active derivatives or fragments described herein. For instance, a protein, derivative, or fragment, or prodrug thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

It is also contemplated that cells which, in nature, lack CD2BP1 protein expression and activity can be engineered to express the CD2BP1 protein of the invention by gene therapy methods. For example, DNA encoding the CD2BP1 protein, or an active fragment or derivative thereof, can be introduced into an expression vector, such as a viral vector, and the vector can be introduced into appropriate cells which lack CD2BP1 protein expression in an animal. In such a method, a cell population can be engineered to inducibly or constitutively express active CD2BP1 protein. In a preferred embodiment, the vector is delivered to a hematopoietic tissue, such as the bone marrow as described in Corey et al. (*Science* 244:1275–1281 (1989)).

The present invention also relates to an assay for identifying agents which alter the activity of the CD2BP1 protein. For example, a cell or cell lysate containing the CD2BP1 protein, or an active fragment or derivative thereof, can be contacted with an agent to be tested, and the level of CD2BP1 protein activity, as described above, can be assessed and compared with the corresponding level in a control in the absence of the agent to be tested. The protein can be contacted directly with the agent to be tested, or a cell or cell lysate thereof comprising the CD2BP1 protein (or active fragment or derivative) can be contacted with the agent to be tested. Inhibition of CD2BP1 protein activity relative to a control indicates that the agent is an antagonist of CD2BP1 protein activity; enhancement of CD2BP1 protein activity relative to a control indicates that the agent is an agonist of CD2BP1 protein activity.

As used herein, "inhibition" of CD2BP1 protein activity is intended to encompass any decrease in CD2BP1protein expression or activity, whether brought about by decrease in the activity of the CD2BP1 protein itself, by decrease in the amount of CD2BP1 protein present, or by increase in the amount or activity of an inhibitor of CD2BP1 protein. Inhibitors of CD2BP1 protein activity include agents that decrease expression of CD2BP1 mRNA or translation of CD2BP1 protein; agents that interfere with the interaction between CD2 and CD2BP1 (for example, an antibody that binds to amino acids 300–309 of CD2, or which binds to the SH3 domain of CD2BP1); agents that compete with CD2BP1 protein (for example, a mutant CD2BP1 protein that binds to CD2, yet does not recruit PTP-PEST, or a mutant CD2BP1 protein that interacts with PTP-PEST, yet does not bind to CD2); as well as agents that interfere with the interaction between CD2BP1 and PTP-PEST.

As used herein, "enhancement" of CD2BP1 protein activity is intended to encompass any increase in CD2BP1 protein expression or activity, whether brought about by increase in the activity of the protein itself, or by increase in the amount of protein or mimic present, or both. As used herein, "mimic" is intended to mean an agent which has the same activity as (or mimics) the CD2BP1 protein; "mimics" and include active fragments or derivatives, or other variants of the CD2BP1 protein, as described above. Enhancers of CD2BP1 protein activity include agents that enhance expression of CD2BP1 mRNA or translation of CD2BP1 protein (for example, exogenous nucleic acid encoding CD2BP1 protein); agents that enhance the interaction between CD2 and CD2BP1 (for example, an agent that increases CD2BP1 protein binding to CD2, or which decreases the disassociation of CD2BP1 protein from CD2); as well as agents that enhance with the interaction between CD2BP1 and PTP-PEST.

The present invention also relates to agents identified by the assay described above. Agents identified by the assay described herein may inhibit (e.g., shorten or decrease) or enhance (e.g., prolong or increase) the activity of the CD2BP1 protein. The invention further pertains to methods of inhibiting the activity of the CD2BP1 protein, as well as to methods of enhancing the activity of the CD2BP1 protein, such as by contacting the CD2BP1 protein with a CD2BP1 protein antagonist or a CD2BP1 protein agonist as described above.

The invention further pertains to methods of identifying agents which modulate (i.e., inhibit or enhance) signal transduction or cell adhesion. As discussed in detail in the Examples below, CD2BP1 protein binds CD2 and associates with PTP-PEST, recruiting PTP-PEST to the vicinity of the adhesion complex at the cell-cell junction, and thereby regulating adhesion and/or signaling events following CD2–CD58 co-ligation. Therefore, agents which modulate (inhibit or enhance) CD2BP1 protein activity will consequently modulate signal transduction or cell adhesion. In an assay to identify an agent which modulates signal transduction or cell adhesion, for example, a cell or cell lysate containing the CD2BP1 protein, or an active fragment or derivative thereof, can be contacted with an agent to be tested, and the level of CD2BP1 protein activity, as described above, can be assessed and compared with the corresponding level in a control in the absence of the agent to be tested. The protein can be contacted directly with the agent to be tested, or a cell or cell lysate thereof comprising the CD2BP1 protein (or active fragment or derivative) can be contacted with the agent to be tested. Modulation of CD2BP1 protein activity relative to a control indicates that the agent modulates CD2BP1 protein activity, and is therefore modulates signal transduction or cell adhesion. Inhibition of CD2BP1protein activity relative to a control indicates that the agent inhibits CD2BP1 protein activity, and therefore enhances signal transduction or cell adhesion. Similarly, enhancement of CD2BP1 protein activity relative to a control indicates that the agent enhances CD2BP1 protein activity, and therefore inhibits signal transduction or cell adhesion. The invention further pertains to methods of modulating (enhancing or inhibiting) signal transduction of cell adhesion by modulating (inhibiting or enhancing) the activity of the CD2BP1 protein. For example, the activity of the CD2BP1 protein can be modulated by contacting the CD2BP1 protein with a CD2BP1 protein antagonist or a CD2BP1 protein agonist as described above.

Inhibition of CD2BP1 protein activity, as described above, can be useful in prolonging cell adhesion or enhancing signal transduction; prolonging cell adhesion and/or enhancing signal transduction can be used in cancer therapy, to augment the immune response to cancerous cells and tumors. Enhancement of CD2BP1 protein activity, as described above, can be useful in reducing cell adhesion or inhibiting signal transduction. This is particularly useful in immunocompromised individuals, and in immunodeficiency related diseases.

Enhancement or inhibition of CD2BP1 protein activity as described above can also be useful in the treatment of disorders of relating to autoimmune diseases, such as, but not limited to rheumatoid arthritis, juvenile diabetes, and systemic lupus erythmatosis (SLE); it can also be used in transplantation, for example, to reduce adhesion of the recipient's T cells with tissues in the autograph. Moreover, the CD2BP1 protein itself can be used in such therapy.

The invention additionally pertains to methods of targeting proteins to a CD2 molecule. Because CD2BP1 protein recruits PTP-PEST to the vicinity of CD2, CD2BP1 protein can be used in a similar manner to target another protein (a "target protein"), such as a kinase or phosphatase, to the vicinity of CD2. The target protein is linked to CD2BP1 protein, either chemically or physically, in a manner such that the interaction between CD2BP1 protein and CD2 is not affected (i.e., such that the SH3 domain of the CD2BP1 protein can still bind with CD2). When the CD2BP1 protein interacts with CD2, the target protein that is linked to the CD2BP1 protein is thereby brought nearby to CD2 as well.

The following Examples are offered for the purpose of illustrating the present invention and are not to be construed to limit the scope of this invention. The teachings of all references cited are hereby incorporated herein by reference.

EXAMPLE 1

Experimental Procedures

A. Construction and Screening of cDNA Libraries

Human peripheral blood mononuclear cells (PBMCs) were isolated by ficoll gradient centrifugation of peripheral blood from healthy blood donors. Activated T cells were obtained by culturing the PBMCs in RPMI 1640 (Life Technologies, Bethesda, Md.) containing a 1:200 dilution of 2Ad2 ascites (anti-human CD3$\epsilon$, mAb), 25 ng/ml PMA, 10% FCS, 1% penicillin/ streptomycin, 2 mM glutamine. After 48 h of activation, $\geq$94% of the residual cell population was anti-CD2 reactive as shown by FACS analysis. Total RNA was prepared from the activated T cells by the guanidine-thiocyanate gradient centrifugation method (Kingston, 1987). The mRNAs were isolated from the total RNA using a polyA spin™ mRNA isolation kit (NEB). The cDNA library was synthesized using a cDNA synthesis kit (Stratagene) with an oligonucleotide containing an XhoI restriction site and polydT at the 3' end and ligated to an EcoRI adapter at the 5' end. After digestion with XhoI and EcoRI, the cDNAs were ligated to the yeast vector pJG4-5 (trp+) downstream of the B42 activator ORF between the EcoRI and XhoI sites. The constructs were used to transform E. coli strain DH12S (BRL) yielding $4 \times 10^6$ colonies. The cDNA containing plasmids were then purified from the E. coli colonies and used to transform yeast EGY48 already pretransformed with the yeast vector pSH1834 (lacZ reporter, ura+) and pEG202/CD2 (his+)(Finley and Brent, 1995). The transformants were plated on ura-, his-, trp-yeast minimum medium plates and about $7 \times 10^6$ colonies were screened based on their selective growth on ura-, his-, trp-, leu-plates and blue colony color due to lacZ expression under galactose-induced conditions (Finley and Brent, 1995). The cDNA plasmids from positive colonies were purified and further examined for their lack of growth or lacZ expression when co-transformed with the yeast vector pEG202/$\Delta$CD2 containing the LexA-CD2 tail truncation fragment. The colonies giving positive growth in ura-, his-, trp-, leu–medium or showing lacZ expression only when the cDNAs were co-transformed with pEG202/CD2 but not pEG202/$\Delta$CD2 were considered significant and their cDNA inserts were subjected to DNA sequencing.

To characterize independent CD2BP1 cDNA clones, a ZAP express™ cDNA phagemid library was constructed using polyA+RNA from 72 hours-activated human T cells (obtained as above), a ZAP express™ cDNA synthesis kit and ZAP express™ cDNA gigapack II gold cloning kit (all from Stratagene). The XhoI fragment of CD2BP1S was labeled for library screening by random priming using $\alpha$-$^{32}$P dCTP and a random primed DNA labeling kit (Boehringer Mannheim). Inserts of selected positive clones were sequenced. CD2BP1L was derived from this library.

B. Yeast Complementation Analysis of Variant Proteins

To examine the interaction of different truncated or mutated versions of the –CD2 tail with different variants of CD2BP1, the cDNAs corresponding to each protein were generated from the original clones by PCR (Higuchi et al., 1988) and inserted into the relevant yeast expression vectors. For CD2 tail variants, the cDNAs were inserted in the pEG202 vector between the EcoRI and SalI sites. For the CD2BP1 series, the cDNAs were inserted between the EcoRI and XhoI site of the pJG4-5 vector. The authenticity of all DNA constructs was confirmed by DNA sequence analysis. Different combinations of CD2 tail constructs and CD2BP1 constructs were used to doubly transform yeast EGY48 pretransformed with the pSH1834 vector. The triple transformants were selected for their growth in ura-, his-, trp-minimum medium. The colonies were then test for lacZ expression under galactose-induced conditions. The combinations which resulted in lacZ expression in transformed yeast under inductive conditions were scored as a specific interaction between the CD2 tail variant and the CD2BP1 variant.

C. Northern Analysis and 5'-rapid Amplification of cDNA Ends (5'-RACE) of CD2BP1

For northern blot analysis of different human hematopoietic cell lines or the Hela cell line, 10 µg of purified total RNA was electrophoresed on a 1% agarose gel at 80 V for 3–4 h. The separated RNAs were then transferred to Biotrans nylon membranes (ICN) in 20×SSC overnight, followed by washing in 2×SSC and baking at 80° C. for 2 h. For hybridization, the XhoI fragment of CD2BP1S was isolated from the CD2BP1S cDNA plasmid and $^{32}$P-labeled. The membrane was hybridized to the labeled fragment using the ExpressHyb solution (Clontech) followed by several washes prior to autoradiography as per the manufacturer's instructions. For northern blots of RNA from different human tissues, two human multiple tissue northern blots were purchased from Clontech. Each lane on the membrane represents 2 µg of mRNA from different human tissues. The probing, washing and autoradiography were performed per the manufacturer's protocol.

For 5'-rapid amplification of cDNA ends (5' RACE) analysis of the cDNA sequence upstream of the existing CD2BP1 cDNA clone, a reverse primer corresponding to bp 307–326 of CD2BP1S and polyA+RNA purified from activated human T cells were used. The 5' RACE system (GIBCO/BRL) was used to generate dC-tailed 5' cDNA according to the manufacturer's protocol. The first PCR was performed using the cDNA generated as template, the provided AAP oligonucleotide 5' primer and a unique reverse primer corresponding to bp 178–202 of CD2BP1S as the 3' primer. The second PCR was performed using the first PCR product as template, the provided UAP oligonucleotide as the 5' primer and a unique reverse primer corresponding to bp 59–83 of CD2BP1S as 3' primer. The second PCR product was ligated into the pCR 2.1 vector (Invitrogen) according to the manufacturer's protocol, followed by DNA sequencing analysis of the insert.

D. Generation of a Recombinant GST-CD2BP1SH3 Fusion Protein and Analysis of its Interaction With CD2 in Human T Lymphocytes To generate a GST-CD2BP1SH3 fusion protein, the cDNA sequence corresponding to amino acids 361–416 of CD2BP1L was inserted into the pGEX-4T-1 vector (Pharmacia) between the EcoRI and XhoI site in the linker region C terminal to the GST binding domain. The construct was used to transform E. coli XL2-Blue (Stratagene) and the fusion protein generated by culturing the transformed E. coli under IPTG inducing conditions (0.1 mM IPTG for 2–3 h at 37° C.). The fusion protein and/or GST control protein was then purified using Glutathione-Sepharose 4B beads according to the manufacturer's protocol (Pharmacia).

To analyze the ability of the GST-CD2BP1SH3 fusion protein to interact with CD2, human T cells were purified from PBMCs by nylon wool (Hathcock, 1994) and activated for 72 h by culturing in 2Ad2 and PMA as described above. The T cells were lysed at 30 million cells/ml in lysis buffer [1% Triton, 0.15M KCl, 1×TBS (10 mM Tris pH 7.4, 0.15M NaCl)] with or without divalent cations ($Zn^{2+}$, $Mg^{2+}$ or $Ca^{2+}$) as indicated, supplemented with 1 mM PMSF, 5 µg/ml leupeptin and 0.35 TIU (trypsin inhibitor unit)/ml aprotinin. Following 30 min at 4° C., the lysates were microcentrifuged for 30 min, and the supernatants precleared by incubating overnight with GST-sepharose beads (~5 mg protein/ml glutathionine Sepharose). The precleared lysates were then incubated overnight with glutathione sepharose beads coupled with either the GST-CD2BP1SH3 fusion protein or GST alone (as a control). After two washes with lysis buffer (without proteinase inhibitors), the beads were incubated at 65° C. for 20 min in SDS sample buffer and subjected to 12.5% SDS PAGE. The proteins on the gel were then transferred to nitrocellulose membranes for Western blot analysis. The bound CD2 protein was then revealed by probing the membrane first with a 1:1000 dilution of polyclonal M32B rabbit anti-human CD2 (Recny et al., 1990) antibody preabsorbed on bacteria lysates, followed by incubation of the membranes with HRPO-conjugated goat anti-rabbit antibody (Biorad) at a 1:10,000 dilution. The signal was then developed by ECL (NEN).

E. Generation of Mouse mAbs Specific for Human CD2BP1

To develop mAbs specific for CD2BP1, the purified GST-CD2BP1-SH3 fusion protein was used as an immunogen. Specifically, the protein was emulsified in complete Freund's adjuvant to a final concentration of 200 µg/ml. 100 µg of the protein antigen was then given intraperitoneally to each of several 8 week old Balb/c mice. Subsequently, the immunized mice were boosted three more times with the same fusion protein emulsified in incomplete Freund's adjuvant. About $4 \times 10^8$ splenocytes from two immunized mice were fused to NS-1 myeloma cells, cultured in selective HAT medium and hybridoma supernatants were then screened for positive binding to the GST-CD2BP1 SH3 fusion protein using standard methods (Meuer et al., 1984). After incubating the supernatant in 96 well plates precoated with GST-CD2BP1-SH3 protein at 5 µg/ml, the bound mAbs were detected with alkaline phosphatase conjugated goat antimouse IgG (American Qualex). The reaction was developed using the phosphatase-specific reaction with its substrate/Sigma 104 at 1 mg/ml (Sigma) in DEA buffer (49 mg $MgCl_2 \cdot 6H_2O$/L, 96 ml diethanolamine/L, pH 9.8) and the color density determined by OD reading on an ELISA reader (spectraMAX 250) at 405 nm. The supernatants from the positive hybridomas were further screened for binding to plates coated with GST protein alone under the identical conditions. Hybridomas secreting antibodies binding only to the GST-CD2BP1-SH3 protein but not GST were subcloned twice and used to generate ascites in pristane-primed Balb/C retired breeders. The mAbs were further purified from ascites by protein G (or protein A) affinity columns. The purified antibodies were coupled to CNBr activated Sepharose 4B beads by a standard protocol (Meuer et al., 1984).

F. Metabolic Labeling and Biochemical Characterization of CD2BP1

For metabolic labeling and immunoprecipitation studies, activated human T cells were washed twice with cysteine and methionine free RPMI 1640 (ICN) and the cells were labeled by incubating in the same medium supplements with 1.0 mCi/ml $^{35}$S-met (NEN) for 6 h. The labeled T cells were lysed in lysis buffer (described above) at $40 \times 10^6$/ml for 30 min. After centrifugation, the supernatants were precleared twice by incubation with CNBr sepharose 4B beads coupled with the 2H11 mAb (anti-leucine zipper specific)(Chang et al., 1994). The precleared supernatant was diluted 1:4 in lysis buffer containing 0.1% BSA to reduce non-specific binding of the labeled proteins to beads. Immunoprecipitation was performed by incubating the supernatants for 3 h with CNBr sepharose beads coupled to the appropriate mAbs. The beads were subsequently washed with lysis buffer containing 0.1% BSA and 0.5M NaCl, lysis buffer containing 0.1% BSA and 10 mM EDTA and lysis buffer containing 0.1% BSA and 0.1% SDS. After two final washes in TBS (10 mM Tris, pH 7.4, 0.15 M NaCl), the beads were incubate in SDS sample buffer at 65° C. for 20 minutes and subjected to reducing SDS/PAGE analysis. Following staining and destaining procedures, the gels were incubated in enhancing solution (NEN) for 20 min, vacuum dried and autoradiographed overnight.

G. Fluorescence Microscopy Analysis of the Distribution Pattern of CD2BP1 and its Association with CD2

To examine the distribution pattern of CD2BP1, about $2 \times 10^6$ activated human T cells were incubated with directly conjugated Texas red labeled anti-T11$_1$ mAb (5 μg/ml) in FACS buffer (2% FCS in PBS) at 4° C. for 30 min, followed by two washes in the same buffer and then fixation with 2% (w/v) paraformaldehyde/PBS for 30 min at 4° C. The cells were then permeabilized by incubation in permeabilization buffer [0.1% saponin (Sigma) in FACS buffer] at 4° C. for 30 min, and stained with directly FITC-labeled anti-CD2BP1 mAb (8C93D8, 5 μg/ml) in permeabilization buffer at 4° C. for 30 min. After three washes in permeabilization buffer and one wash in PBS, the cells were resuspended in 1% paraformaldehyde/PBS and analyzed under 60× magnification on a Nikon Diaphot 300 fluoromicroscope equipped with photometric PXL cooled CCD camera linked to an Oncor imaging analysis system as described previously (Li et al., 1996).

For image analysis of the CD2BP1 association with CD2, CD2 molecules on the activated T cell surface were induced to cluster by either a pair of anti-CD2 antibodies (anti-T11$_2$ plus anti-T11$_3$) or by CD58 ligand directed CD2 relocalization. For antibody crosslinking, activated T cells were incubated with anti-T11$_2$ mAb (5 μg/ml) and direct Texas red labeled anti-T11$_3$ mAb (1:50) in FACS buffer at 4° C. for 30 min, followed by two washes with FACS buffer and fixation by incubation in 2% paraformaldehyde/PBS. The cells were then permeabilized and stained with directly FITC-labeled anti-CD2BP1 mAb, followed by fluoroimaging analysis as described above. For ligand induced surface CD2 relocalization, activated T cells were incubated with CD58 transfected CHO cells prebound to coverslips to induce cellular conjugate formation as described previously (Li et al., 1996). After washing off the non-conjugated T cells and fixation in 1% paraformaldehyde, the conjugates were stained with anti-T11$_3$ antibody (1:50) at 4° C. for 30 min, followed by washing, permeabilization and staining with anti-CD2BP1 antibody as described above. The stained conjugates on the coverslips were then subject to fluoroimaging analysis.

H. Protein Tyrosine Phosphatase Characterization and Activity Assay

To identify the protein tyrosine phosphatase associated with CD2BP1, activated human T cells were disrupted in lysis buffer at $30 \times 10^6$/ml and the supernatant collected as described above. After preclearing with control beads (CNBr activated beads linked to nonspecific mouse IgG at 5 mg/ml, Sigma) overnight, the supernatant was diluted to $10 \times 10^6$ cells/ml in lysis buffer containing 0.1% BSA. CD2BP1 and any associated molecules were immunoprecipitated by incubation at 4° C. for 3 h with CNBr beads coupled to either anti-CD2BP1 mAb 8C93D8 or, as a control, nonspecific mouse IgG. After two washes in lysis buffer and one wash in TBS, the immunocomplexes on the beads were eluted by heating at 65° C. for 20 min in SDS sample buffer and subjected to 12.5% reducing SDS/PAGE. After electrophoresis, proteins on the gel were transferred to nitrocellulose for Western blotting. The membranes were then probed with different primary antibodies: rabbit anti-human PTP-PEST (CSH8) 1:1000 (Garton and Tonks, 1994), rabbit anti-human FLP (αEN12) 1:1000 (Dosil et al., 1996), goat anti-human SHPTP1 (Santa Cruz) 1:100, rabbit antihuman SHPTP2 (Santa Cruz) 1:100, followed by washing and incubation with the secondary HRPO-conjugated goat anti-rabbit antibody (1:5000) or donkey anti-goat antibody (Santa Cruz) 1:2000, and signals developed by ECL.

In vitro protein tyrosine phosphates assay: After immunoprecipitation as described above, the 8C93D8 beads or control beads were washed once with lysis buffer containing 0.5% DOC (sodium deoxycholate), 0.5M NaCl and 0.1% BSA, followed by washing with lysis buffer containing 0.5% DOC, 0.1% SDS and 0.1% BSA, and finally two washes with 50 mM Tris, pH 7.5, 0.15% 2-mercaptoenthanol, 0.0075% Brij 35 and 0.025 mM EDTA. The immunocomplex bound on the beads was assayed for the PTPase activity on $^{32}$P-labeled tyr Raytide as measured by the $^{32}$P release from the peptide using a previously established protocol (Tsai et al., 1991). $^{32}$P labeling of Raytide at the tyrosine residue was prepared using an established kinase reaction procedure (Tsai et al., 1991) with the synthetic peptide Raytide as substrate (Calbiochem), γ-32P ATP (NEN) as the $^{32}$P donor and v-abl as the tyrosine kinase (Calbiochem). After incubation at 37° C. for 5 h, the $^{32}$P-labeled Raytide was precipitated twice by TCA and the substrate was finally dissolved in 0.2M Tris, pH 8.0 for phosphatase assay as described (Tsai et al., 1991).

In vitro kinase assay: Immunoprecipitation was performed as described above except using a modified lysis buffer containing 1 mM Na$_3$VO$_4$, 5 mM Na$_2$H$_2$P$_2$O$_7$ and 5 mM NaF in addition to the other existing components. The beads were then washed twice with lysis buffer and twice with kinase buffer (100 mM NaCl, 5 mM MnCl$_2$, 5 mM MgCl$_2$, 20 mM Hepes, pH7.4). The kinase reaction was conducted in 50 μl kinase buffer containing 2 /M ATP, 10 μCi $^{32}$P γATP and 10 μg of one of the following kinase substrates: histone H1 (Calbiochem), poly GluTyr (Sigma) or Raytide (Calbiochem). After 15 min incubation at room temperature, the reaction was terminated by boiling in SDS sample buffer, followed by either 9% SDS/PAGE or spotting onto P81 phosphocellulose paper (Gibco), followed by three washes with 0.5% phosphoric acid. The results were analyzed by autoradiography.

EXAMPLE 2

Two-hybrid Screening of CD2 Cytoplasmic Tail Interaction Proteins

Structure of CD2 and its interaction with CD58

Considerable structural detail exists regarding CD2 and its CD58 binding site. Nuclear magnetic resolution studies of the NH2-terminal domain of rat and human CD2 (Driscoll et al., 1991; Withka et al., 1993) and X-ray crystallographic studies of the entire extracellular segment of rat and human CD2 (Bodian et al., 1994; Jones et al., 1992) have revealed that the extracellular segments consist of two immunoglobulin superfamily (IgSF) domains: a nine-stranded NH$_2$-terminal V set domain lacking the first half of strand A and a seven-stranded membrane-proximal C2-set domain. Prior studies have shown that the N-terminal membrane distal-domain (D1) mediates the adhesion function of the molecules, and subsequent adhesion, by binding to the relevant counter-receptor (Recny et al., 1990; Sayre et al., 1989). Mutational analysis of human CD2 has demonstrated that the CD58 binding surface is located on the highly charged GFCC'C" (SEQ ID NO:24) face of the protein (Arulanandam et al., 1993b; Osborn et al., 1995; Peterson and Seed, 1987; Somoza et al., 1993). Notably, this same surface area forms a homodimeric contact in the crystal structures of rat and human CD2 (Bodian et al., 1994; Jones et al., 1992). Further mutational studies in rat and human systems have suggested that the receptor-ligand interaction involves the major β sheet surfaces of both CD2 adhesion and co-receptor domains (Arulanandam et al., 1994; van der Merwe et al., 1994).

It has recently been observed that during CD58-induced redistribution of CD2, a neoepitope defined by anti-CD2R mAbs is exposed (Li et al., 1996). This epitope maps to the flexible linker region between CD2 D1 and D2 (Li et al., 1996). CD2R+ molecules, in contrast to CD2R− molecules, are tightly clustered on the T cell surface (Li et al., 1996). Hence, an increase in the D1-D2 interdomain angle apparently exposes CD2R, facilitates packing of CD2 molecules in a clustered array and is linked to CD2-mediated adhesion and activation events. Of interest but somewhat unexpectedly, this CD2 reorganization process is not dependent on the CD2 cytoplasmic tail as shown by analysis of cytoplasmic tail deletion mutants (Bierer et al., 1988; Chang et al., 1989; Hahn and Bierer, 1993).

It is noteworthy that the positively charged CD2 cytoplasmic tail segment (pI~12) contains 116 aa, 20% of which are prolines (Clayton et al., 1987; Sayre et al., 1987; Tavernor et al., 1994). One or more of these proline-rich segments may serve as a docking site for SH3 domains. To date, two reports have suggested that $p59^{fyn}$ and $p_{56}^{lck}$ may be directly associated with the CD2 tail. One of these studies has utilized CD2-based peptides and lysates from cells overexpressing recombinant lck to demonstrate an interaction between these two components (Bell et al., 1996). The other study utilizing immunofluorescence analysis found co-localization of $p_{59}^{fyn}$ with CD2 in permeabilized lymphocytes (Gassmann et al., 1994). An association between $p_{56}^{lck}$ and CD2 was not observed in this second study.

Use of Yeast Two-hybrid System to Identify Interactors

To identify proteins interacting with the CD2 cytoplasmic tail, a yeast two-hybrid system was employed, using the full length CD2 cytoplasmic tail cDNA sequence in EG202 as bait and a T cell-derived cDNA library ligated into the pJG4-5 yeast vector (Finley and Brent, 1995). As shown in FIG. 1, the pEG202 plasmids encode the LexA binding protein fused at its C terminus to either the CD2 bait fragment (CD2)(aa 221–327) or a control truncation fragment (ΔCD2)(aa 221–253). The relevant CD2 cDNAs were cloned into the EcoRI (thin line) and SalI (thick line) sites within the pEG202 vector. The transcription of the DNA fusion protein is under the control of the constitutive ADH1 promoter. Positions of the CD2 amino acids and their corresponding nucleotides in the bait or its control are shown under the construct. The pJG4-5 plasmids contain DNA of the activator protein B42 fused at its C-terminal to the cDNAs of the T cell library cloned into the EcoRI (thin line) and Xho I (thick line) sites of the vector. The transcription of the fusion protein is under the control of the GAL 1 promoter, which is repressed in the presence of glucose and induced in the presence of galactose.

In this yeast interaction trap system, the CD2 tail cDNA (nucleotide 756–1076, aa 221–327)(Clayton et al., 1987; Sayre et al., 1987) is fused downstream of the DNA encoding the LexA promoter binding domain such that the hybrid protein is constitutively expressed from an ADH1 promoter. Moreover, this protein can specifically bind to a promoter sequence containing a LexA binding site. However, in the absence of an activation domain, transcription is not initiated. In parallel, individual inserts from the activated T cell derived cDNA library were ligated into pJG4-5 downstream of the B42 transcription activation domain. Expression of this latter fusion protein is regulated by a GAL1 promoter such that its transcription is repressed in the presence of glucose but induced by galactose. In yeast, the interaction of the chimeric CD2 tail protein produced by pEG202 with a B42-cDNA fusion transcriptional protein brings the B42 transcriptional activation domain close to the LexA binding site on the colE1 LexA operator, resulting in activation of the downstream reporter gene (leucine [leu] synthetase or lac Z). An interaction between the CD2 tail and any given cDNA product, therefore, can be detected as either yeast growth in leu−medium or colonies showing blue color in the presence of X-gal under inductive conditions. As an additional control for the specificity of the binding of the cDNA encoded protein to the CD2 cytoplasmic tail, a CD2 tail-deletion construct was also engineered in pEG202 consisting of bp 756–854 (aa 221–253) and termed ΔCD2. pEG202/CD2 and pJG4-5/CD2BP1 double yeast transformants would interact and, thus, grow in leu−medium and manifest lacZ expression in leu+medium.

Of the approximately $7 \times 10^6$ yeast transformants screened in the CD2 tail interaction trap system, nine independent colonies containing distinct insert sizes were identified as positive. Among them, clone #48 (CD2BP1S) showed a strong and specific interaction. Under galactose induction conditions, transformation of the CD2 tail/pEG202 and CD2BP1S/pJG4-5 plasmids (CD2/BP1) in yeast yielded double transformants positive for growth in leu−medium and lacZ expression in leu+medium. In contrast, in the absence of induction (i.e. the presence of glucose), doubly transformed colonies showed neither growth in leu−medium nor lacZ induction in leu+medium. These results indicate that the interaction between the hybrid CD2 tail protein and the CD2BP1 fusion protein is specific rather than a secondary effect of the CD2 tail fusion on yeast growth or LexA expression. Furthermore, when the ΔCD2 construct was analyzed under the same conditions in either induced or uninduced states, the doubly transformed yeast (ΔCD2/BP1) gave negative results for both leu−growth and lacz expression. These findings demonstrate that CD2BP1 specifically interacts with the CD2 tail rather than another component of the fusion protein. Given that ΔCD2 encodes only the membrane proximal 43 aa of the 116 aa long CD2 cytoplasmic tail, which is itself incapable of mediating CD2-based signal transduction (Chang et al., 1989), this result suggests that CD2BP1 may be responsible for a critical component of the CD2 tail function.

EXAMPLE 3

Sequence Analysis of CD2BP1 Clones

Figure 2:
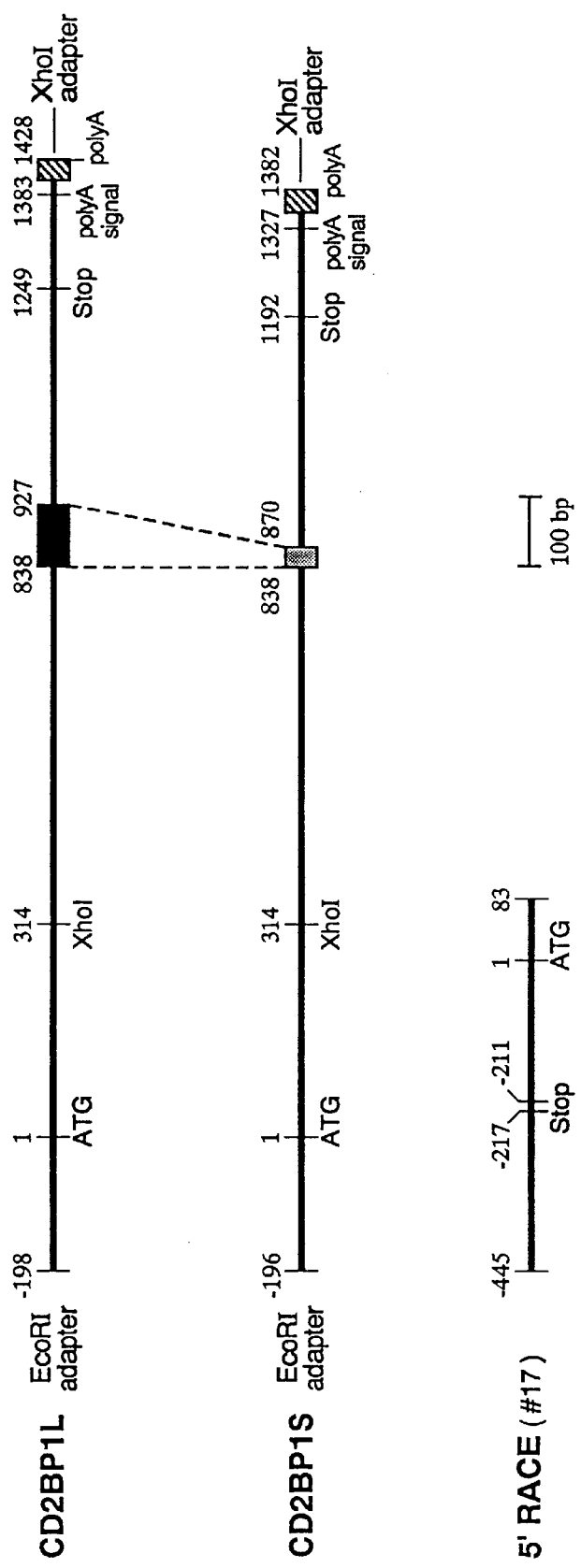
FIG. 2 is a schematic representation of the structure of the nucleic acid for CD2BP1L, CD2BP1S, and a 5'-RACE (Rapid amplification of cDNA ends) construct used to identify the start codon for CD2BP1S.

DNA sequencing of the CD2BP1S cDNA fragment showed a 1,578 bp insert containing several potential translation start codons close to the 5' end of the sequence and a 3' polyadenylation track (FIG. 2 and data not shown). Position 1 is arbitrarily designated as the first nucleotide of the translation initiation codon. The relative position of an internal XhoI site, stop codon, poly A signal (AATAAA) and poly A are indicated in the cDNA fragment. At the 3' end of each cDNA is the XhoI adapter and at the 5' end of each cDNA is the EcoRI adapter. The position and length of the putative differentially spliced fragments in CD2BP1L and CD2BP1S are shown as solid bars in the cDNAs. The 5' RACE cDNA product contains two in frame stop codons positioned at −211 and −217 upstream of the translation initiation codon. Also shown is the unit length scale of each 100 base pairs.

None of the potential start codons showed a canonical Kozak sequence. In addition, because Northern analysis indicated that the size of the intact CD2BP1 mRNA was ~1.9 Kb (see below) and there was an open reading frame extending 5' of the ATG in the cDNA insert, it was unclear hether the entire coding region of CD2BP1S had been cloned. Therefore, 5' RACE as described in Example 1 was employed to define the entire coding region of CD2BP1. A 528 bp fragment RACE product (#17) including ~200 bp 5' of the CD2BP1S cDNA clone was then sequenced. This analysis revealed that there was no putative start codon in this upstream 5' sequence, but rather, two in-frame stop codons. From this analysis, it was concluded that the ATG at bp 1–3 in the CD2BP1S clone represents the translation initiation site (amino acid 1). The amino acid sequence deduced from that cDNA is shown in FIG. 3. The sequences exhibiting high homology to yeast cdc15 and to a typical SH3 domain are boxed. Potential PEST (pro, glu, ser and thr) rich regions are underlined. Alignment was prepared using the GCG Program (Computer Genetics Group, 1991). Solid triangles denote the beginning and end of the segments with differing amino acid sequences in CD2BP1S and CD2BP1L.

To verify the sequence of CD2BP1S, an independent cDNA library, derived from activated T cells, was synthesized, and screened using a 1 Kb CD2BP1S cDNA XhoI fragment. One clone among several, termed CD2BP1L, was isolated with an almost identical sequence to that of CD2BP1S. However, nucleotide 838–870 of CD2BP1S cDNA were replaced by a distinct 89 nucleotide segment (bp 838–927) in the CD2BP1L cDNA (see FIG. 2). Analysis of the nucleotides flanking this 89 bp sequence of CD2BP1L and the 32 bp sequence of CD2BP1S identified splice junction donor and acceptor sites, strongly implying that CD2BP1L and CD2BP1S are RNA splice variants derived from a single CD2BP1 gene. The deduced amino acid sequence of CD2BP1L (FIG. 3) shows 30 aa (aa residues 280–309) which are replaced by 11 aa (aa residues 280–290) in CD2BP1S.

Amino acid sequence analysis of CD2BP1L and CD2BP1S by BLAST homology search (Altschul et al., 1990) and visual inspection identified three striking features in these gene products. First, as shown in FIG. 4, amino acids 123–288 of CD2BP1L show significant (30%) sequence identity with *S. pombe* cdc15 (Fankhauser et al., 1995). Identical amino acids are boxed in black. PAIRCOIL program analysis of the CD2BP1L and CD2BP1S sequences reveals a potential coiled-coil structure located within this region of the protein (aa 162–204 with score=1.7–4.3) (Berger et al., 1995). The homology observed between the amino acid sequences of CD2BP1 and cdc15 (*S. pombe*) suggest that the function of these two molecules in the cell may be related. cdc15 has been found to represent a critical component involved in cytoskeletal rearrangements related to actin ring formation during yeast cell division. Although the detailed mechanisms involving cdc15 function are yet to be determined, heavily phosphorylated cdc15 is detected during this process. The presence of multiple shared tyrosine residues in CD2BP1L and CD2BP1S suggests that by binding to the CD2 tail, CD2BP1 may regulate CD2-related cytoskeletal rearrangement events in a manner analogous to that of its cdc15 counterpart.

Second, the search also identified the presence of an SH3 domain at the C terminus of CD2BP1 (aa 360–416). As shown in FIG. 5, this segment (labeled CD2BP1-SH3) contains canonical features of all SH3 domains (Al4, L15, Y16, D17, E25, G31, W59, W60, G73, P76, Y79; numbered according to FIG. 5 alignment only)(Guruprasad et al., 1995; Musacchio et al., 1994). Homology was also observed with SH3 domains of the following proteins: chicken spectrin α-chain (spct; Proetin Data Base PDB/1SHG/) (SEQ D NO:6); human α-fodrin (afod; gb/MI8627/) (SEQ ID NO:7); *Acanthamoeba castellanii* myosin IC heavy chain (myosinHC; sp/P10569) (SEQ ID NO:8); human abl interactor 2 protein (ablint; gb/U23435) (SEQ ID NO:9); human neutrophil cytosol factor 2 (sp/P14598/), SH3 domain a (cytoFa) (SEQ ID NO:10) and SH3 domain B (cytoFb) (SEQ ID NO:13); mouse Grb2 protein (grb2; PBD/1GBR/) (SEQ ID NO:11); fission yeast cell division control protein (cdc15) (sp/Q09822/) (SEQ ID NO:12); and human phosphatidylinositol 3-kinase (PI-3 kinase) (PI3K; PDB/IPKS/) (SEQ ID NO:14). Highly conserved amino acids in SH3 domains are labeled with (*). It is noteworthy that the related carboxy terminal SH3 domain is found *S. pombe* cdc15 and all cdc15 family members (Fankhauser et al., 1995).

Third, a PEST rich region (proline, glutamic acid, serine and threonine) is found between the more N-terminal cdc15-like domain and the SH3 domain (Rechsteiner and Rogers, 1996)(see FIG. 3). In CD2BP1L, this extends from aa residues 320–340. In CD2BP1S, as a consequence of RNA splicing variation, there are two PEST sequences, aa 272–283 and 301–321.

EXAMPLE 4

CD2BP1 is Expressed in Hematopoietic Tissues and Prominently Represented in Mature T Cells and NK Cells To determine the expression pattern of the CD2BP1 gene, a series of RNAs derived from human cell lines was analyzed by Northern blot analysis using the 1 Kb XhoI fragment of CD2BP1S as a probe. Cell lines included resting human T cells from human peripheral blood leukocytes (PBL); activated T cells (72 hours activated human T cells from human PBL); thymocyte (human thymus) cells; mature human natural killer cell line; immature IL-3 dependent mouse line Baf3: EBV-transformed human B cell line Laz 509; human cervix epitheloid carcinoma (HeLa).

A prominent band migrating close to the 18S RNA with an estimated molecular size of ~1.9 Kb is present in resting and activated T cells as well as the NKL IL-2 dependent human NK cell line (data not shown). Detectable but low levels of CD2BP1 message are present in thymocytes and the EBV-transformed B lymphoblastoid cell line, Laz509 (data not shown). In contrast, the non-hematopoietic Hela human tumor line lacks CD2BP1 message (data not shown). The immature IL-3 dependent murine lymphoid cell line Baf3 expresses little if any CD2BP1 related message (data not shown). Comparison of steady state CD2BP1 expression in resting vs. activated human T cell populations demonstrates an increase in CD2BP1 message level following three days of activation by anti-CD3 mAb plus PMA (data not shown). Using reverse PCR and specific primers covering the junctional differences between CD2BP1L and CD2BP1S, no detectable alterations were observed in relative expression of the RNA splice variants in resting vs. activated T cells. However, CD2BP1L was clearly the predominant isoform in both cases (data not shown). A less intense ~3.6 Kb band is observed in activated T cells and is also observed in Northern blots using polyA+RNA (data not shown). Presumably this band represents an alternative polyadenylated message, either a pre-mRNA or a mature splicing variant.

To study further the tissue distribution pattern of CD2BP1, additional Northern blot analysis was performed on polyA+RNA derived from a variety of different human organs, including spleen, thymus, prostate, testis, ovary, small intestine, colon (mucosal lining), peripheral blood leukocyte, heart, brain, placenta, lung, liver, skeletal muscle, kidney and pancreas. The expression of CD2BP1 is largely restricted to the hematopoietic tissues, being prominent in spleen and peripheral blood leukocytes (data not shown). Thymus, small intestine, lung and placenta show very low levels of expression while no message is detected in prostate, testes, ovary, colon, heart, brain, liver, skeletal muscle, kidney or pancreas (data not shown). Collectively, the restricted expression pattern of CD2BP1 supports the notion that this gene product may be important in hematopoietic cell function and, more specifically, in development and/or activation of mature T cells and NK cells.

EXAMPLE 5
The CD2BP1 SH3 Domain Interacts Directly with the CD2 Cytoplasmic Tail Given that the predicted CD2BP1 protein sequence contains a C-terminal SH3 domain and that the CD2 cytoplasmic tail includes several proline-rich segments to which an SH3 domain might bind, the possibility that the CD2BP1 SH3 domain is necessary and sufficient for binding to the CD2 tail was examined. To this end, a cDNA encoding the SH3 region (bp 1024 to 1382 of the nucleic acid encoding CD2BP1S) was obtained by PCR and inserted into the EcoRI and XhoI sites of the pGEX4T-1 GST expression vector. Purified GST or GST-CD2BP1SH3 fusion protein were incubated with lysates of activated human T lymphocytes as described in the experimental procedures in Example 1. The precipitates were subjected to SDS-PAGE and the CD2 association with the CD2BP1SH3 domain revealed by Western blotting with polyclonal anti-CD2 heteroantisera (M32B) raised against the recombinant hCD2 ectodomain. As a positive control, lysates were immunoprecipitated with the anti-CD2 mAb 3T48B5 (Meuer et al., 1984) and then subjected to the same Western blot analysis.

The results (data not shown) demonstrated a broad band in the 50–60 kDa range in the anti-CD2 immunoprecipitate; this broad band is consistent with the known size of the glycosylated CD2 monomer (Sayre et al., 1987; Seed and Aruffo, 1987). 100–120 kDa and 200 kDa bands that appeared on the gel (data not shown) probably represent CD2 oligomers. More importantly, in the presence of divalent cations, $Zn^{2+}$, $Mg^{2+}$ or $CA^{2+}$ at 2 μM–2 mM concentrations (data not shown), CD2 is immunoprecipitated with the CD2BP1SH3 fusion protein, but not by GST alone. Moreover, in the absence of divalent cations, no GST-CD2BP1SH3 interaction with CD2 is observed. This result is of note since earlier sequence analysis of the CD2 tail raised the possibility that it might contain a cation binding site (Chang et al., 1989; Chang et al., 1990).

To verify the specificity of the CD2 tail interaction with the CD2BP1SH3 domain, cell lysates were prepared from the mouse T cell hybridoma cells W33 and Δ25-2, representing variants of the 155.16 cell line which were retrovirally transduced with wt human CD2 or a CD2 cytoplasmic tail minus variant, respectively (Li et al., 1996). As expected, the GST-CD2BP1SH3 protein specifically interacts with the intact CD2 molecule in W33 but not the tail truncated CD2 molecule in Δ25-2 (data not shown).

Thus, the yeast two-hybrid analysis demonstrated that the SH3 domain of CD2BP1, relative to the intact CD2BP1 protein, shows but a weak interaction with the CD2 tail. This weak interaction is not peculiar to the junction formed between the B42 domain and the CD2BP1 SH3 domain in the fusion protein, as the various constructs that were tested included from 0–80 endogenous amino acids of the CD2BP1 segment immediately N-terminal to the CD2BP1 SH3 domain, or, alternatively, an exogenous insertion of a glycine linker between B42 and CD2BP1 SH3 domain; yet all of these constructs yielded a weak signal. A low affinity interaction between the CD2BP1 SH3 domain and the CD2 cytoplasmic tail was also suggested by the immunoprecipitation studies using T cell lysates and a GST-SH3 fusion protein coupled to Sepharose beads. Large amounts of CD2BP1SH3 protein (i.e. mg/ml concentrations) were needed for coupling to Sepharose bead in order to discern an association with CD2. Moreover, the presence of divalent cations was required to detect an association. Given that sequences reminiscent of a cation binding site were previously noted in the CD2 tail (Chang et al., 1989; Chang et al., 1990), a preferred configuration induced by divalent cations may be required to facilitate binding of the CD2BP1 SH3 domain to the CD2 tail. Whether the increase in intracellular free calcium following CD2 and TCR ligation enhances CD2BP1 binding physiologically represents a likely possibility.

EXAMPLE 6
Localization of the CD2BP1 Binding Site on the CD2 Cytoplasmic Tail

Experiments on rat CD2 have provided evidence that the region homologous to human CD2 aa 297–314 is capable of interacting with the SH3 domain of $p56^{lck}$ (Bell et al., 1996). Moreover, it is claimed that augmentation of human CD2–CD58 avidity by an inside-out signaling pathway functionally linked to the TCR involves a portion of this conserved region carboxy terminal to a PPLP (SEQ ID NO:25) site (Hahn and Bierer, 1993), which is one of five proline-rich (PXXP (SEQ ID NO:26)) segments within the CD2 tail. Previous studies have indicated that in human CD2, the region important for CD2-based IL2 production lies outside the conserved C-terminal region: the two most N-terminal sequences (PPPGHR) (SEQ ID NO:21) (amino acids 260–265 and 274–279) are necessary for signal transduction resulting in CD2-triggered IL-2 production and calcium flux (Chang et al., 1989; Hahn and Bierer, 1993).

While the functions of the other proline-rich segments are yet to be defined, it is noteworthy that the C-terminal two proline-rich segments fall within a sequence of 18 amino acids which is the most highly conserved CD2 cytoplasmic tail region across all species studies to date (Clayton et al., 1987; Tavernor et al., 1994). Thus, the CD2 cytoplasmic tail appears to contain several functional regions.

Figure 6:
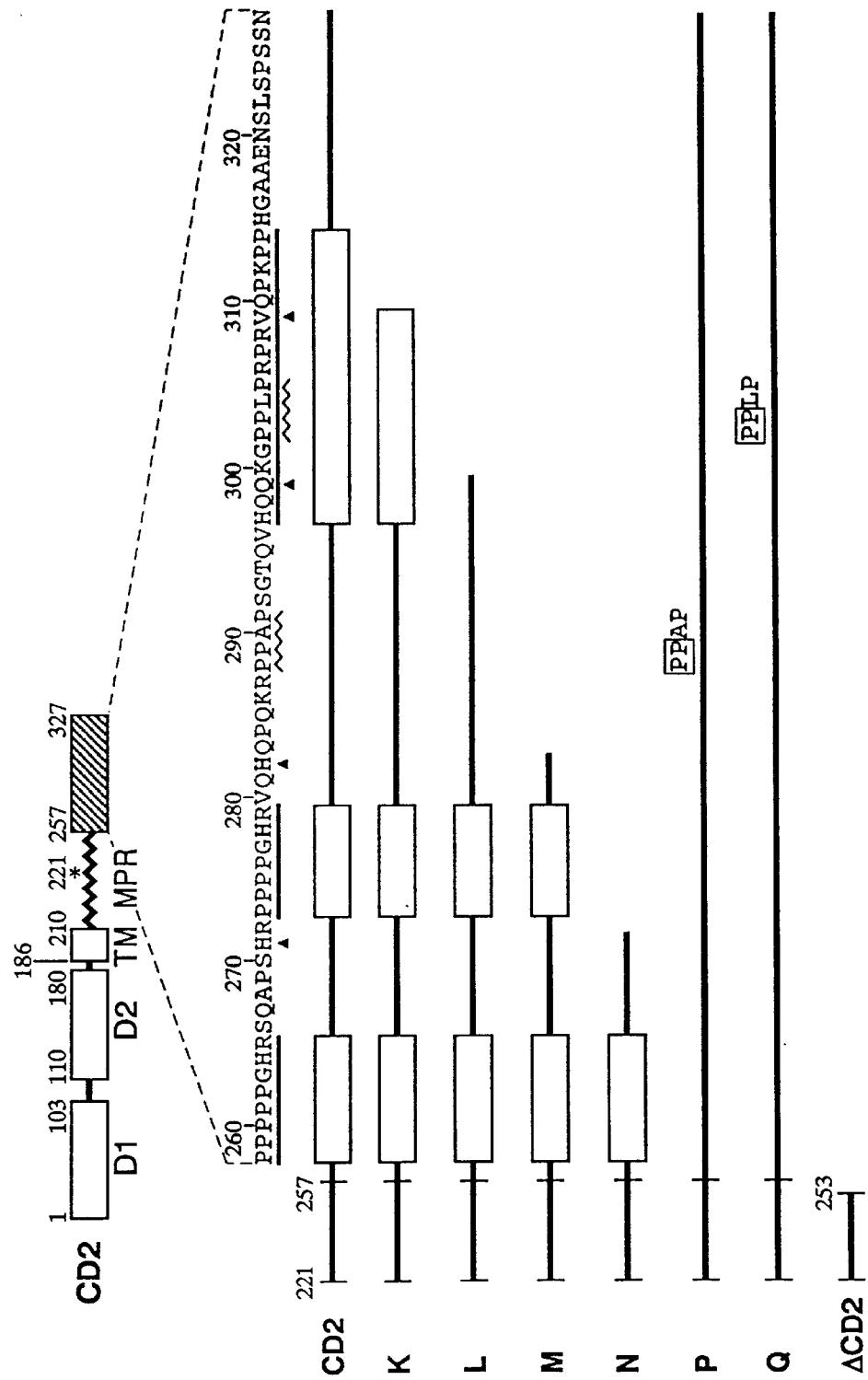
FIG. 6 is a schematic representation of the structure of the CD2 protein, including a portion (SEQ ID NO:15) of the CD2 sequence showing the proline-rich segments within the tail; and of the structure of several truncation variants of the CD2 tail, including construct K, containing all but the carboxy terminal half of the most conserved sequence; construct L, containing a proline-rich sequence (PPAP (SEQ ID NO:20)) in addition to the PPPGHR (SEQ ID NO:21) motifs but lacking the carboxy terminal conserved region; construct M, containing both PPPGHR (SEQ ID NO:21) sequences; construct N, containing only the most amino terminal PPGHR (SEQ ID NO:22) motif; construct P, having a deletion of proline residues 288 and 289; construct Q, having a deletion of proline residues 302 and 303; and construct ACD2, having a deletion of all amino acids after 253.

Given the likelihood that the CD2BP1 protein would interact with one of the proline-rich segments via its SH3 domain, different truncation variants of the CD2 tail in the yeast vector described above were constructed, in order to pinpoint the site of the CD2BP1 SH3 interaction. Construct N contains only the most amino terminal PPPGHR (SEQ ID NO:21) motif, construct M contains both PPPGHR (SEQ ID NO:21) sequences, construct L contains a proline-rich sequence (PPAP) (SEQ ID NO:20) in addition to the PPPGHR (SEQ ID NO:21) motifs but lacks the carboxy terminal conserved region, and construct K contains all but the carboxy terminal half of the most conserved sequence. These and other constructs, as well as the native CD2, are depicted in FIG. 6. In FIG. 6, D1 and D2 represent domain 1 and domain 2 of the extracellular fragment of CD2, respectively; TM represents the transmembrane segment of CD2 and MPR represents the membrane proximal region of the CD2 tail. The amino acid numbers corresponding to each fragment are shown. All of the different CD2 tail variants in the pEG202 fusion include amino acids 221–257 except ΔCD2 as indicated. The three proline rich regions conserved among species are underlined; two of the proline rich sequences are indicated by zig zag lines. Different truncated fragments are shown with their truncation sites labeled as solid triangle under the sequence. The last amino acid of each variant includes the residue denoted by the solid triangle. Two prolines (boxed) were removed from the PPAP (SEQ ID NO:20) sequence in construct P and two proline were removed from the PPLP (SEQ ID NO:25) sequence in construct Q.

Figure 7:
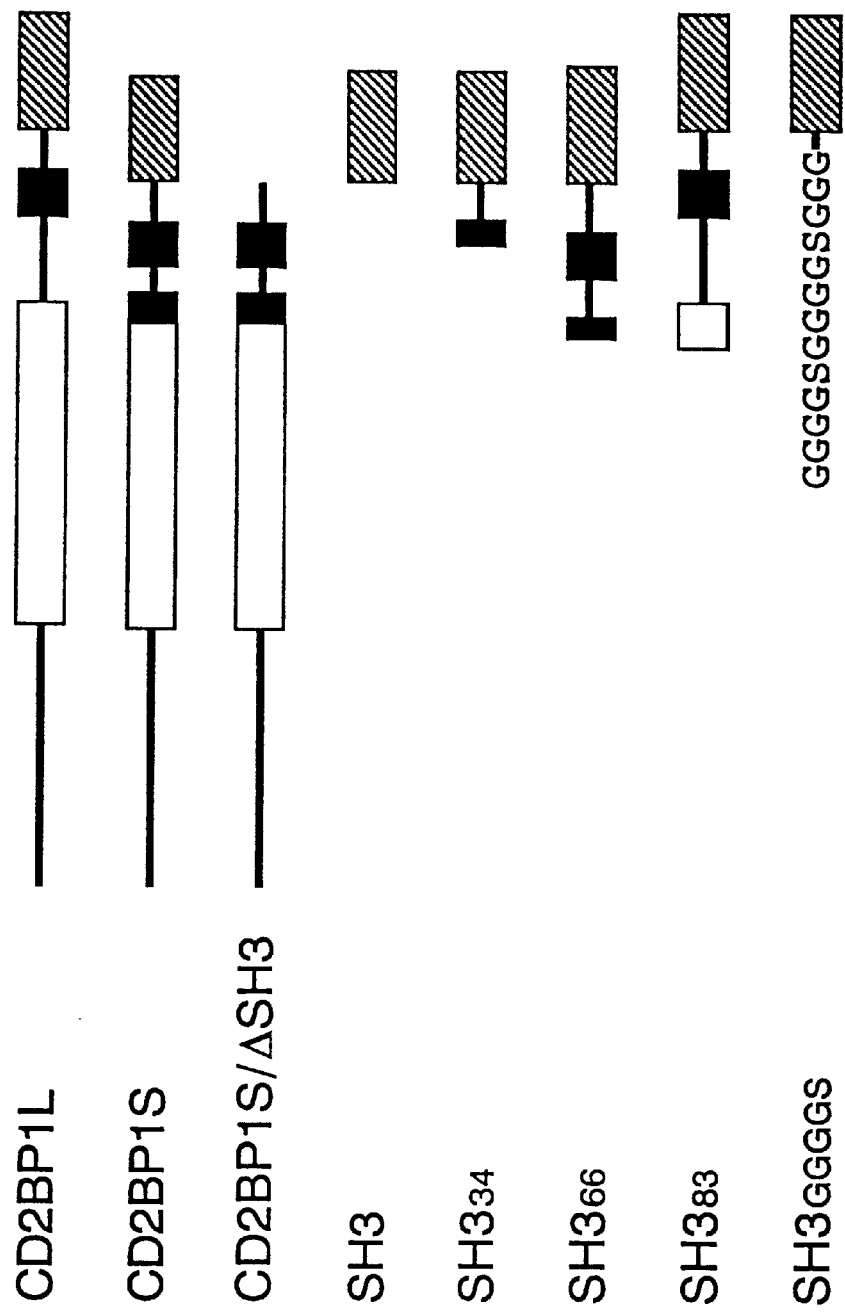
FIG. 7 is a schematic representation of the structure of CD2BP1L; CD2BP1S; CD2BP1S/ΔSH3 (a CD2BP1S truncation construct lacking the terminal SH3 domain); the SH3 domain alone; a CD2BP1S truncation construct consisting of the SH3 domain plus 34, 66 or 83 N-terminal residues ($SH3_{34}$, $SH3_{66}$ or $SH3_{83}$, respectively); and the SH3 domain alone with an artificial N-terminal linker ($SH3_{GGGGS}$) (GGGGS is SEQ ID NO:23).

These tail variants were tested in the yeast two-hybrid system for their interaction with CD2BP1L or CD2BP1S as well as CD2BP1 truncations. These constructs are shown in FIG. 7. In FIG. 7, open bars represent the region of CD2BP 1 sequence with homology to yeast cdc15 protein aa 116–277; solid bars represent PEST rich regions in the CD2BP1 sequences; and hatched bars represent the SH3 domain in the CD2BP1 sequences. CD2BP1S/Δ5SH3 represents CD2BP 1 lacking the SH3 domain. $SH3_{34}$ includes the entire SH3 domain of CD2BP 1 and 34 N-terminal amino acids. $SH3_{66}$ includes the SH3 domain of CD2BP1S and 66 N-terminal amino acids. $SH3_{83}$ includes the SH3 domain of CD2BP1L and 83 N-terminal amino acids of CD2BP1L. $SH3_{GGGGS}$ (GGGGS is SEQ ID NO:23) includes the entire SH3 domain of CD2BP1 and an artificial N-terminal linker consisting of the residues shown.

The strength of the interaction between the CD2 variants and the CD2BP1 constructs was determined by lacZ induction. The results are shown in Table 1, below.

TABLE 1

Mapping of the Interaction Between the CD2 Cytoplasmic Tail and CD2BP1 in a Yeast Two-Hybrid System

| | CD2* | K | L | M | N | P | Q | ΔCD2 |
|---|---|---|---|---|---|---|---|---|
| CD2BP1S | ++++[1] | ++++ | – | – | – | ++++ | ++ | – |
| CD2BP1L | ++++ | ++++ | – | – | – | ++++ | ++ | – |
| CD2BP1S/ΔSH3 | – | – | – | – | – | – | – | – |
| $SH3_{34}$ | + | + | – | – | – | + | – | – |
| $SH3_{GGGGS}$ | + | + | – | – | – | + | – | – |

*Different CD2 tail truncation constructs are shown in FIG. 6, and CD2BP1 constucts are shown in FIG. 7.
[1]Symbols indicate the strength of interaction between the regions of CD2 and CD2BP1 as detected by lacZ expression in the yeast system (++++ > +++ > ++ > + > –).

As summarized in Table 1, the CD2BP1 protein interacts with the CD2 tail in the region between aa 300–309. Hence the K mutant is fully active while the L mutant has lost all activity. Consistent with this notion, deletion of proline residues 302 and 303 results in a marked attenuation of the intermolecular interaction (FIG. 6, construct Q). By contrast, comparable deletion of the proline residues 288 and 289 is without effect (FIG. 6, construct P). As expected, the more extensive CD2 truncations, M and N, are unable to interact with CD2BP1. Analysis of the CD2BP1S variants clearly shows that the CD2BP1 SH3 domain is essential for interaction with the CD2 cytoplasmic tail; CD2BP1S/ΔSH3 cannot interact with CD2. Notwithstanding, the CD2BP1 SH3 domain ($SH3_{34}$) alone interacts but weakly with the CD2 tail. This weak interaction is not secondary to an inhibitory effect of the CD2BP1 sequences immediately N-terminal to its SH3 domain, since removal of these residues and replacement with a synthetic linker, $SH3_{GGGGS}$, fails to augment the response.

EXAMPLE 7
Production of mAbs with Specificity for CD2BP1 and Identification of a 50 kDa Protein in T Lymphocytes To characterize further the structure and function of CD2BP1, mAbs were generated against its SH3 domain. For this purpose, the GST-CD2BP1SH3 domain fusion protein described above in Example 5 was used to repeatedly immunize Balb/C mice. Subsequently, the immunized splenocytes were fused with NS1 myeloma cells and hybridoma clones screened by ELISA for production of mAbs reactive with plate-bound GST-CD2BP1SH3 protein but not plate-bound GST alone. Of the approximately 1600 primary clones screened, four (1E65B4, 8C93D8, 9B411F9, 10C24B7) showed selective specificity for the GST-CD2BP1SH3 fusion protein. Antibody isotypes were determined by the Ouchterlony method (Bergdoll, M. S., J. Assoc. Off. Anal. Chem. 74:706–610 (1991)): 1E65B4 and 10C24B7 belong to the IgM subclass, 9B411F9 belongs to the IgG1 subclass and 8C93D8 belongs to the IgG2a subclass. Binding studies show that the relative affinity of the 8C93D8 is 150–200 fold better than the other mAbs (data not shown). Consistent with this observation, only 8C93D8 was able to immunoprecipitate CD2BP1 protein from T cell lysates.

To identify the CD2BP1 protein in T cells, immunoprecipitations were performed on 1% Triton X-100 lysates of $^{35}S$-methionine labeled activated human T cells using the 8C93D8 mAb coupled to Sepharose 4B (5 mg/ml). In parallel experiments, Sepharose beads comparably coupled with mAbs against human CD2 (anti-T$11_1$ (3T48B5) antibody) and CD4 (19Thy5D7 antibody) were used as positive controls while beads coupled with 2H11 mAb directed against an artificial leucine zipper structure were used as a negative control. After washing of immunoprecipitates, the samples were analyzed by SDS-PAGE under reducing conditions followed by autoradiography. Results (data not shown) demonstrated that 8C93D8 specifically identifies a band at ~50 kDa when compared with control beads. The apparent MW of this band is in good agreement with the predicted size of CD2BP1 derived from the cDNA sequences (47.5 kDa). As expected, the positive control anti-CD2 beads immunoprecipitated a broad CD2 band between 48–55 kDa and anti-CD4 immunoprecipitated a CD4 band at ~64 kDa, respectively (data not shown). The mobility of the CD2BP1 protein did not change under nonreducing conditions (data not shown), implying that CD2BP1 does not exist as disulfide-linked dimers. This is of interest since CD2BP1L contains an additional cysteine at aa 305 which is not found in CD2BP1S (see FIG. 3).

EXAMPLE 8
Crosslinking of CD2 by CD58 or Anti-CD2 mAbs Induces the Association of CD2BP1 with CD2 in T Lymphocytes Both the above biochemical studies with the GST-CD2BP1SH3 fusion protein and the genetic complementation analysis indicate a direct association between the CD2 cytoplasmic tail and the CD2BP1 protein. However, the inability to detect CD2 in the anti-CD2BP1 immunoprecipitates with the 8C93D8 mAb in the Triton X-100 T cell lysates (see Example 7) suggests that the association is weak and/or non-constitutive. To determine the nature of the intermolecular interaction which occurs during physiologic situations in vivo, a series of immunofluorescence co-localization studies was performed. To this end, activated human T cells were analyzed for CD2 and CD2BP1 expression and the distribution pattern of these molecules on the T cell surface and within the T cell compared prior to and following CD2 ligation. Fluorochrome-labeled mAbs specific for the extracellular adhesion domain of CD2 (anti-T$11_1$ Texas Red or anti-T$11_3$ Texas Red) were used to detect CD2 on the cell surface and the CD2BP1 SH3-specific mAb 8C93D8-FITC was used for intracellular localization of CD2BP1.

Results showed that the staining of CD2 on activated T cells gives a characteristic rim-like pattern representing a broad surface membrane distribution (data not shown). In contrast, staining of CD2BP1 with 8C93D8 exhibits a diffuse intracellular staining pattern, a lack of nuclear staining and a weak surface membrane reactivity (data not shown).

This result indicates that the CD2BP1 protein mainly localizes to the cytosol of the T cell. On the other hand, when CD2 molecules are crosslinked by anti-CD2 mAbs (anti-T11$_2$+anti-T11$_3$-Texas Red), they redistribute in clusters on the T cell surface (data not shown). Moreover, the staining pattern of CD2BP1 changes substantially. The previously rather uniform CD2BP1 cytoplasmic distribution becomes clustered near the cell surface membrane as well, with the CD2BP1 staining now co-localizing with the surface CD2 staining (data not shown). This overlap was readily visualized as yellow staining given that the combination of Texas-red CD2 staining and green FITC-CD2BP1 staining overlap (data not shown).

To determine whether binding of CD58 to the CD2 ectodomain might induce the association of CD2BP1 with CD2, cell-cell conjugates were formed between CD2 expressing activated T cells and human CD58-transfected CHO cells and the distribution of the CD2 and CD2BP1 proteins examined. When human CD58 transfected CHO cells interact with T cells, the CD2 redistributes on the T cell surface to the region of the cell-cell interaction interface, consistent with our prior results (data not shown) (Li et al., 1996). More importantly, the CD2BP1 protein reorganizes into the area of cell-cell contact as well (data not shown)). The co-localization of CD2 and CD2BP1 following CD2 crosslinking by specific anti-CD2 mAbs or the CD58 ligand itself supports the conclusion that CD2 and CD2BP1 associate with one another during specific in vivo conditions in T lymphocytes. Furthermore, it is clear that this association is predominantly not constitutive but rather induced by ligation of the CD2 ectodomain. To some extent, even T cell-T cell interaction induces co-localization as well (data not shown).

EXAMPLE 9
CD2BP1 Associates with the Protein Tyrosine Phosphatase (PTP)-PEST Association of CD2BP1 with PTP-PEST The CD2 cytoplasmic tail is known to be critical for signal transduction following ligation of the CD2 ectodomain (Chang et al., 1989; Hahn and Bierer, 1993). Given that the CD2 tail lacks a kinase or phosphatase domain, the most plausible way through which it might exert its effect on cellular activation is via coupling to a second signaling molecule. In principle, this might either be through a direct coupling between the CD2 tail and an enzyme or alternatively, by an intermediate adaptor protein which interacts with CD2 and in turn couples to a kinase or phosphatase. The specific association of CD2BP1 with CD2 both in vitro and in vivo suggests that it is a possible candidate for such a coupling component. Since the amino acid sequence of CD2BP1 shows it to have neither a kinase or phosphatase domain, CD2BP1 probably subserves an adaptor function.

Figure 8:
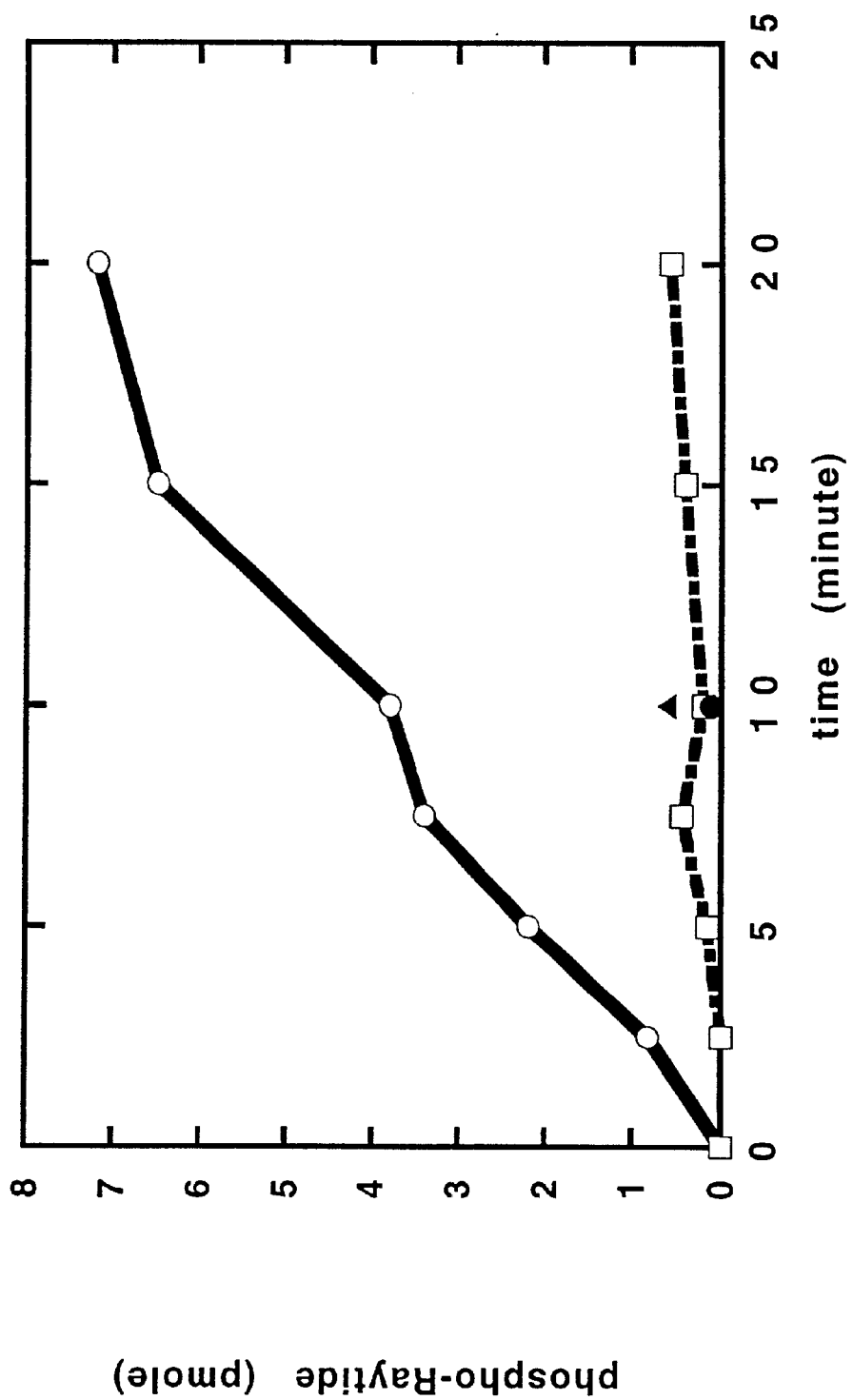
FIG. 8 is a graphic representation of the time-dependent release of $^{32}P$ from tyrosine phosphorylated Raytide by CD2BP1 immunoprecipitates (open circles) and control immunoprecipitates (open squares). Solid triangle, reaction of anti-CD2BP1 immunoprecipitate complexes in the presence of the specific protein tyrosine phosphatase inhibitor sodium vanadate; solid circle, control immunoprecipitate complexes in the presence of sodium vanadate.

To test this possibility, 8C93D8 was used to immunoprecipitate CD2BP1 from activated human T cell lysates and any associated kinase or phosphatase activity was determined by in vitro analysis. In immunoprecipitates made with an irrelevant mouse IgG control vs. the CD2BP1 specific mAb, no serine-threonine kinase or tyrosine kinase activities were found using histone H1 and Raytide or polyGlu-Tyr, respectively, as substrates. However, in contrast to the lack of kinase activity, the CD2BP1 immunoprecipitates showed significant tyrosine phosphatase activity using phospho-Raytide as a substrate. This activity is illustrated in FIG. 8, as a linear time-dependent release of $^{32}$P from tyrosine phosphorylated Raytide; moreover, sodium vanadate, the specific inhibitor of tyrosine phosphatases, blocks this reaction as expected. In FIG. 8, the solid line depicts an assay on immunocomplexes immunoprecipitated by anti-CD2BP1, and the dotted line depicts an assay on immunocomplexes precipitated by control mouse IgG. The solid triangle indicates 10 min assay reaction of anti-CD2BP1 immunocomplexes in the presence of the specific protein tyrosine phosphatase inhibitor sodium vanadate (1 mM). The solid circle indicates the value for the control mouse IgG immunocomplexes assayed under the same reaction condition as in solid triangle. The Y axis represents pmole of $^{32}$P released from phospho-Raytide and the X axis represents time in minutes. The results shown are representative of three independent experiments.

Given the cytosolic distribution of CD2BP1, the possibility that a cytosolic PTP was the enzyme in question was investigated. To this end, the association of CD2BP1 with the known cytoplasmic PTPs, PEST-PTP (Garton and Tonks, 1994), SHPTP1 (Matthews et al., 1992; Plutzky et al., 1992) and SHPTP2 (Freeman et al., 1992) was tested. FLP which, according to some studies, has a cytosolic distribution (Cheng et al., 1996; Dosil et al., 1996), was also tested. For these experiments, activated T cell lysates were incubated with 8C93D8-Sepharose or control mouse IgG-Sepharose. Following immunoprecipitation and washing, the bead-bound material was subjected to SDS-PAGE, blotted to nitrocellulose membranes and incubated with polyclonal anti-PTP PEST (Garton and Tonks, 1994), anti-FLP (anti-EN12)(Dosil et al., 1996) or anti-SHPTP1 and anti-SHPTP2 antibodies (Freeman et al., 1992; Plutzky et al., 1992), and developed by ECL.

Results (data not shown) demonstrated that in T cell lysates, the anti-PTP-PEST antisera detected a band at approximately 106 kDa which is the PTP-PEST protein (data not shown). The 8C93D8 anti-CD2BP1 mAb immunoprecipitates the same band, consistent with the notion that PTP-PEST and CD2BP1 coassociate (data not shown). The presence of PTP-PEST protein in the 8C93D8 immunoprecipitate is specific since no PTP-PEST protein band is observed in the mouse IgG-Sepharose immunoprecipitate (data not shown). To confirm further the specificity of the CD2BP1/PTP-PEST interaction, it was examined whether excess soluble 8C93D8 or mouse IgG antibody preincubation with the T cell lysate could mediate specific inhibition of the immunoprecipitation by Sepharose-bound 8C93D8. As expected, preincubation with soluble mouse IgG had no effect on the PTP-PEST immunoprecipitation (data not shown). In contrast, preincubation of lysates with soluble 8C93D8 resulted in the inability of the 8C93D8 Sepharose to coprecipitate the PTP-PEST band (data not shown). For the comparable controls for nonspecific mouse IgG-Sepharose immunoprecipitation, no 106 kDa band is seen under either preincubation condition, as expected. The results of this soluble antibody competition assay further support the view that CD2BP1 associates specifically with PTP-PEST. In addition to the 106 kDa PTP-PEST band, the 8C93DS antibody also apparently immunoprecipitated a band at approximately 80 kDa from the T cell lysate which reacts with the anti-PTP-PEST antisera by Western blot (data not shown). Whether this band represents a proteolytic product of PTP-PEST or a related but distinct PTP remains to be determined. Parallel analysis of these same lysates and immunoprecipitates with other PTP specific reagents failed to show any association of SHPTP1, SHPTP2 or FLP with the CD2BP1 protein (data not shown).

The Function of the Association of CD2BP1 Protein with PTP-PEST in Cell Signal Transduction and Adhesion Tyrosine phosphorylation of macromolecules is important in many forms of signal transduction processes (Ihle et al., 1995; Matsuzaki et al., 1993; Swain and Cambier, 1996). The regulation of the phosphorylation status of the receptor as well as downstream molecules in the signaling pathway provide a common means for cascade signal amplification control. In the case of cell adhesion, accumulating data has uncovered the importance of tyrosine phosphorylation on components of adhesion complexes as a means of regulating complex formation and function (Kanner et al., 1991; Nakamoto et al., 1997; Sakai et al., 1994; Schlaepfer and Hunter, 1997; Vuori et al., 1996; Vuori and Ruoslahti, 1995). In this regard, the control of the level of tyrosine phosphorylation and dephosphorylation reactions by kinases and phosphatases, respectively, is central for signal transduction and cell adhesion events (Black and Bliska, 1997; Chow et al., 1993; Howell and Cooper, 1994; Liu et al., 1996; Tobe et al., 1996).

PTP-PEST is a widely expressed protein tyrosine phosphatase with a cytosolic distribution. It contributes >90% of the cytosolic tyrosine phosphatase activity in most cells and is maintained in a constantly active state (Garton et al., 1996). Recently, by using substrate-trapping techniques, it was reported that PTP-PEST manifests a very restricted substrate specificity towards the tyrosine phosphorylated protein p130$^{CAS}$ (Garton et al., 1997; Garton et al., 1996). The latter has been observed as a non-phosphorylated species in resting cells and participates in focal adhesion complex formation in a phosphorylated form upon activation either by integrin-mediated cell adhesion or oncogene-mediated cell transformation (Astier et al., 1997; Kanner et al., 1991; Mayer and Hanafusa, 1990; Nojima et al., 1995; Petruzzelli et al., 1996; Salgia et al., 1996; Vuori et al., 1996; Vuori and Ruoslahti, 1995). While the exact function of phosphorylated p130$^{CAS}$ in the adhesion complex is unclear, it appears to play a role in the adhesion complex formation and stabilization by interaction with other constituents through its phosphotyrosine residues (Kanner et al., 1991; Nakamoto et al., 1997; Petruzzelli et al., 1996; Sakai et al., 1994; Salgia et al., 1996; Vuori et al., 1996). Since CD2BP1 interacts with both the transmembrane CD2 protein and the cytosolic PTP-PEST protein, it may be linked directly or indirectly to phosphorylated p130$^{CAS}$ function. As shown here and elsewhere (Koyasu et al., 1990; Li et al., 1996), as CD2 reorganizes into the cell-cell adhesion junction, it becomes highly concentrated. Through targeting to the CD2 tail, CD2BP1 brings the associated PTP-PEST to the membrane in the region of cell-cell contact. This may facilitate the PTP-PEST's ability to dephosphorylate the phosphorylated p130$^{CAS}$ in the focal adhesion complex, thereby down-regulating the adhesion complex. Interestingly, a bacterial PTP (YopH) has been reported to dephosphorylate p130$^{CAS}$ and cause destabilization of focal adhesions (Black and Bliska, 1997).

It is noteworthy that PTP-PEST has recently been found to associate with the inhibitory signaling molecule csk through the interaction of the proline-rich sequence of PTP-PEST with the cskSH3 domain (Davidson et al., 1997). csk functions by phosphorylating the C-terminal regulatory tyrosine on src-kinase family members, thereby inactivating their enzymatic activity (Chow et al., 1993; Cloutier et al., 1995). csk has been reported to localize to focal adhesions via its SH2 and SH3 domain interaction with src (Howell and Cooper, 1994; Sabe et al., 1994). In turn, src is constitutively present in focal adhesions where it phosphorylates other components of the complex such as FAK and p130$^{CAS}$ (Nakamoto et al., 1997; Vuori et al., 1996; Vuori and Ruoslahti, 1995). A direct interaction of csk with FAK and paxillin through the csk SH2 domain has also been reported (Bergman et al., 1995; Tobe et al., 1996). The concerted influences of csk and PTP-PEST may be critical for negatively regulating the formation and/or function of the adhesion complex.

PTP-PEST has also been reported to associate with shc and grb2, molecules important for T cell activation events (Charest et al., 1996; Charest et al., 1997; Habib et al., 1994). The biochemical significance of these associations is currently unclear. However, several reports indicate that shc and grb2 associate with FAK in focal adhesions to provide a link between the focal adhesion complex. and downstream signaling (Schlaepfer et al., 1994; Schlaepfer and Hunter, 1997; Vuori et al., 1996). It seems likely that PTP-PEST might associate with membrane-localized shc or grb2 molecules and thereby modify them by modulating the signal transduction pathways involving these molecules. Consistent with the notion that an adaptor protein such as CD2BP1 might have an important function in regulating cellular activation/adhesion events, BLAST search has identified a murine protein with 88% identity to human CD2BP1 (gi/1857712). This was cloned from mouse hematopoietic progenitor cells and likely associates with PTP-PEST or a closely related PTP.

The detailed mechanisms by which CD2BP1 and PTP-PEST associate is yet to be determined. However, the existence of several proline-rich stretches in the PTP-PEST sequence raises the possibility that the association results from direct interaction of the SH3 domain of CD2BP1 with a proline-rich region (Yang et al., 1993). The inability to detect an interaction between CD2BP1 and SHPTP1, SHPTP2 and FLP attests to the specificity of CD2BP1 interaction with PTP-PEST.

To date, two classes of proline-rich sequences with high affinity for SH3 domains have been documented (Mayer and Eck, 1995). Class I contains the motif RxxPxxP (SEQ ID NO:27) while class II contains the motif PxxPxR (SEQ ID NO:28). These sequences permit the prolines and arginines to interact with the three binding pockets of the SH3 domain's surface. All of the proline-rich sequences in the CD2 tail, including the PPLP (SEQ ID NO:25) sequence lack either of these motifs, perhaps explaining why the single CD2BP1 SH3 domain exhibits weak binding to CD2. The very weak interaction of the isolated CD2BP1 SH3 domain with the CD2 tail suggests that although the SH3 domain is directly involved in binding to the PPLP (SEQ ID NO:25) region of the CD2 cytoplasmic tail, other components of CD2BP1 protein may be important in promoting binding, even if only indirectly. In this regard, the PAIR COIL amino acid sequence analysis (Berger et al., 1995) of CD2BP1 suggests the presence of a coiled-coil structure within the N-terminal half of the protein. Proteins with coiled-coil structures often interact either among themselves or with other coiled-coil proteins through charge interactions or hydrophobic or Van der Waal's forces as distributed on separate surfaces of the coiled-coil helical structure (Cohen and Parry, 1990). The possibility exists, therefore, that CD2BP1 may interact with itself to form oligomers. In fact, the MULTICOIL program (Wolf et al., 1997) predicts the possible formation of CD2BP1 intermolecular trimers. Such oligomerization would undoubtedly increase the avidity of the SH3 domain for its binding partner on the CD2 tail (PPLP (SEQ ID NO:25) region) due to cooperative interactions resulting from the multivalency of the SH3 domains. This possibility could explain the more readily detectable binding in the yeast two-hybrid system between CD2BP1 and the CD2 tail relative to that between the isolated CD2BP1 SH3 domain and the CD2 tail. In addition, such multimerization of CD2BP11SH3 domains would provide independent binding surfaces for several proline-rich regions, suggesting how CD2BP1 might make bridging interactions simultaneously not only with CD2 molecules but with PTP-PEST molecules as well.

Regulation of the local CD2 cytoplasmic tail concentration in the T lymphocyte could also inducibly modulate interactions with the low affinity CD2BP1 SH3 domain. The observation that CD2 co-localizes with CD2BP1when transmembrane CD2 molecules are reorganized into clusters by CD58 suggests that this mechanism may be operative. Clustering of CD2 molecules at the cell-cell interface would result in a high local concentration of CD2 cytoplasmic tails. These in turn would associate with CD2BP1, thereby delivering PTP-PEST to the area of cell-cell interaction. The phosphatase activity of PTP-PEST would then be available to regulate the CD2-mediated cell adhesion process.

The current study documents the existence of two different CD2BP1 isoforms, CD2BP1L and CD2BP1S. Both proteins have an overall sequence similarity with cdc15, (i.e., they possess a cdc15 homology component), a PEST-rich region and an SH3 domain. Results from yeast two hybrid analysis suggest that both interact with the CD2 tail in the same region. However, there are differences between these proteins which could affect their function and fate. As revealed by RT-PCR, the CD2BP1S mRNA is present in low abundance compared to CD2BP1L. In addition, CD2BP1S has two continuous PEST-rich sequences while CD2BP1L has but one, making the CD2BP1S protein possibly more susceptible to degradation. If the postulated protein degradation resulted in a stable N-terminal coiled-coil and/or C-terminal SH3 domain fragment, either might negatively regulate CD2BP1 function. The CD2BP1L isoform uniquely contains a proline-rich sequence PPAP (SEQ ID NO:20) (a potential SH3 binding site), an additional tyrosine residue at aa 283 and a free cysteine (aa 305) which might pair with other protein components. At least under the conditions examined, however, no evidence for CD2BP1L covalently-linked dimers was found.

The RNA expression pattern of CD2BP1 is restricted to hematopoietic cells, being distributed among T cells and NK cell populations and up-regulated further in activated T cells. The distribution pattern of CD2BP1 is similar but not identical to CD2 and suggests that its biological role is relevant to T and NK cell function, presumably through interaction with CD2. Nevertheless, unlike CD2 which is expressed at a high level in the thymus, the expression of CD2BP1 is minimal in thymocytes relative to mature T lymphocytes. This obvious difference in the RNA expression of CD2BP1 between mature and immature T cells is likely linked to the function of the gene product. As discussed above, one potentially important function of CD2BP1 is to recruit PTP-PEST to the CD2 tail, thereby facilitating dephosphorylation of substrates such as $p_{130}^{CAS}$ and presumably resulting in downregulation of the adhesion process. This mechanism may be critical for mature T cell effector function.

REFERENCES

Altschul, S. F., et at., *J Mol Biol* 215, 403–410 (1990).
Arulanandam, A. R. N., et al., *J Exp Med* 180, 1861–1871 (1994).
Arulanandam, A. R. N., et al., *J Exp Med* 177, 1439–1450 (1993a).
Arulanandam, R. R. N., et al., *Proc Natl Acad Sci USA* 90, 11613–11617 (1993b).
Astier, A., et al., *J Biol Chem* 272, 228–232 (1997).
Bell, G. M., et al., *J Exp Med* 183, 169–178 (1996).
Berger, B., et al., *Proc Natl Acad Sci USA* 92, 8259–8263 (1995).
Bergman, M., et al., *Mol Cell Biol* 15, 711–722 (1995).
Bierer, B. E., et al., *J Exp Med* 168, 1145–1156 (1988).
Bierer, B. E., et al., *Annu Rev Immunol* 7, 579–599 (1989).
Black, D. S., and Bliska, J. B., *EMBO J* 16, 2730–2744 (1997).
Bodian, D. L., et al., *Structure* 2, 755–766 (1994).
Boussiotis, V. A., et al., *J Exp Med* 180, 1665–1673 (1994).
Chang, H.-C., et al., *Proc Natl Acad Sci USA* 91, 11408–11412 (1994).
Chang, H.-C., et al., *J Exp Med* 169, 2073–2083 (1989).
Chang, H.-C., et al., *J Exp Med* 172, 351–355 (1990).
Charest, A., et al., *J Biol Chem* 271, 8424–8429 (1996).
Charest, A., et al., *Oncogene* 14, 1643–1651 (1997).
Cheng, J., et al., *Blood* 88, 1156–1167 (1996).
Chow, L. M. L., et al., *Nature* 365, 156–160 (1993).
Clayton, L. K., et al., *Eur J Immunol* 17, 1367–1370 (1987).
Cloutier, J.-F., et al., *Mol Cell Biol* 15, 5937–5944 (1995).
Cohen, C. and Parry, D. A. D., *Proteins: Structure, Function, and Genetics.* 7: 1–15 (1990).
Davidson, D., et al., *J Biol Chem* 272, 23455–23462 (1997).
Dosil, M., et al., *Blood* 88, 4510–4525 (1996).
Driscoll, P. C., et al., *Nature* 353, 762–765 (1991).
Fankhauser, C., et al., *Cell* 82, 435–444 (1995).
Finley, R. L., and Brent, R., "Interaction trap cloning with yeast." In *DNA cloning. 2. Expression systems: A practical approach*, D. M. Glover and B. D. Hames, eds. (Oxford Univ. Press)(1995)
Freeman, R. M., et al., *Proc Natl Acad Sci USA* 89, 11239–11243 (1992).
Garton, A. J., et al., *Oncogene* 15, 877–885 (1997).
Garton, A. J., et al., *Mol Cell Biol* 16, 6408–6418 (1996).
Garton, A. J., and Tonks, N. K., *EMBO J* 13, 3763–3771 (1994).
Gassmann, M., et al., *Eur J Immunol* 24, 139–144 (1994).
Gollob, J. A., et al., *J Immunol* 157, 1886–1893 (1996).
Gollob, J. A., et al., *J Exp Med* 182, 721–731 (1995).
Genetics Computer Group, *GCG Sequence Analysis Software Package* 7 (1991).
Guruprasad, L., et al., *J Mol Biol* 248, 856–866 (1995).
Habib, T., et al., *J Biol Chem* 269, 25243–25246 (1994).
Hahn, W. C., and Bierer, B. E., *J Exp Med* 178, 1831–1836 (1993).
Hathcock, K. S., "T cell enrichment by nonadherence to nylon." In *Current Protocols in Immunology*, J. E. Coligan et al., eds. (John Wiley & Sons) (1994).
Higuchi, R., et al., *Nucl Acids Res* 16, 7351–7367 (1988).
Howell, B. W., and Cooper, J. A., *Mol Cell Biol* 14, 5402–5411 (1994).
Ihle, J. N., et al., *Annu Rev Immunol* 13, 369–398 (1995).
Jones, E. Y., et al., *Nature* 360, 323–239 (1992).
Kanner, S. B., et al., *EMBO J* 10, 1689–1698 (1991).
Kingston, R. E., "Preparation and analysis of RNA: guanidinium method for total RNA preparation." In *Current Protocols in Molecular Biology*, F. M. Ausubel et al., eds. (Greene Publishing & Wiley-Interscience) (1987).
Koyasu, S., et al., *Proc Natl Acad. Sci USA* 87, 2603–2607 (1990).
Krensky, A. M., et al., *J Immunol* 131, 611–616 (1983).
Li, J., et al., *J Mol Biol* 263, 209–226 (1996).
Liu, F., et al., *J Biol Chem* 271, 31290–31295 (1996).
Matsuzaki, Y., et al., *J Exp Med* 178, 1283–1292 (1993).
Matthews, R. J., et al., *Mol Cell Biol* 12, 2396–2405 (1992).
Mayer, B. J., and Eck, M. J., *Current Biol* 5, 364–367 (1995).
Mayer, B. J., and Hanafusa, H., *J Virol* 64, 3581–3589 (1990).

Meuer, S. C., et al., *Cell* 36, 897–906 (1984).
Moingeon, P., et al., *Immunol Rev* 111, 111–114 (1989a).
Moingeon, P., et al., *Nature* 339, 312–314 (1989b).
Musacchio, A., et al., *Prog Biophys Mol Biol* 61, 283–297 (1994).
Nakamoto, T., et al., *Mol Cell Biol* 17, 3884–3897 (1997).
Nojima, Y., et al., *J Biol Chem* 270, 15398–15402 (1995).
Osborn, L., et al., *J Exp Med* 181, 429–434 (1995).
Peterson, A., and Seed, B., *Nature* 329, 842–846 (1987).
Petruzzelli, L., et al., *J Biol Chem* 271, 7796–7801 (1996).
Plutzky, J., et al., *Proc Natl Acad Sci USA* 89, 1123–1127 (1992).
Rechsteiner, M. and Rogers, S. W., *Trends Biochem Sci* 21, 267–271 (1996).
Recny, M. A., et al., *J Biol Chem* 265, 8542–8549 (1990).
Sabe, H., et al., *Proc Natl Acad Sci USA* 91, 3984–3988 (1994).
Sakai, R., et al., *EMBO J* 13, 3748–3756 (1994).
Salgia, R., et al., *J Biol Chem* 271, 25198–25203 (1996).
Sanchez-Madrid, F., et al., *Proc Natl Acad Sci USA* 79, 7489–7493 (1982).
Sayre, P. H., et al., *Proc Natl Acad Sci USA* 84, 2941–2945 (1987).
Sayre, P. H., et al., *J Exp Med* 169, 995–1009 (1989).
Schlaepfer, D. D., et al., *Nature* 372, 786–791 (1994).
Schlaepfer, D. D., and Hunter, T., *J Biol Chem* 272, 12189–13195 (1997).
Seed, B., and Aruffo, A., *Proc Natl Acad Sci USA* 84, 3365–3369 (1987).
Selvaraj, P., et al., *Nature* 326, 400–403, (1987).
Siliciano, R. F., et al., *Nature* 317, 428–430 (1985).
Somoza, C., et al., *J Exp Med* 178, 549–558 (1993).
Springer, T. A. *Nature* 346, 425–434 (1990).
Swain, S. L., and Cambier, J. C., *Curr Opin Immunol* 8, 309–444 (1996).
Tavernor, A. S., et al., *Eur J Biochem* 219, 969–976 (1994).
Tobe, K., et al., *Mol Cell Biol* 16, 4765–4772 (1996).
Tsai, A. Y. M., et al., *J Biol Chem* 266, 10534–10543 (1991).
van der Merwe, P. A., et al., *Curr Biol* 5, 74–84 (1994).
Vuori, K., et al., *Mol Cell Biol* 16, 2606–2613 (1996).
Vuori, K., and Ruoslahti, E., *J Biol Chem* 270, 22259–22262 (1995).
Wingren, A. G., et al., *J Immunol* 151, 1328–1336 (1993).
Withka, J. M., et al., *Structure* 1, 69–81 (1993).
Wolf, E., et al., *Protein Sci* 6, 1179–1189 (1997).
Yang, Q., et al., *J Biol Chem* 268, 6622–6628 (1993).
Yang, S. Y., et al., *J Immunol* 137, 1097–1100 (1986).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An isolated nucleic acid molecule which encodes a CD2BP1 protein selected from the group consisting of: CD2BP1S consisting of the amino acid sequence of SEQ ID NO:2 and CD2BP1L consisting of the amino acid sequence of SEQ ID NO:1.

2. An isolated nucleic acid molecule encoding a CD2BP1L protein consisting of the amino acid sequence of SEQ ID NO:1.

3. The isolated nucleic acid molecule of claim 2, wherein said nucleic acid molecule has the nucleotide sequence of SEQ ID NO:16.

4. An isolated nucleic acid molecule encoding a CD2BP1S protein consisting of the amino acid sequence of SEQ ID NO:2.

5. The isolated nucleic acid molecule of claim 4, wherein said nucleic acid molecule has the nucleotide sequence of SEQ ID NO:18.

6. A DNA construct comprising the isolated nucleic acid molecule of claim 1 operatively linked to a regulatory sequence.

7. A recombinant host cell comprising the isolated nucleic acid molecule of claim 1 operatively linked to a regulatory sequence.

8. A method for preparing a CD2BP1 protein, comprising culturing the recombinant host cell of claim 7.

* * * * *